US010537632B2

(12) United States Patent
David et al.

(10) Patent No.: US 10,537,632 B2
(45) Date of Patent: *Jan. 21, 2020

(54) CANINE PARVOVIRUS (CPV) VIRUS-LIKE PARTICLE (VLP) VACCINES AND USES THEREOF

(71) Applicant: BOEHRINGER INGELHEIM ANIMAL HEALTH USA INC., Duluth, GA (US)

(72) Inventors: Frederic David, Watkinsville, GA (US); Zahia Hannas-Djebbara, Francheville (FR); Herve Poulet, Sainte Foy-les Lyon (FR); Jules Maarten Minke, Nice (FR)

(73) Assignee: BOEHRINGER INGELHEIM ANIMAL HEALTH USA INC., Duluth, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/109,570

(22) Filed: Aug. 22, 2018

(65) Prior Publication Data
US 2019/0000965 A1 Jan. 3, 2019

Related U.S. Application Data

(63) Continuation of application No. 15/265,545, filed on Sep. 14, 2016, now Pat. No. 10,080,798.
(Continued)

(51) Int. Cl.
A61K 39/23 (2006.01)
A61K 39/12 (2006.01)
(Continued)

(52) U.S. Cl.
CPC .............. A61K 39/23 (2013.01); A61K 39/12 (2013.01); A61K 39/135 (2013.01);
(Continued)

(58) Field of Classification Search
None
See application file for complete search history.

(56) References Cited

U.S. PATENT DOCUMENTS 4,971,793 A 11/1990 Wood et al.
6,187,759 B1 2/2001 Tarpey et al.
(Continued)

FOREIGN PATENT DOCUMENTS

WO 2014016362 A1 1/2014

OTHER PUBLICATIONS

De Cramer et al., "Efficacy of vaccination at 4 and 6 weeks in the control of canine parvovirus." Veterinary microbiology 149, No. 1-2 (2011): 126-132.
(Continued)

Primary Examiner — Shanon A. Foley
(74) Attorney, Agent, or Firm — Judy Jarecki-Black; Richard Seeger

(57) ABSTRACT

The present disclosure encompasses canine parvovirus (CPV) vaccines or compositions. The vaccine or composition may be a vaccine or composition containing CPV virus-like particle (VLP), and a preparation method and a use thereof. The CPV VLPs are formed by the CPV VP2 protein. Further, the disclosure broadly encompasses vaccines comprising combinations of MLV and VLP, which are capable of overcoming MDA against a variety of pathogens, which infect a variety of different species.

17 Claims, 16 Drawing Sheets

Specification includes a Sequence Listing.

Related U.S. Application Data

(60) Provisional application No. 62/234,196, filed on Sep. 29, 2015.

(51) Int. Cl.

| | | |
|---|---|---|
| *A61K 39/135* | (2006.01) | |
| *C07K 14/005* | (2006.01) | |
| *C12N 7/00* | (2006.01) | |
| *A61K 39/00* | (2006.01) | |

(52) U.S. Cl.
CPC .............. *C07K 14/005* (2013.01); *C12N 7/00* (2013.01); *A61K 2039/525* (2013.01); *A61K 2039/5258* (2013.01); *A61K 2039/545* (2013.01); *A61K 2039/552* (2013.01); *A61K 2039/575* (2013.01); *A61K 2039/70* (2013.01); *C12N 2750/14323* (2013.01); *C12N 2750/14334* (2013.01); *C12N 2750/14371* (2013.01); *C12N 2770/32123* (2013.01); *C12N 2770/32134* (2013.01)

(56) References Cited

U.S. PATENT DOCUMENTS

| | | | |
|---|---|---|---|
| 6,204,044 | B1 | 3/2001 | Brown |
| 7,179,456 | B2 | 2/2007 | Rommelaere et al. |
| 8,734,808 | B2 | 5/2014 | Kapil |
| 10,080,798 | B2 * | 9/2018 | David .................. A61K 39/135 |
| 2012/0052082 | A1 | 3/2012 | Compans et al. |
| 2013/0273109 | A1 | 10/2013 | Settembre et al. |

OTHER PUBLICATIONS

Decaro et al., "Evidence for immunisation failure in vaccinated adult dogs infected with canine parvovirus type 2c." Microbiologica—Quarterly Journal of Microbiological Sciences 31, No. 1 (2008): 125-130.

Hurtado et al., "Identification of domains in canine parvovirus VP2 essential for the assembly of virus-like particles." Journal of virology 70, No. 8 (1996): 5422-5429.

Paton et al., "Developing vaccines against foot-and-mouth disease and some other exotic viral diseases of livestock." Philosophical Transactions of the Royal Society of London B: Biological Sciences 366, No. 1579 (2011): 2774-2781.

Patil et al., "Neutralizing antibody responses to foot-and-mouth disease quadrivalent (type O, A, C and Asia 1) vaccines in growing calves with pre-existing maternal antibodies." Veterinary Microbiology 169, No. 3-4 (2014): 233-235.

Langeveld et al., "Full protection in mink against mink enteritis virus with new generation canine parvovirus vaccines based on synthetic peptide or recombinant protein." Vaccine 13, No. 11 (1995): 1033-1037.

Ruedl et al., "Virus-like particles as carriers for T-cell epitopes: limited inhibition of T-cell priming by carrier-specific antibodies." Journal of virology 79, No. 2 (2005): 717-724.

Lo-Man et al., "A recombinant virus-like particle system derived from parvovirus as an efficient antigen carrier to elicit a polarized Th1 immune response without adjuvant." European journal of immunology 28, No. 4 (1998): 1401-1407.

Nguyen et al., "High titers of circulating maternal antibodies suppress effector and memory B-cell responses induced by an attenuated rotavirus priming and rotavirus-like particle-immunostimulating complex boosting vaccine regimen." Clinical and Vaccine Immunology 13, No. 4 (2006): 475-485.

Chen et al., "Immunogenicity of virus-like particles containing modified goose parvovirus VP2 protein." Virus research 169, No. 1 (2012): 306-309.

Rommelaere et al., "Oncolytic parvoviruses as cancer therapeutics." Cytokine & growth factor reviews 21, No. 2-3 (2010): 185-195.

\* cited by examiner

| SEQ ID NO | Type | Gene Description |
|---|---|---|
| 1 | Protein | CPV VP2 - GenBank BAD34656.1 |
| 2 | DNA | pVL1393 - 9632 bp baculovirus transfer vector |
| 3 | Protein | CPV VP2 Souriou (serotype 2c) |
| 4 | Protein | Non-Truncated CPV VP2 in pMEB072 |
| 5 | DNA | pMEB072 Codon-optimized nucleic acid encoding CPV VP2 (SEQ ID NO:4) |
| 6 | Protein | Truncated CPV VP2 in pMEB073 |
| 7 | DNA | pMEB073 codon-optimized nucleic acid sequence encoding CPV VP2 (SEQ ID NO:6) |
| 8 | Protein | GenBank: AHW47988.1 (a CPV VP2) |
| 9 | Protein | GenBank: AHW47989.1 (a CPV VP2) |
| 10 | Protein | GenBank: ADA61118.1 (a CPV VP2) |
| 11 | DNA | pMEB072 |
| 12 | DNA | pMEB073 |

*FIG. 1*

| Batch | Step | VLP Band | Total | % VLPs |
|---|---|---|---|---|
| BacMEB072 | D6 Supernatant | 3 | 28 | 11 |
| | 10x Concentrated Supernatant | 20 | 90 | 22 |
| | Pellet 6 μL | 41 | 79 | 52 |
| | Pellet 3 μL | 22 | 52 | 42 |
| Bac MEB073 | D6 Supernatant | 2 | 11 | 18 |
| | 10x Concentrated Supernatant | 31 | 121 | 26 |
| | Pellet 6 μL | 35 | 64 | 55 |
| | Pellet 3 μL | 17 | 34 | 50 |

| Sample Name | Estimated Purity by SDS | Total Protein µg/ml | [CPV VLPs] µg/ml | ELISA Titer in Log10 DO50/ml |
|---|---|---|---|---|
| CPV VLP BacMEB073 P4 10x Concentrated | 53% | 2122 | 1134 | 5.48 |
| CPV VLP BacMEB073 P5 | 54% | 503 | 273 | 4.99 |
| CPV VLP BacMEB073 P5 10x Concentrated | 55% | 1986 | 1096 | 5.60 |
| CPV VLP BacMEB072 P4 10x Concentrated | 43% | 2410 | 1041 | 5.67 |

```
SEQ 1   MSDGAVQPDGGQPAVRNERATGSGNGSGGGGGGGSGGVGISTGTFNNQTEFKFLENGWVE  60
SEQ 3   MSDGAVQPDGGQPAVRNERATGSGNGSGGGGGGGSGGVGISTGTFNNQTEFKFLENGWVE  60
SEQ 4   MSDGAVQPDGGQPAVRNERATGSGNGSGGGGGGGSGGVGISTGTFNNQTEFKFLENGWVE  60
SEQ 6   ------MLKGGQPAVRNERATGSGNGSGGGGGGGSGGVGISTGTFNNQTEFKFLENGWVE  54
              .*************************************************

SEQ 1   ITANSSRLVHLNMPESENYRRVVVNNLDKTAVNGNMALDDTHAQIVTPWSLVDANAWGVW  120
SEQ 3   ITANSSRLVHLNMPESENYRRVVVNNLDKTAVNGNMALDDTHAQIVTPWSLVDANAWGVW  120
SEQ 4   ITANSSRLVHLNMPESENYRRVVVNNLDKTAVNGNMALDDTHAQIVTPWSLVDANAWGVW  120
SEQ 6   ITANSSRLVHLNMPESENYRRVVVNNLDKTAVNGNMALDDTHAQIVTPWSLVDANAWGVW  114
        ************************************************************

SEQ 1   FNPGDWQLIVNTMSELHLVSFEQEIFNVVLKTVSESATQPPTKVYNNDLTASLMVALDSN  180
SEQ 3   FNPGDWQLIVNTMSELHLVSFEQEIFNVVLKTVSESATQPPTKVYNNDLTASLMVALDSN  180
SEQ 4   FNPGDWQLIVNTMSELHLVSFEQEIFNVVLKTVSESATQPPTKVYNNDLTASLMVALDSN  180
SEQ 6   FNPGDWQLIVNTMSELHLVSFEQEIFNVVLKTVSESATQPPTKVYNNDLTASLMVALDSN  174
        ************************************************************

SEQ 1   NTMPFTPAAMRSETLGFYPWKPTIPTPWRYYFQWDRTLIPSHTGTSGTPTNIYHGTDPDD  240
SEQ 3   NTMPFTPAAMRSETLGFYPWKPTIPTPWRYYFQWDRTLIPSHTGTSGTPTNIYHGTDPDD  240
SEQ 4   NTMPFTPAAMRSETLGFYPWKPTIPTPWRYYFQWDRTLIPSHTGTSGTPTNIYHGTDPDD  240
SEQ 6   NTMPFTPAAMRSETLGFYPWKPTIPTPWRYYFQWDRTLIPSHTGTSGTPTNIYHGTDPDD  234
        ************************************************************

SEQ 1   VQFYTIENSVPVHLLRTGDEFATGTFFFDCKPCRLTHTWQTNRALGLPPFLNSLPQAEGG  300
SEQ 3   VQFYTIENSVPVHLLRTGDEFATGTFFFDCKPCRLTHTWQTNRALGLPPFLNSLPQAEGG  300
SEQ 4   VQFYTIENSVPVHLLRTGDEFATGTFFFDCKPCRLTHTWQTNRALGLPPFLNSLPQAEGG  300
SEQ 6   VQFYTIENSVPVHLLRTGDEFATGTFFFDCKPCRLTHTWQTNRALGLPPFLNSLPQAEGG  294
        ************************************************************

SEQ 1   TNFGYIGVQQDKRRGVTQMGNTNYITEATIMRPAEVGYSAPYYSFEASTQGPFKTPIAAG  360
SEQ 3   TNFGYIGVQQDKRRGVTQMGNTNYITEATIMRPAEVGYSAPYYSFEASTQGPFKTPIAAG  360
SEQ 4   TNFGYIGVQQDKRRGVTQMGNTNYITEATIMRPAEVGYSAPYYSFEASTQGPFKTPIAAG  360
SEQ 6   TNFGYIGVQQDKRRGVTQMGNTNYITEATIMRPAEVGYSAPYYSFEASTQGPFKTPIAAG  354
        ************************************************************

SEQ 1   RGGAQTDENQAADGDPRYAFGRQHGQKTTTTGETPERFTYIAHQDTGRYPEGDWIQNINF  420
SEQ 3   RGGAQTDENQAADGDPRYAFGRQHGQKTTTTGETPERFTYIAHQDTGRYPEGDWIQNINF  420
SEQ 4   RGGAQTDENQAADGDPRYAFGRQHGQKTTTTGETPERFTYIAHQDTGRYPEGDWIQNINF  420
SEQ 6   RGGAQTDENQAADGDPRYAFGRQHGQKTTTTGETPERFTYIAHQDTGRYPEGDWIQNINF  414
        ************************************************************

SEQ 1   NLPVTEDNVLLPTDPIGGKTGINYTNIFNTYGPLTALNNVPPVYPNGQIWDKEFDTDLKP  480
SEQ 3   NLPVTEDNVLLPTDPIGGKTGINYTNIFNTYGPLTALNNVPPVYPNGQIWDKEFDTDLKP  480
SEQ 4   NLPVTEDNVLLPTDPIGGKTGINYTNIFNTYGPLTALNNVPPVYPNGQIWDKEFDTDLKP  480
SEQ 6   NLPVTEDNVLLPTDPIGGKTGINYTNIFNTYGPLTALNNVPPVYPNGQIWDKEFDTDLKP  474
        ************************************************************

SEQ 1   RLHVNAPFVCQNNCPGQLFVKVAPNLTNEYDPDASANMSRIVTYSDFWWKGKLVFKAKLR  540
SEQ 3   RLHVNAPFVCQNNCPGQLFVKVAPNLTNEYDPDASANMSRIVTYSDFWWKGKLVFKAKLR  540
SEQ 4   RLHVNAPFVCQNNCPGQLFVKVAPNLTNEYDPDASANMSRIVTYSDFWWKGKLVFKAKLR  540
SEQ 6   RLHVNAPFVCQNNCPGQLFVKVAPNLTNEYDPDASANMSRIVTYSDFWWKGKLVFKAKLR  534
        ************************************************************

SEQ 1   ASHTWNPIQQMSINVDNQFNYVPSNIGGMKIVYEKSQLAPRKLY  584
SEQ 3   ASHTWNPIQQMSINVDNQFNYVPSNIGGMKIVYEKSQLAPRKLY  584
SEQ 4   ASHTWNPIQQMSINVDNQFNYVPSNIGGMKIVYEKSQLAPRKLY  584
SEQ 6   ASHTWNPIQQMSINVDNQFNYVPSNIGGMKIVYEKSQLAPRKLY  578
        ********************************************
```

*FIG. 11*

Example 7: % Responders

CANINE PARVOVIRUS (CPV) VIRUS-LIKE PARTICLE (VLP) VACCINES AND USES THEREOF

CROSS-REFERENCE TO RELATED APPLICATIONS

This application is a continuation of U.S. patent application Ser. No. 15/265,545, filed Sep. 14, 2016, which claims the benefit of U.S. Patent Application No. 62/234,196, filed Sep. 29, 2015, the entire contents of which are hereby incorporated by reference herein. All other references cited herein are similar incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER 14-252P_ST25.txt. The text file is 82 KB; it was created on Jul. 13, 2015; and it is being submitted electronically via EFS-Web, concurrent with the filing of the specification.

FIELD OF THE INVENTION

The present invention relates to the field of vaccinology, and more particularly, to the challenge of overcoming maternally-derived antibodies (MDA). More particularly, the invention relates to overcoming MDA by administering to animals, including dogs, a combination of virus-like particles and modified live virus (MLV), either in simultaneous combination, sequential administration, or via a prime-boost administration regime. Even more particularly, the invention relates to compositions for eliciting protective immunity against parvovirus (CPV) in dogs and puppies, whether or not CPV MDA are present in the dogs and puppies.

BACKGROUND OF THE INVENTION

Canine parvovirus (CPV) is primarily an enteric pathogen that infects dogs, especially young dogs. Parvovirus infection is characterized by acute diarrhea, fever and leukopenia in dogs and puppies more than 4 to 5 weeks old, and in rare cases myocardial disease in younger puppies. The mortality rate from the disease in unvaccinated dogs is very high. And while several CPV vaccines exist, the presence of maternally-derived antibodies (MDA) tends to block the ability of otherwise effective vaccines to provide protective immunity.

Newborn puppies acquire passive immunities against diseases such as CPV infection by nursing from their mother, especially during the first two days of life. A puppy that nurses takes in colostrum in the milk that is first produced and (MDA) in the colostrum are passed to the puppy. For dogs—and many other mammals—the level of passive immunity provided by the colostrum gradually decreases as MDA are catabolized. As such, the age at which a puppy is no longer protected by MDA varies widely, depending upon the puppy's intake of colostrum, the amount of antibodies contained therein, and several other factors.

A particular challenge when vaccinating puppies is to administer vaccines according to a time frame that provides protection which overlaps the protection provided by maternal antibodies and begins as maternal antibodies wane. Currently, vaccine regimens for puppies typically begin at about 6 weeks of age and boosters are given about every 3 weeks thereafter, e.g. at 9, 12 and sometimes 15 weeks. However, in order for this regimen to provide full protection, the first vaccine dose would have to immediately elicit a protective immune response. This expectation is entirely unrealistic due, in part, to the immaturity of the puppy's immune system and the time period required to mount an immune response. Moreover, the situation is further complicated because residual MDA, which may persist up to about six weeks of age, neutralize MLV vaccines. Currently, all commercially available CPV vaccines are MLV vaccines.

Importantly, while a puppy with CPV MDA may not respond to any MLV CPV vaccine, it can still be infected by a virulent field strain of CPV, and develop canine parvovirosis. Because of the MDA interference, full protection usually does not develop until the entire course of vaccinations is given. As a consequence, the age-based mortality due to CPV infection peaks prior to completion of vaccination protocols. Accordingly, developing a vaccine that actively immunizes puppies after the first injection—and in the presence of MDA—is one of the most important unmet needs in canine medicine.

Another challenge in veterinary medicine is the treatment of cancer, e.g., in dogs. There are many limitations in the existing tools for cancer therapy, especially for geriatric dogs. The administration of oncolytic parvoviruses to kill cancer cells shows great promise as an effective cancer treatment (Rommelaere et al, Cytokine & Growth Factor Reviews 21:185-195, 2010; and U.S. Pat. No. 7,179,456 to Rommelaere et al, the complete contents of which are herein incorporated by reference) and might be applied to canines. However, the existence of pre-existing antibodies to parvoviruses (e.g. as a result of vaccination) would render this method ineffective, since the parvovirus would be neutralized by the existing antibodies. In addition, gene therapy in dogs is rarely undertaken at present but would be a promising method for treating several disorders, if suitable nucleic acid vectors are identified. Accordingly, methods to overcome existing antibodies would be useful for applications beyond vaccination.

In light of the above, there is a need for vaccines with an improved safety and a good efficacy, including the ability to overcome MDA including vaccines that provide protection against heterologous CPV strains.

SUMMARY OF THE INVENTION

The present invention provides pharmaceutical compositions comprising CPV virus-like particle (VLP) antigens, CPV modified live virus (MLV) vaccines, methods of vaccination against CPV, and kits for use with such methods and compositions.

Compositions or vaccines comprising an antigenic CPV polypeptide and fragments and variants thereof are provided. The CPV antigens and fragments and variants thereof possess immunogenic and protective properties. The CPV antigens may be produced by a baculovirus expression vector in insect cells, and assemble into CPV empty capsids or CPV VLPs (virus-like particles).

The antigenic polypeptides and fragments and variants thereof can be formulated into vaccines with or without CPV modified live viruses and/or pharmaceutical compositions. Such vaccines or compositions can be used to vaccinate an animal and provide protection against homologous and heterologous CPV strains.

Importantly, the inventors have surprisingly and unexpectedly found that administration of compositions comprising both a MLV and a VLP (each an antigen corresponding to the same pathogen, but not necessarily encoding or providing the same portion or gene or subunit thereof), is capable of overcoming MDA to elicit protective immunity against subsequent virulent challenge by said pathogen. Accordingly, in a particular embodiment, the invention provides combination vaccines comprising both MLV CPV and CPV VLP, which elicit protective immunity in puppies whether or not the puppies have circulating MDA against CPV.

In another embodiment, the invention provides combination vaccines comprising both MLV and VLP corresponding to other pathogens, where MDA interference is a concern. For example, young bovines, porcines, felines, caprines, ovines, equines and others have circulating MDA against various pathogens. In each case, the presence of these MDA may interfere with the efficacy of vaccines. Now that this disclosure has been made, the inventors envision that administering a combination of both MLV+VLP will overcome MDA irrespective of the pathogen. Pathogens may include, but are not limited to: foot-and-mouth-disease virus (FMDV), porcine reproductive and respiratory syndrome virus (PRRSV), canine distemper virus (CDV), feline panleukopenia FPL, and equine influenza virus (EIV). The skilled person will appreciate that this approach, providing MLV+VLP may be applied in any case where interference by MDA is a challenge.

Kits comprising at least one antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts a table summarizing the DNA and Protein sequences;

FIG. 6 is a Western Blot showing levels of CPV VLPs and accompanying data;

FIG. 7 is a graph showing ELISA-determined CPV titers post vaccination;

FIG. 8 is a graph showing ELISA-determined CPV titers post vaccination with Souriou & Bari strains (low dose, no adjuvant) or pMEB072-produced CPV VLP. Onset is more rapid in group receiving VLP;

FIG. 9 is a graph showing ELISA-determined CPV titers post vaccination with Souriou & Bari strains (intermediate dose, with adjuvant) or pMEB073-produced CPV VLP (with $Al(OH)_3$+saponin). Onset is still more rapid in group receiving VLP;

FIG. 10 is a graph showing ELISA-determined CPV titers post vaccination with Souriou & Bari strains (high dose) or pMEB073-produced CPV VLP (with $Al(OH)_3$+saponin). Onset is rapid with all three groups;

FIG. 11 is a ClustalW alignment of SEQ ID NOs: 1, 3, 4 and 6;

FIG. 12 is a graph showing individual anti-CPV antibody titers (IHA) according to treatment (MLV or MLV+VLP on D0) and day. Each line corresponds to one individual, and the size of the points corresponds to number of values at the indicated combination of day and titer. Only data from dogs having D0 IHA titer ≥40 are shown;

FIG. 13 is a graph showing mean anti-CPV antibody titers (IHA) according to treatment (MLV or MLV+VLP on D0) and day. Boxes represent median, 25th and 75th percentiles, and ends of the whiskers represent values within 1.5 times the interquartile range; each symbol represents one value;

FIG. 14 is a graph showing mean anti-CPV antibody titers (determined by ELISA log 10 OD50) according to day post vaccination and group (Gr A: VLP SC 500 μl; Gr D VLP oral; Gr E Ad5 CPV 8.64 log 10; Gr G Ad5 CDV). Dogs were vaccinated on D0 and D28. Means are represented+/− one standard error of the mean; each dot represents one value;

FIG. 15 is a graph showing percent responders for the study disclosed in Example 7;

FIG. 16 is a graph showing HAI titers;

FIG. 17 is a graph showing Geometric Mean Titer of CPV-neutralizing Antibodies FIG. 18 is a graph showing Percentage Responders by Group and Day;

FIG. 19 is a graph showing CPV Geometric Mean Antibody titer by Group and Day.

DETAILED DESCRIPTION

Compositions comprising a CPV polypeptide, antigen and fragments and variants thereof that elicit an immunogenic response in an animal are provided. The antigenic polypeptides or fragments or variants thereof are produced by a baculovirus expression vector in insect cells. The antigenic polypeptides or fragments or variants may be formulated into vaccines with or without CPV modified live viruses or pharmaceutical compositions and used to elicit or stimulate a protective response in an animal. In one embodiment the polypeptide antigen is a CPV capsid polypeptide or active fragment or variant thereof. The CPV antigens may be assembled into CPV empty capsids or CPV VLPs (virus-like particles).

It is recognized that the antigenic polypeptides of the invention may be full length polypeptides or active fragments or variants thereof. By "active fragments" or "active variants" is intended that the fragments or variants retain the antigenic nature of the polypeptide. Thus, the present invention encompasses any CPV polypeptide, antigen, epitope or immunogen that elicits an immunogenic response in an animal. The CPV polypeptide, antigen, epitope or immunogen may be any CPV polypeptide, antigen, epitope or immunogen, such as, but not limited to, a protein, peptide or fragment or variant thereof, that elicits, induces or stimulates a response in an animal, such as an ovine, bovine, caprine or porcine.

The present invention relates to canine vaccines or compositions which may comprise an effective amount of a recombinant CPV antigen. In some embodiments, the vaccines or compositions are non-adjuvanted, and may comprise a pharmaceutically or veterinarily acceptable carrier, excipient, or vehicle.

In some embodiments, the response in the animal is a protective immune response.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), swine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

Figure 2:
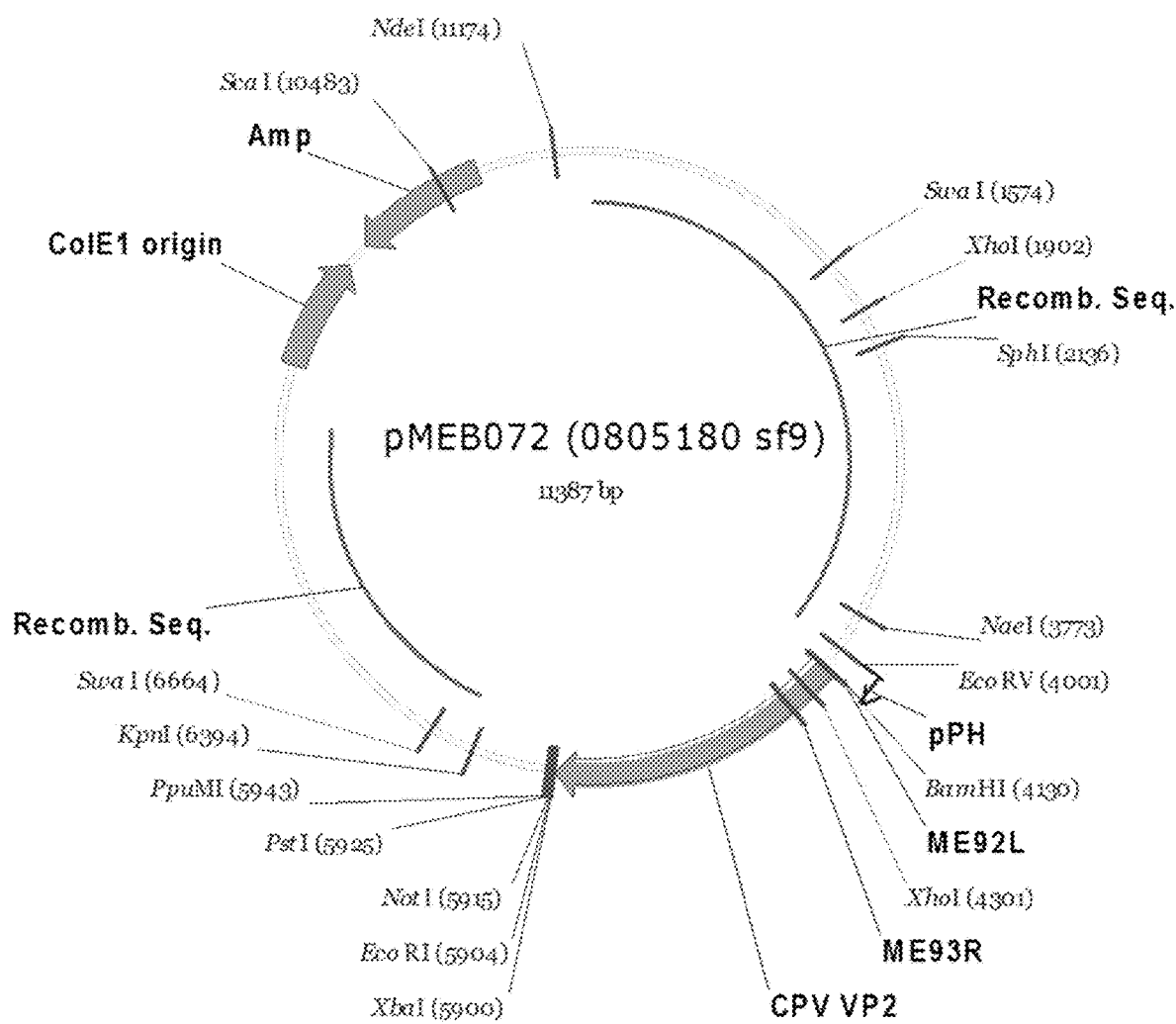
FIG. 2 depicts the plasmid map of pMEB072.
Figure 3:
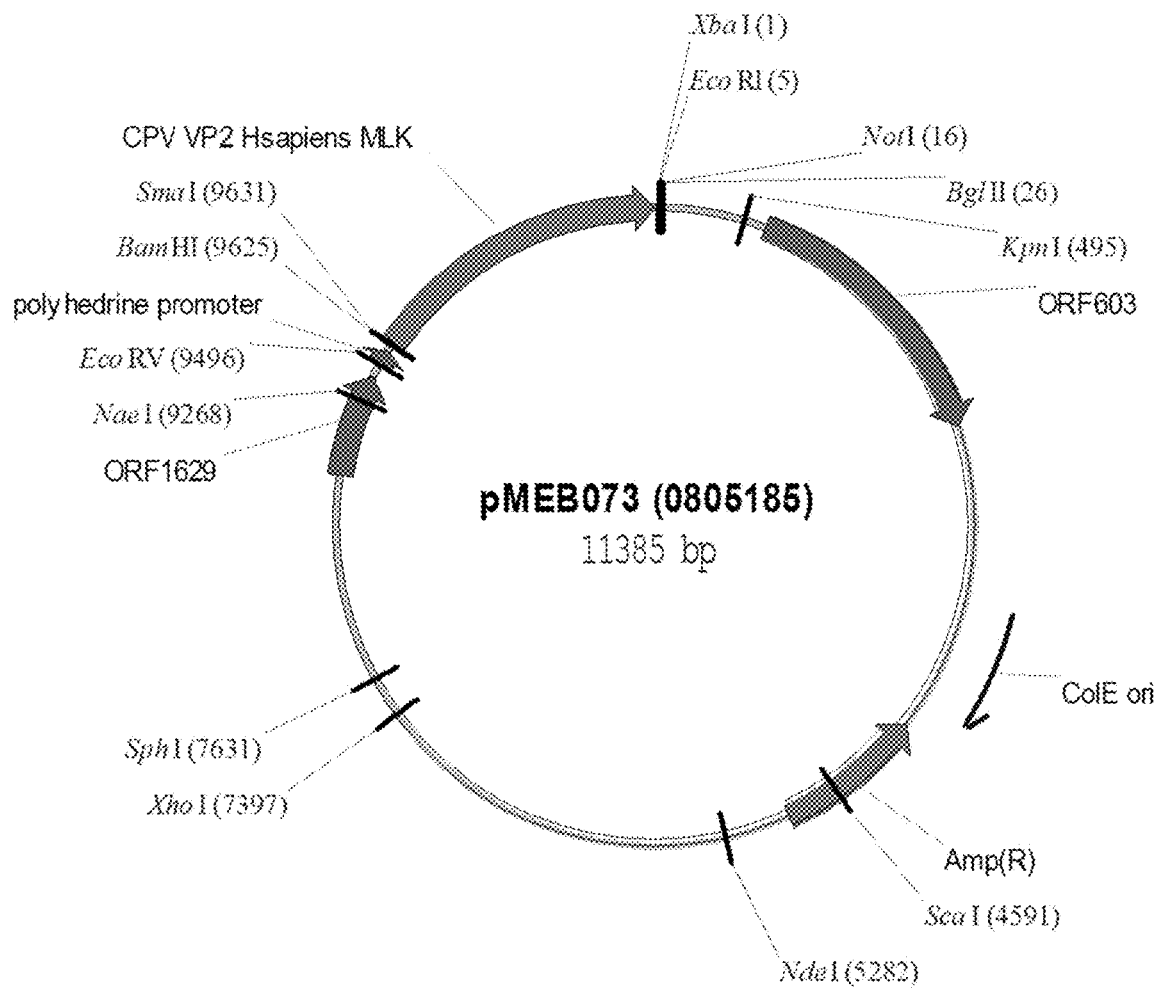
FIG. 3 depicts the plasmid map of pMEB073.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The antigenic polypeptides of the invention are capable of protecting against CPV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a CPV polypeptide. A polynucleotide encoding a fragment of a CPV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a CPV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are CPV antigenic polypeptides that are produced by a baculovirus expression vector in insect cells. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

In one aspect, the present invention provides CPV polypeptides from CPV isolates. In another aspect, the present invention provides a polypeptide having a sequence as set forth in SEQ ID NOs: 1, 3, 4, 6, 8-10, and variant or fragment thereof.

In another aspect, the invention relates to CPV empty capsids or CPV VLPs (virus-like particles). The capsids may comprise, consist essentially of, or consist of CPV VP2 polypeptides, or variants, including truncated versions thereof.

Moreover, homologs of CPV polypeptides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type CPV polypeptide can differ from the wild-type CPV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type CPV polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the CPV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for CPV polypeptides, the DNA sequence of the CPV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of CPV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the CPV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the CPV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to ovine, bovine, caprine and porcine vaccines or pharmaceutical or immunological compositions which may comprise an effective amount of a recombinant CPV antigens and a pharmaceutically or veterinarily acceptable carrier, adjuvant, excipient, or vehicle.

The subject matter described herein is directed in part, to compositions and methods related to the CPV antigen prepared in a baculovirus/insect cell expression system that was highly immunogenic and protected animals against challenge from homologous and heterologous CPV strains.

Compositions

The present invention relates to a CPV vaccine or composition which may comprise an effective amount of a recombinant CPV antigen and a pharmaceutically or veterinarily acceptable carrier, excipient, or vehicle. In one embodiment, the recombinant CPV antigen is expressed by a baculovirus expression vector in insect cells.

One embodiment of the invention relates to a vaccine or composition comprising CPV empty capsids or CPV VLPs (virus-like particles). The CPV empty capsids or CPV VLPs (virus-like particles) are obtained by expression of the CPV capsid protein.

The present invention also relates to processes for preparing these vaccines, the use of antigens for producing these vaccines and vaccination methods using them.

The present invention also relates to nucleotide sequences, in particular cDNA, and to amino acid sequences, modified compared with natural sequences of the virus. The invention also relates to the expression products of the modified nucleotide sequences and to the CPV antigens and virus incorporating these modifications.

The present invention encompasses any CPV polypeptide, antigen, epitope or immunogen that elicits an immunogenic response in an animal, such as an ovine, bovine, caprine or swine. The CPV polypeptide, antigen, epitope or immunogen may be any CPV polypeptide, antigen, epitope or immunogen, such as, but not limited to, a protein, peptide or fragment thereof, that elicits, induces or stimulates a response in an animal, such as canine.

In an embodiment wherein the CPV immunological composition or vaccine is a recombinant immunological composition or vaccine, the composition or vaccine comprising a recombinant vector and is non-adjuvanted, and may optionally comprise a pharmaceutical or veterinary acceptable excipient, carrier or vehicle; the recombinant vector is a baculovirus expression vector which may comprise a polynucleotide encoding a CPV polypeptide, antigen, epitope or immunogen. The CPV polypeptide, antigen, epitope or immunogen, may be capsid protein and any fragment thereof.

In one embodiment, the nucleic acid molecule encoding one or more CPV antigen(s) is a cDNA encoding a CPV capsid protein. In another embodiment, the nucleic acid molecule encoding one or more CPV antigen(s) is a cDNA encoding a fragment of the CPV capsid protein.

In another embodiment, the CPV antigen may be derived from CPV strain 100869-1.

The present invention relates to a CPV composition or vaccine which may comprise an effective amount of a recombinant CPV antigen. The CPV composition or vaccine does not contain an adjuvant. The CPV composition or vaccine may optionally contain a pharmaceutically or veterinarily acceptable carrier, excipient, or vehicle.

The invention further encompasses the CPV polynucleotides contained in a vector molecule or an expression vector and operably linked to a promoter element and optionally to an enhancer.

In one aspect, the present invention provides CPV polypeptides having a sequence as set forth in SEQ ID NO: 1, 3, 4, 6, or 8-10, and variants or fragments thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptides having a sequence as set forth in SEQ ID NO: 1, 3, 4, 6, or 8-10.

In yet another aspect, the present invention provides fragments and variants of the CPV polypeptides identified above (SEQ ID NO: 1, 3, 4, 6, or 8-10) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 1, 3, 4, 6, or 8-10.

An immunogenic fragment of a CPV polypeptide includes at least 8, 10, 15, or 20 consecutive amino acids, at least 21 amino acids, at least 23 amino acids, at least 25 amino acids, or at least 30 amino acids of a CPV polypeptide having a sequence as set forth in SEQ ID NO: 1, 3, 4, 6, or 8-10, or variants thereof. In another embodiment, a fragment of a CPV polypeptide includes a specific antigenic epitope found on a full-length CPV polypeptide. However, the skilled person will understand that a sufficient portion of the CPV polypeptide must be present to enable formation of CPV VLPs.

In another aspect, the present invention provides a polynucleotide encoding a CPV polypeptide, such as a polynucleotide encoding a polypeptide having a sequence as set forth in SEQ ID NO: 1, 3, 4, 6, or 8-10. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 4, 6, or 8-10, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO: 2, 5, 7, 11 or 12, or a variant thereof. In yet another aspect, the present invention provides a polynucleotide having at least 70%, at least 75%, at least 80%, at least 85%, at least 90%, at least 95%, at least 95%, 96%, 97%, 98%, or 99% sequence identity to one of a polynucleotide having a sequence as set forth in SEQ ID NO: 2, 5, 7, 11 or 12, or a variant thereof.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a CPV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a CPV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more CPV polypeptides, antigens, epitopes or immunogens. In one embodiment, the vector contains and expresses a polynucleotide that comprises, consists essentially of, or consists of a polynucleotide coding for (and advantageously expressing) a CPV antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a CPV polypeptide, antigen, epitope or immunogen, or a fragment thereof.

According to another embodiment, the vector or vectors in the preparation comprise, or consist essentially of, or consist of polynucleotide(s) encoding one or more proteins or fragment(s) thereof of a CPV polypeptide, antigen, epitope or immunogen, the vector or vectors expressing the polynucleotide(s). In another embodiment, the preparation comprises one, two, or more vectors comprising polynucleotides encoding and expressing, advantageously in vivo, a CPV polypeptide, antigen, fusion protein or an epitope thereof.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a CPV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter has either a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

The plasmids may comprise other expression control elements. It is particularly advantageous to incorporate stabilizing sequence(s), e.g., intron sequence(s), for example, maize alcohol dehydrogenase intron (Callis et al. Genes & Dev. 1(10):1183-1200, December 1987), the first intron of the hCMV-IE (PCT Application No. WO1989/01036), the intron II of the rabbit (3-globin gene (van Ooyen et al., 1979). In another embodiment, the plasmids may comprise 3' UTR. The 3' UTR may be, but not limited to,

*agrobacterium* nopaline synthase (Nos) 3' UTR (Nopaline synthase: transcript mapping and DNA sequence. Depicker, A. et al. J. Mol. Appl. Genet., 1982; Bevan, N A R, 1984, 12(22): 8711-8721).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant CPV antigen is expressed in insect cells.

In one particular embodiment, the CPV antigen is expressed in SF9 cells.

Methods of Use

In an embodiment, the subject matter disclosed herein is directed to a method of vaccinating an ovine, bovine, caprine, or swine comprising administering to the ovine, bovine, caprine, or swine an effective amount of a vaccine which may comprise an effective amount of a recombinant CPV antigen and a pharmaceutically or veterinarily acceptable carrier, excipient, or vehicle.

In one embodiment of the present invention, the method comprises a single administration of a vaccine composition formulated with an emulsion according to the invention. For example, in one embodiment, the immunological or vaccine composition comprises baculovirus expressed CPV antigens, including polypeptides and VLPs (virus-like particles) or empty capsids. Electron microscopy indicates the insect cells transformed with baculovirus expression vectors produce CPV VLPs or CPV empty capsids, and so immunological or vaccine compositions according to the instant invention encompass those comprising CPV VLPs or CPV empty capsids.

In an embodiment, the subject matter disclosed herein is directed to a method of vaccinating an ovine, bovine, caprine, or swine comprising administering to the ovine, bovine, caprine, or swine the CPV antigen produced by a baculovirus vector in insect cells.

In an embodiment, the subject matter disclosed herein is directed to a method of eliciting an immune response comprising administering to the ovine, bovine, caprine, or swine a vaccine comprising the CPV antigen produced by a baculovirus vector in insect cells.

In an embodiment, the subject matter disclosed herein is directed to a method of preparing a vaccine or composition comprising isolating a CPV antigen produced by a baculovirus vector in insect cells and optionally combining with a pharmaceutically or veterinarily acceptable carrier, excipient or vehicle.

Both homologous and heterologous CPV strains are used for challenge to test the efficacy of the vaccine. The administering may be subcutaneously or intramuscularly. The administering may be needle free (for example, Bioject).

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the boost. This administration protocol is called "prime-boost".

A prime-boost according to the present invention can include a recombinant viral vector is used to express a CPV coding sequence or fragments thereof encoding an antigenic polypeptide or fragment or variant thereof. Specifically, the viral vector can express a CPV gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941, 5,494,807), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The CPV antigen of the invention to be expressed is inserted under the control of a specific poxvirus promoter, e.g., the entomopoxvirus *Amsacta moorei* 42K promoter (Barcena, Lorenzo et al. 2000), the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In another aspect of the prime-boost protocol of the invention, a composition comprising the CPV antigen of the invention is administered followed by the administration of vaccine or composition comprising a recombinant viral vector that contains and expresses the CPV antigen in vivo, or an inactivated viral vaccine or composition comprising the CPV antigen, or a DNA plasmid vaccine or composition that contains or expresses the CPV antigen. Likewise, a prime-boost protocol may comprise the administration of vaccine or composition comprising a recombinant viral vector that contains and expresses a CPV antigen in vivo, or an inactivated viral vaccine or composition comprising a CPV antigen, or a DNA plasmid vaccine or composition that contains or expresses a CPV antigen, followed by the administration of a composition comprising the CPV antigen of the invention. It is further noted that both the primary and the secondary administrations may comprise the composition comprising the CPV antigen of the invention.

A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as feline or canine, with a virulent strain of CPV.

Further details of these CPV strains may be found on the European Bioinformatics Information (EMBL-EBI) web pages, and all of the associated nucleotide sequences are herein incorporated by reference. The inventors contemplate that all CPV strains, both herein listed, and those yet to be identified, could be expressed according to the teachings of the present disclosure to produce, for example, effective vaccine compositions. Both homologous and heterologous strains are used for challenge to test the efficacy of the vaccines. The animal may be challenged intradermally, subcutaneously, spray, intra-nasally, intra-ocularly, intra-tracheally, and/or orally.

The prime-boost administrations may be advantageously carried out 1 to 6 weeks apart, for example, about 4 weeks apart. According to one embodiment, a semi-annual booster or an annual booster, advantageously using the viral vector-based vaccine, is also envisaged. The animals are advantageously at least 6 to 8 weeks old at the time of the first administration.

The compositions comprising the recombinant antigenic polypeptides of the invention used in the prime-boost protocols are not adjuvanted, and may optionally be contained in a pharmaceutically or veterinary acceptable vehicle, diluent or excipient. The protocols of the invention protect the animal from CPV and/or prevent disease progression in an infected animal.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the invention provides for the administration of a therapeutically effective amount of a formulation for the delivery and expression of a CPV antigen or epitope in a target cell. Determination of the therapeutically effective amount is routine experimentation for one of ordinary skill in the art. In one embodiment, the formulation comprises an expression vector comprising a polynucleotide that expresses a CPV antigen or epitope and a pharmaceutically or veterinarily acceptable carrier, vehicle or excipient. In another embodiment, the pharmaceutically or veterinarily acceptable carrier, vehicle or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals (DIVA).

It is disclosed herein that the use of the vaccine or composition of the present invention allows the detection of CPV infection in an animal. It is disclosed herein that the use of the vaccine or composition of the present invention allows the detection of the infection in animals by differentiating between infected and vaccinated animals (DIVA).

Article of Manufacture

In an embodiment, the subject matter disclosed herein is directed to a kit for performing a method of eliciting or inducing an immune response which may comprise any one of the recombinant CPV immunological compositions or vaccines, or inactivated CPV immunological compositions or vaccines, recombinant CPV viral compositions or vaccines, and instructions for performing the method.

Another embodiment of the invention is a kit for performing a method of inducing an immunological or protective response against CPV in an animal comprising a composition or vaccine comprising a CPV antigen of the invention and a recombinant CPV viral immunological composition or vaccine, and instructions for performing the method of delivery in an effective amount for eliciting an immune response in the animal.

Another embodiment of the invention is a kit for performing a method of inducing an immunological or protective response against CPV in an animal comprising a composition or vaccine comprising a CPV antigen of the invention and an inactivated CPV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional primo-vaccinations or additional boost-vaccinations.

The following embodiments are encompassed by the invention. In an embodiment, a composition comprising a CPV antigen or fragment or variant thereof and a pharmaceutical or veterinarily acceptable carrier, excipient, or vehicle is disclosed. In another embodiment, the composition described above wherein the CPV antigen or fragment or variant thereof comprises an immunogenic fragment comprising at least 15 amino acids of a CPV antigen is disclosed. In an embodiment, the above compositions wherein the CPV antigen or fragment or variant thereof is partially purified are disclosed. In an embodiment, the above compositions wherein the CPV antigen or fragment or variant thereof is substantially purified are disclosed.

In an embodiment, the above compositions wherein the CPV antigen or fragment or variant thereof is a CPV polypeptide are disclosed. In an embodiment, the above compositions wherein the CPV polypeptide is a capsid protein or a fragment thereof are disclosed. In an embodiment, the above compositions wherein the CPV antigen or fragment or variant thereof has at least 80% sequence identity to the sequence as set forth in SEQ ID NO: 1, 3, 4, 6, or 8-10 are disclosed. In one embodiment, the above compositions wherein the CPV antigen is encoded by a polynucleotide having at least 70% sequence identity to the sequence as set forth in SEQ ID NO: 2, 5, 7, 11 or 12 are disclosed. In another embodiment, a method of vaccinating an animal susceptible to CPV comprising administering the compositions above to the animal is disclosed. In an embodiment, a method of vaccinating an animal susceptible to CPV comprising a prime-boost regime is disclosed. In an embodiment, a substantially purified antigenic polypeptide expressed in insect cells, wherein the polypeptide comprises: an amino acid sequence having at least 80% sequence identity to a polypeptide having the sequence as set forth in SEQ ID NO: 1, 3, 4, 6, or 8-10 is disclosed. In any embodiment the animal is preferably a feline or canine. In one embodiment, a method of diagnosing CPV infection in an animal is disclosed. In yet another embodiment, a kit for prime-boost vaccination comprising at least two vials, wherein a first vial containing the composition of the present invention, and a second vial containing a composition for the boost-vaccination comprising a composition comprising a recombinant viral vector, or a composition comprising an inactivated viral composition, or a DNA plasmid composition that contains or expresses the CPV antigen is disclosed.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

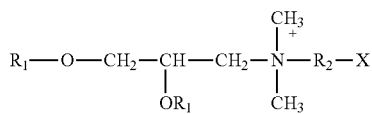

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

In another embodiment, pharmaceutically or veterinarily acceptable carrier, excipient, adjuvant, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

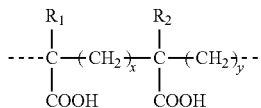

in which: R1 and R2, which can be the same or different, represent H or CH3; x=0 or 1, preferably x=1; y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with a carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), polyinosinic and polycytidylic acid, cytidine-phosphate-guanosine oligodeoxynucleotides (CpG ODN), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a bovine cytokine for preparations to be administered to bovines).

In the case of immunological composition and/or vaccine based on a baculovirus/insect cell-expressed polypeptides, a dose may include, about 1 μg to about 2000 μg, about 50 μg to about 1000 μg, and from about 100 μg to about 500 μg of CPV antigen, epitope or immunogen. The dose may include about $10^2$ to about $10^{20}$ VLPs, about $10^3$ to about $10^{20}$, about 104 to about $10^{20}$. The dose volumes can be between about 0.1 and about 10 ml, between about 0.2 and about 5 ml. In general, the skilled person is aware of many dosing strategies, and will be able to optimize dosing without the exercise of non-routing work.

In an aspect, the invention provides a combination vaccine comprising a virus-like particle (VLP) component and a modified-live virus (MLV) component, wherein both the VLP and the MLV are directed against the same pathogen or disease, and wherein the combination vaccine overcomes maternally-derived antibodies (MDA).

In some embodiments, the combination vaccine provides protective immunity with a single dose.

In some embodiments, the pathogen or disease is canine parvovirus (CPV).

In some embodiments, the pathogen or disease is foot-and-mouth disease virus (FMDV).

In some embodiments, the VLP component of the combination comprises at least at least 10% CPV VLPs (w/w) as a function of total protein content.

In some embodiments, the VLP component comprises at least 20% CPV VLPs (w/w).

In some embodiments, the CPV VLP is expressed by a baculovirus vector in insect cells.

In some embodiments, the CPV VLP comprises at least one CPV capsid protein.

In some embodiments, the CPV VLP comprises a CPV polypeptide having the sequence as set forth in SEQ ID NO: 1, 3, 4, 6, 8, 9 or 10; or, the CPV VLP comprises a CPV polypeptide having at least 90% identity a sequence as set forth in SEQ ID NO: 1, 3, 4, 6, 8, 9 or 10.

In some embodiments, the CPV VLP comprises a CPV polypeptide encoded by a polynucleotide having the sequence as set forth in SEQ ID NO: 2, 5 or 7; or, the CPV VLP comprises a CPV polypeptide encoded by a polynucleotide having at least 90% identity to a sequence as set forth in SEQ ID NO: 2, 5 or 7.

In some embodiments, the combination vaccine is not adjuvanted and optionally comprises a pharmaceutically or veterinarily acceptable carrier, excipient, or vehicle.

In another aspect, the invention provides a plasmid useful for producing CPV VLP, comprising a polynucleotide encoding a CPV antigen having a sequence as set forth in SEQ ID NO: 1, 3, 4, 6, or 8-10, or a polynucleotide sequence having at least 90% identity to a sequence as set forth in SEQ ID NO: 1, 3, 4, 6, or 8-10.

In some embodiments, the polynucleotide comprises or consists of the sequence as set forth in SEQ ID NO: 2, 5, 7, 11 or 12.

In some embodiments, the plasmid consists of the sequence as set forth in SEQ ID NO:11 or 12.

In some embodiments, the plasmid is stably transformed into an insect cell, which expresses CPV VLPs.

In another aspect, the invention provides a substantially purified CPV empty capsid or CPV VLP expressed in insect cells, wherein the CPV empty capsid or VLP comprises a polypeptide having a sequence as set forth in SEQ ID NO: 1, 3, 4, 6, or 8-10; or, the CPV empty capsid or VLP comprises a polypeptide having at least 90% identity to a sequence as set forth in SEQ ID NO: 1, 3, 4, 6, or 8-10.

In some embodiments, the CPV empty capsid or VLP consists of a polypeptide having a sequence as set forth in SEQ ID NO: 1, 3, 4, 6, or 8-10.

In another aspect, the invention provides a method of eliciting an immune response in an animal against CPV comprising administering to the animal the compositions, vaccines, combination vaccines and VLPS disclosed herein.

In some embodiments, the immune response protects vaccinates against subsequent exposure to virulent CPV. The exposure may be natural or experimental.

In some embodiments, the immune response is elicited in the vaccinated animals regardless of the presence in said animals of high levels of maternally-derived antibodies (MDA) against CPV. "High levels" has the ordinary meaning, and generally refers to levels of MDA that impede the ability of prior art vaccines to elicit a strong protective response in MDA-positive animals.

The invention will now be further described by way of the following non-limiting examples.

EXAMPLES

Unless otherwise described, construction of DNA inserts, plasmids and recombinant viral or baculovirus vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Construction and Expression of CPV Capsid Antigens in Baculovirus/Insect Cells System Objective: Generate a pVL1393-based transfer plasmid encoding the CPV capsid protein of CPV (canine parvovirus, strain Souriou serotype 2c) optimized for insect cells and generation of the recombinant baculovirus BacMEB072 in order to express virus like particles (VLP). The reference sequence was strain Souriou 2c (Merial), having the designation Genbank BAD34656/Swissprot P61826 (SEQ ID NO: 1).

The CPV capsid gene (1755 bp) encodes a 584 amino acid polypeptide (containing no signal peptide). The sequence encoding the CPV VP2 protein (SEQ ID NO: 1) was cloned and the corresponding DNA sequence was codon-optimized (SEQ ID NO: 5) for insect cells. Potential functional domains are shown in Table 1 below.

TABLE 1

Potential functional domains are the following (according to Swiss-prot annotation on P61826)

| Putative domains | From to (or position) | Length |
|---|---|---|
| Signal sequence | no | |
| mature chain VP2 | 1-584 | 584 |
| N-glycosylation | 25-47-64-180-443-505-517 | |
| N-glycosylation sites | 490-494 | |

Generation of Plasmid pMEB072.

The CPV capsid optimized for insect expression (SEQ ID NO: 1) was cloned into commercial plasmid pVL1393 (Pharmingen) using the XbaI and Bam HI sites of both the vector and insert to generate the expression plasmid pMEB072.

Generation of Recombinant Baculovirus BacMEB072.

The baculovirus vector used was AcNPV modified by a lethal deletion that is only rescued through homologous recombination (BaculoGold DNA, Pharmingen). Plasmid pMEB072 was used to generate a recombinant baculovirus, encoding CPV capsid gene strain Souriou serotype 2c under control of polyhedrin promoter, by homologous recombination. *Spodoptera frugiperda* (Sf) 9 insect cells were co-transfected with plasmid pMEB072 and Bsu36I triple-cut linearized AcNPV DNA, according to manufacturer's protocol (Baculogold, Pharmingen). Recombinant baculovirus from co-transfection supernatant were plaque purified twice. Five clones were amplified (passage 1) at 28° C. at a 25 cm² monolayer flask scale. Infected cells and supernatants were analysed for CPV capsid expression by Dot Blot using monoclonals specific of CPV capsid antigen (CPV103B10A). Clone 1 showed a correct Dot Blot profile. This clone was further amplified (passage 2) at 28° C. at a 50 mL scale in Erlenmeyer (suspension) at 105 rpm. A third passage (passage 3) at a 200 mL scale was performed to obtain virus stock used for protein expression. This virus stock was then titrated by plaque assay. Virus stock was obtained using SF900II media, supplemented with 2% of FCS. After titration recombinant baculovirus stock (Passage 3) was used for protein production in serum free medium.

Expression Analysis of Baculovirus BacMEB072

TABLE 2

| Plasmid | Size (AA) | PM (kDa) | Signal peptide | Tag | N-glycosylation | Disulfide bridge | location |
|---|---|---|---|---|---|---|---|
| pMEB062 | 545 | 59.2 | no | no | 10 potential sites | No | secretion |

Insect cells (Sf9) were infected with BacMEB072 at a Multiplicity Of Infection (MOI) of 1 pfu/ml. Insect cells were grown at 105 rpm in Sf900II medium without FCS for 4 days at 28° C. Protein production was analyzed by submitting whole Sf9 lysates and culture supernatant to SDS-PAGE (4-20%, Invitrogen), followed by Dot Blot with monoclonal antibody (CPV103B10A). The solubility of the expressed proteins was studied by lysing the cellular pellets in lysis buffer (50 mM Tris-Hcl pH8, 500 mM NaCl+anti protease), sonication 3× (15 sec at 20% power, 30 sec wait, 15 sec at 20% power; 5 min lysis on ice). Soluble proteins were separated from the insoluble material by centrifugation (30 min at 11,000 rcf at 4° C.).

A band at expected size was expressed in the cell pellet of infected cells lysed and clarified as observed by coomassie staining. The protein accumulated in cells, but was also detected in the soluble fraction after lysis. The identity of VP2 protein was confirmed by Dot Blot using specific monoclonal antibody against CPV capsid (CPV103B10A).

Figure 4:
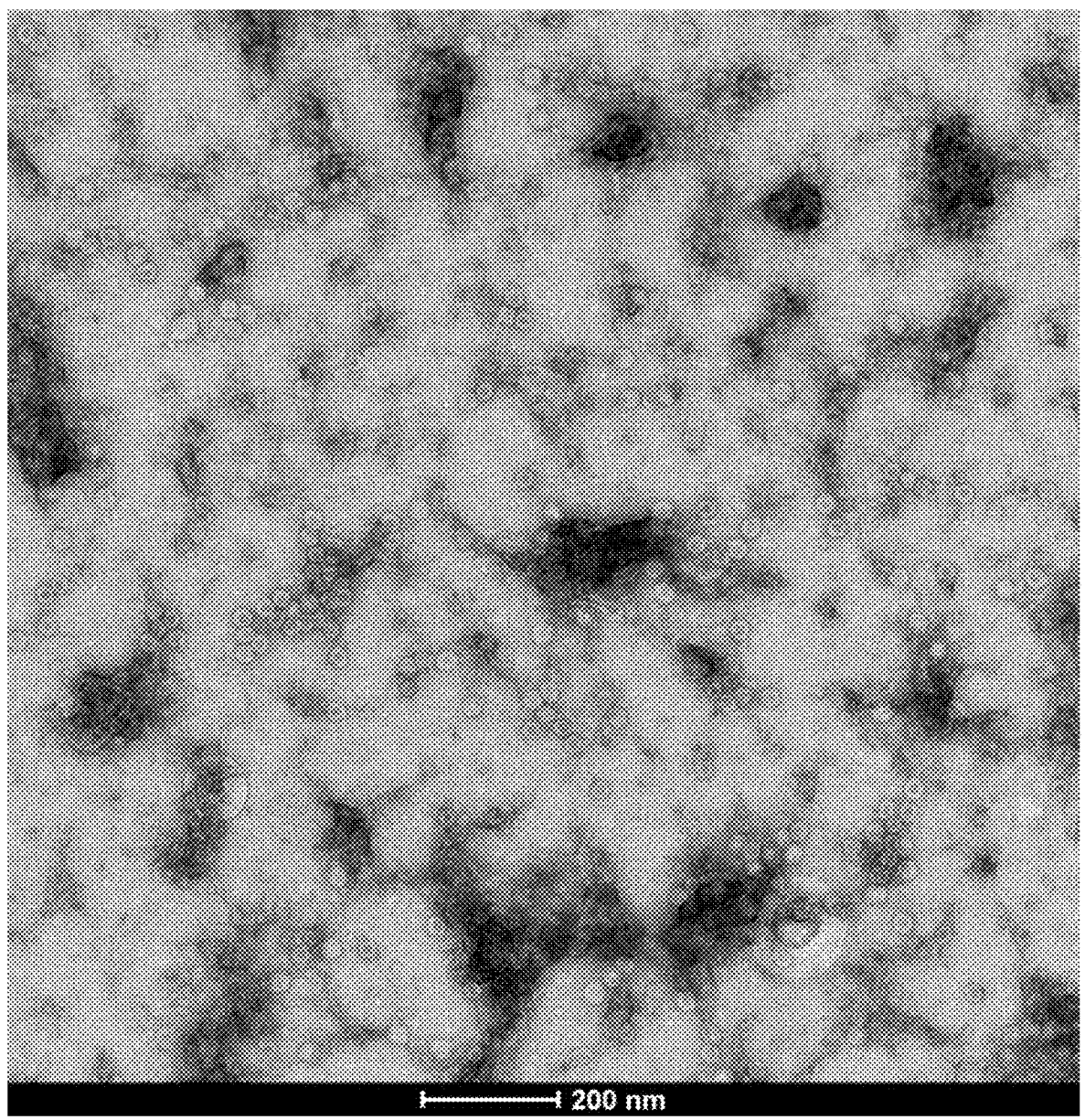
FIG. 4 is an electron micrograph of CPV VLPs, showing the correct shape and morphology for parvovirus-like virions.
Figure 5:
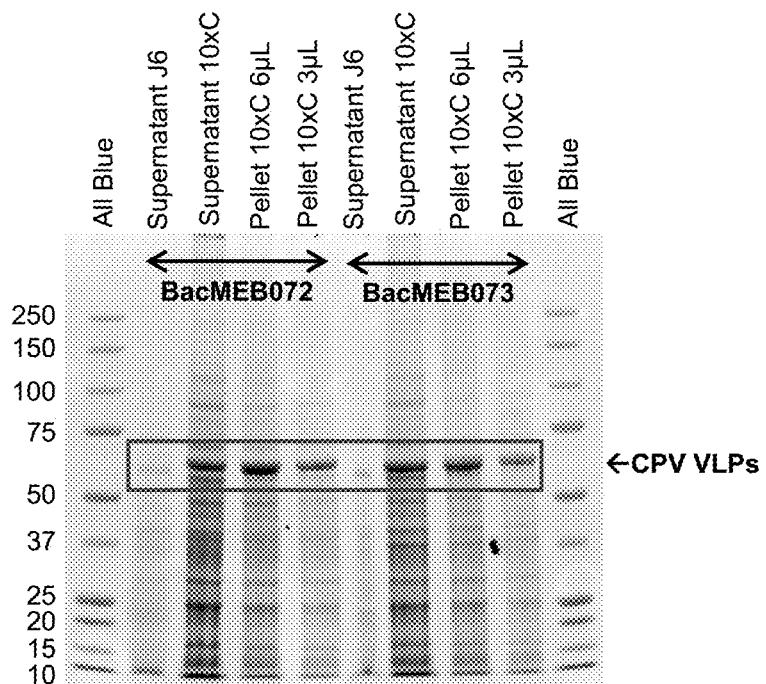
FIG. 5 is a Western Blot showing levels of CPV VLPs and accompanying data.

The electronic microscopy (EM) analysis confirmed correct auto-assembly of the capsid protein into VLPs, which had a diameter of 25-30 nm, and a correct morphology of parvovirus-like virions (FIG. 4). The optimal conditions for VLP production were to use MOI=0.1 and to harvest at 5 days post-infection. Although other conditions are envisioned, these particular conditions yielded a concentration of about $10^{11}$ VLPs per ml.

Example 2—Production of BacMEB073 Containing Truncated CPV VP2

The objective was to generate a pVL1393-based transfer plasmid encoding the truncated VP2 capsid protein of CPV (canine parvovirus, strain Souriou serotype 2c) optimized for mammals, and then to generate the corresponding recombinant baculovirus BacMEB073, expressing the VLP. The 9 N-terminal amino acids (−9AA) were deleted in an effort to enhance VP2 expression without preventing VLP formation (Hurtado et al. Journal of Virology, August 1996). In addition, three amino acids were added (M, L and K) in an effort to improve capsid structure and formation (Gilbert et al., Journal of Nanobiotechnology, 2006). Prior to this disclosure, it was unknown what effect the introduction of both the deletion and the insertions would have on CPV VP2 expression and subsequent capsid formation.

The truncated VP2 gene (deletion of 9 amino acids in the N-terminal replaced by additional MLK) and optimized for mammals (Geneart) was further cloned into plasmid pVL1393 using the Bam HI and Xba I sites of both the vector and insert.

Baculovirus vector generation and protein expression. Baculovirus vector: AcNPV modified by a lethal deletion which is only rescued through homologous recombination (BaculoGold DNA, Pharmingen).

Generation of Recombinant Baculovirus BacMEB073.

Plasmid pMEB073 was used to generate a recombinant baculovirus, encoding truncated CPV capsid gene of strain Souriou serotype 2c under control of polyhedrin promoter, by homologous recombination. *Spodoptera frugiperda* (Sf) 9 insect cells were co-transfected with plasmid pMEB073 and Bsu36I triple-cut linearized AcNPV DNA, according to manufacturer's protocol (Baculogold, Pharmingen). Recombinant baculovirus from co-transfection supernatant were plaque purified twice. Five clones were amplified (passage 1) at 28° C. at a 25 cm² monolayer flask scale. Infected cells and supernatants were analysed for CPV capsid expression by Dot Blot using monoclonals specific of CPV capsid antigen (CPV103B10A). Clone 1 showed a correct Dot Blot profile. This clone was further amplified (passage 2) at 28° C. at a 50 mL scale in Erlenmeyer (suspension) at 105 rpm. A third passage (passage 3) at a 200 mL scale was performed to obtain virus stock used for protein expression. This virus stock was then titrated by plaque assay. Virus stock was obtained using SF900II media, supplemented with 2% of FCS.

After titration recombinant baculovirus stock (Passage 3) was used for protein production in serum free medium.

Expression Analysis

TABLE 3

| | | | | Expected recombinants | | |
|---|---|---|---|---|---|---|
| Plasmid | Size (AA) | PM (kDa) | signal peptide | N-Glycosylation site | Disulfide bridge | Sub-cellular location |
| pMEB073 | 578 | 64.1 | no | 11, 19, 40, 50, 58, 66, 72, 79, 80, 511 | no | secreted |

Insect cells (Sf9) were infected with BacMEB073 at MOI=1 pfu/ml. Insect cells were grown at 105 rpm in Sf900II medium without FCS during 4 days at 28° C. Protein production was analyzed by submitting whole Sf9 lysates and culture supernatant to SDS-PAGE (4-20%, Invitrogen) followed by Dot Blot with monoclonal antibody (CPV103B10A).

The solubility of the expressed proteins was studied by lysing the cellular pellets in lysis buffer (50 mM Tris-Hcl pH8, 500 mM NaCl+anti protease), sonication 3× (15" at 20% of potency, 30" wait, 15" at 20% potency, 5' break on ice). Soluble proteins were separated from the insoluble material by centrifugation (30' min at 11 000 rcf at 4° C.).

Results and conclusion. A band at expected size of 64 kDa is expressed in the cell pellet of infected cells lysed and clarified as observed by coomassie staining. The protein accumulated in cells, but was detectable in the soluble fraction after lysis. The identity of VP2 protein was confirmed by Dot Blot using a specific CPV capsid mAb (CPV103B10A).

EM analysis confirmed auto-assembly of the capsid protein into VLPs with a diameter of 25-30 nm, as well as a correct morphology of parvovirus—like virions at a concentration of $10^{12}$ VLPs per ml (FIG. 4). VLP production was optimal at MOI=0.1 with harvest 5 days post infection, although other conditions may also yield high levels of VLP.

Example 3 Vaccination of Canines with Baculovirus Expressed CPV Capsid Protein

The primary objective of the study was to assess and compare the safety and immunogenicity of 2 Virus Like Particles (VLPs) of the CPV2c strain Souriou in puppies (i.e. BacMEB072 and BacMEB073, described in Examples 1 and 2). A secondary objective was to assess the adjuvant effects of aluminium hydroxide/saponin or iscomatrix on the immunogenicity of the VLPs produced by BacMEB072 and BacMEB073. Eight week-old puppies were vaccinated and surveyed as indicated in Table 4.

TABLE 4

Experimental design for truncated CPV VP2 VLP v. Full length CPV VP2 MLV study

| Group | Antigen: VLP CPV2 | Adjuvant | Vaccination | Clinical monitoring | Sera | Whole blood (sodium heparin) |
|---|---|---|---|---|---|---|
| A (n = 6) | BacME073 (truncated) | None | D0 & D28 by SC with 1 ml containing 25 μg of active ingredient | D0, D0+4-6 h, D1, D2 D28, D28+4-6 h, D29, D30 | D-7, D0*, D7, D28, D35, D42, D70 | D35, D42 |
| B (n = 6) | BacME073 (truncated) | Gel Al(OH)$_3$ (1.7 mg) + Saponin (12 haemolytic units) | | | | |
| C (n = 6) | BacME072 (non-truncated) | None | | | | |
| D (n = 6) | BacME072 (non-truncated) | Gel Al(OH)$_3$ (1.7 mg) + Saponin (12 haemolytic units) | | | | |
| E (n = 6) | BacME072 (non-truncated) | Iscomatrix (75 μg) | | | | |
| F (n = 5) | | Control | Control | | | |

*before vaccination

In terms of safety, Al(OH)$_3$/Saponin induced no general reactions nor any other signs except local heat and swellings. Mild swelling was observed for 3 to 4 days after each vaccination in most of the dogs. Iscomatrix appears to be a very safe adjuvant. In terms of immunogenicity, vaccination of puppies with VLP CPV2 was able to induce both humoral and cellular immune response with no major differences between truncated or full length VP2 associated in VLPs. Notably, the persistence of humoral immune response was increased when VLPs were adjuvanted either with Al(OH)$_3$/Saponin or with Iscomatrix with no significant difference between the two adjuvants investigated. Moreover, Iscomatrix adjuvant increased the magnitude of IFN gamma response not only compared to the non-adjuvanted group but also to Al(OH)$_3$ and Saponin group.

Example 4 Vaccination of Canines with Baculovirus Expressed CPV VLPs or MLV CPV (Strains Souriou or Bari)

Figures 7, 8:
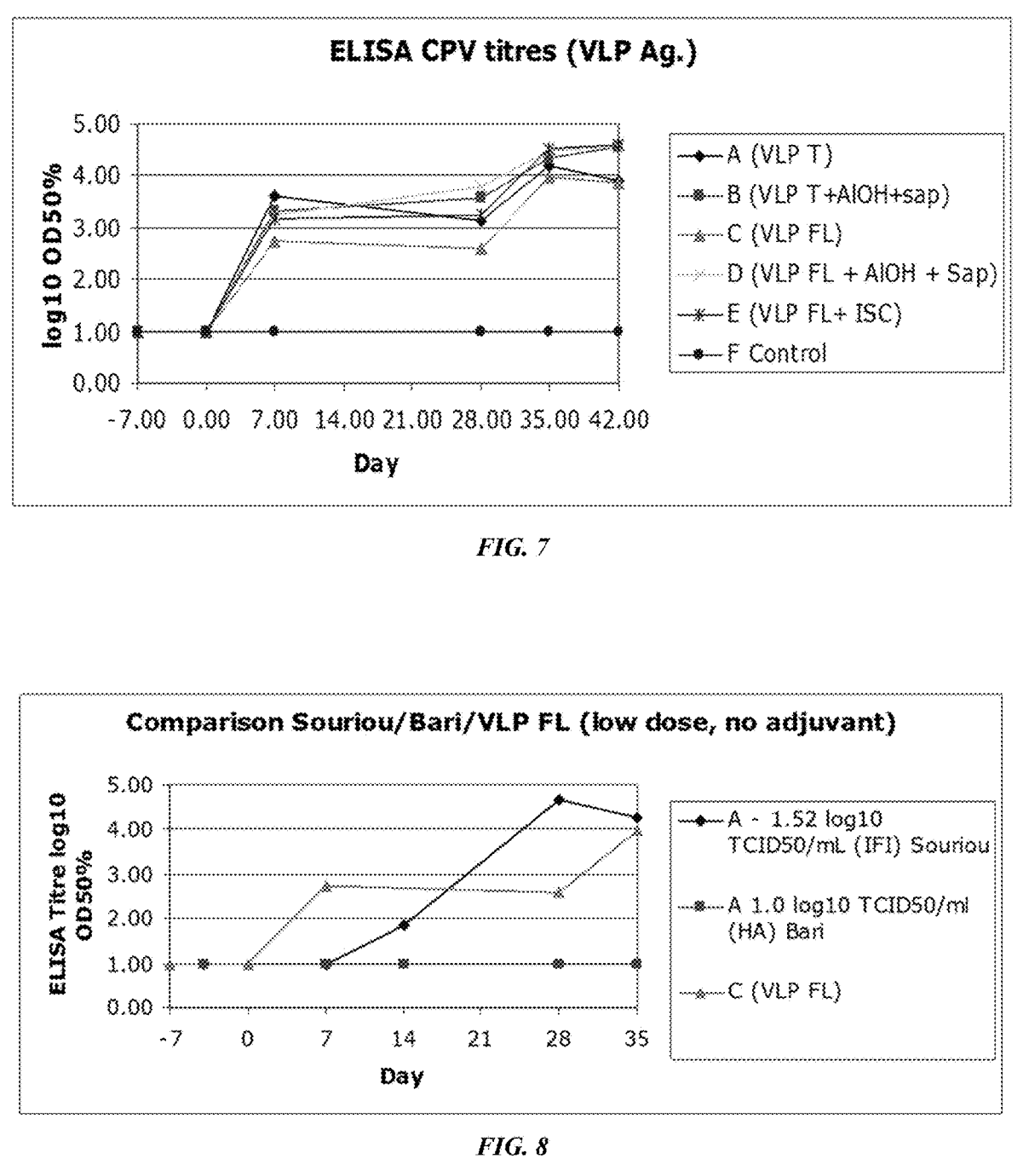
Figure 9:
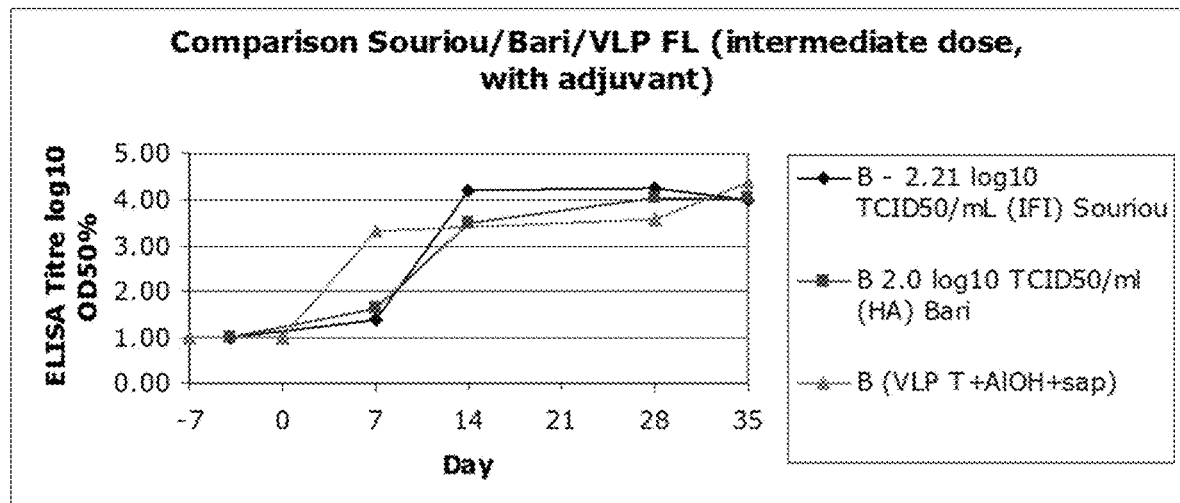
Figure 10:
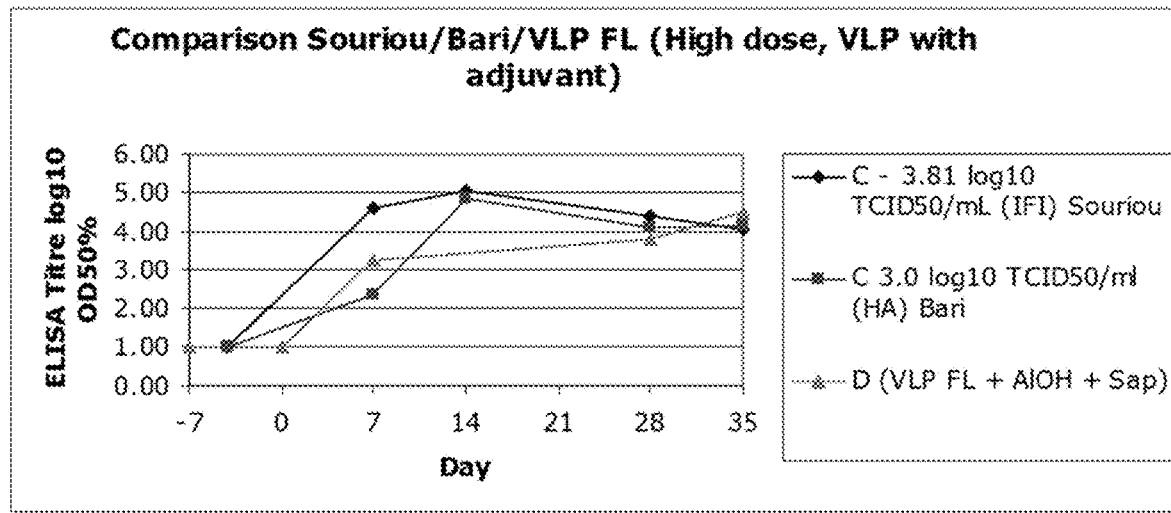

The objective of the study was to compare the immune response in puppies vaccinated with CPV VLP, Souriou CPV MLV or Bari CPV MLV. The first experiment compared 1.52 log 10 TCID50/mL (IFI) Souriou; 1.0 log 10 TCID50/mL (HA) Bari; and pMEB072 VLP (results in FIG. 8). The second experiment compared 2.21 log 10 TCID50/mL (IFI) Souriou; 2.0 log 10 TCID50/mL (HA) Bari; and pMEB073-produced VLP in Al(OH)$_3$+saponin adjuvant (results in FIG. 9). Finally, the third experiment compared 3.81 log 10 TCID50/mL (IFI) Souriou; 3.0 log 10 TCID50/mL (HA) Bari; and pMEB072-produced VLP in Al(OH)$_3$+saponin adjuvant (results in FIG. 10). Taken together, these results showed that CPV VLP, made according to the instant disclosure, provided a comparable immune response when compared to exemplar CPV MLV. Importantly, the VLPs were able to induce a more rapid immune response when compared to both the low and intermediate doses of either MLV strain.

Example 5 Vaccination of Canines with CPV MLV or Baculovirus-Expressed CPV Capsid Protein+MLV CPV The objective of the study was to evaluate the immunogenicity of different vaccine candidates administered at different doses and subcutaneously in puppies with maternal antibodies. Prior to this study, it was not known whether CPV VLP could overcome maternal antibodies to induce protective immunity in puppies.

TABLE 5

Experimental design for CPV VLP v. CPV MLV study

| Group | Vaccine administered SC on Day 0 | Blood Sample (6 mL/puppy) | Analysis |
|---|---|---|---|
| A CPV MLV (n = 9) | CPV2 MLV 5.5log10 (1 ml) | D0*, D7, D14, D21, D28, D34, D42, D56 | Anti-CPV Antibody Determination (Hemagglutination Inhibition and/or ELISA) |
| B CPV VLP + CPV MLV (n = 10) | CPV VLP Target dose: 500 μg (1 ml) + CPV2 MLV 5.5log10 (1 ml) | | |

Figure 12:
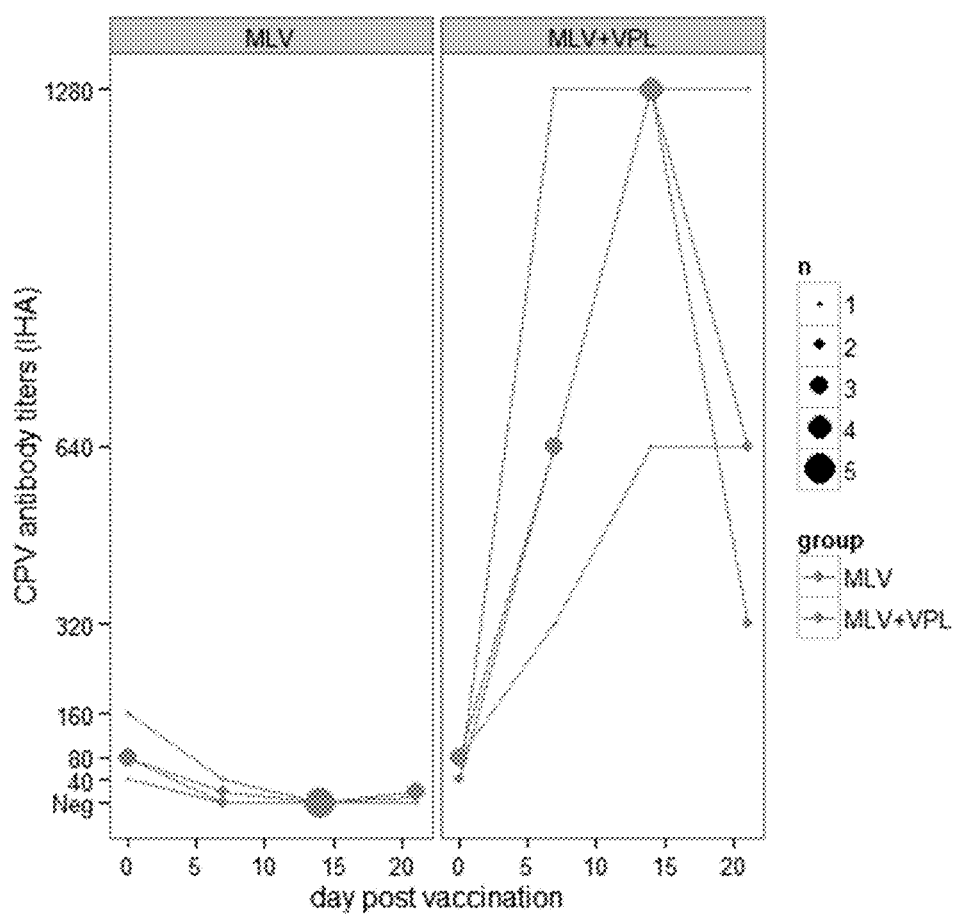

As indicated in FIG. 11, FIG. 12 and Table 6, CPV antibody titers were significantly higher in the MLV+VLP group. These data indicate that the addition of CPV VLP to the vaccine formulation was sufficient to overcome the maternal antibodies, a surprising and unexpected result. The inventors envision that VLP are capturing a significant proportion of circulating CPV MDA which in turn allows the VLP and CPV MLV to actively immunize puppies.

TABLE 6

Anti-CPV antibody titers (IHA) according to days post vaccination

| Group | ID | 0 | 7 | 14 | 21 |
|---|---|---|---|---|---|
| MLV | 2252826 | 10 | <5 | 2560 | 320 |
| MLV | 2253001 | 10 | <5 | 1280 | <5 |
| MLV | 2284928 | 80 | <5 | <5 | <5 |
| MLV | 2284973 | 80 | 20 | <5 | 20 |
| MLV | 2284975 | 80 | 20 | <5 | 10 |
| MLV | 2285160 | <5 | <5 | <5 | 5 |
| MLV | 2285360 | 160 | 40 | <5 | 20 |
| MLV | 2285367 | 40 | <5 | <5 | 20 |
| MLV | 2285387 | 10 | 5 | <5 | <5 |
| MLV + VLP | 2252827 | 80 | 640 | 1280 | 320 |
| MLV + VLP | 2252828 | 5 | 160 | 5120 | 2560 |
| MLV + VLP | 2284818 | 10 | 640 | 2560 | 2560 |
| MLV + VLP | 2284843 | 10 | 640 | 2560 | 1280 |
| MLV + VLP | 2284861 | 20 | 1280 | 1280 | 1280 |
| MLV + VLP | 2284935 | 40 | 640 | 1280 | 320 |
| MLV + VLP | 2284941 | 80 | 640 | 1280 | 640 |
| MLV + VLP | 2284943 | 20 | 320 | 1280 | 1280 |
| MLV + VLP | 2284978 | 40 | 1280 | 1280 | 1280 |
| MLV + VLP | 2285000 | 80 | 320 | 640 | 640 |

MLV: Modified Live Vaccine (PRIMODOG ® 5.5log10/ml)
VLP: Virus Like Particle, 500 µg

Example 6 Vaccination of Canines with Baculovirus-Expressed CPV Capsid Protein, MLV CPV or Adenovirus-Vectored CDV The objective of the study was to evaluate the immunogenicity of several doses of different vaccine candidates administered via different routes. The different candidates were CPV VLP, and recombinant adenoviruses expressing either CPV or CDV (canine distemper) genes.

TABLE 7

Experimental design for CPV VLP v. Adeno CPV v. Adeno CDV study

| Group | Vaccine administered at D0 and D28** Dose and Route | Samples Taken | Analyses | |
|---|---|---|---|---|
| A VLP+_1 (n = 6) | VLP CPV High dose | Blood vials: D0, D7, D14, D21, D28, D35, D42, D56 and D63 | Determination of anti-CDV antibodies (ELISA and/or Hemagglutination Inhibition) | Cellular and/or B Memory Cell Immune Response |
| B VLP+_2 (n = 6) | (500 µl stock solution/dose) SC (1 mL) | | | |
| C VLP-** (n = 6) | VLP CPV Low dose (50 µl stock solution/dose) SC (1 mL) | Heparin blood vials: D7, D31, D35, D56 | | |
| D VLP_Oral (n = 6) | VLP CPV 2 ml undiluted stock solution Oral | | | |
| E Ad5_CPV+ (n = 6) | Adeno CPV vAD3032 high dose target dose (8.64 log 10 TCID50/mL*) SC (1 mL) | | | |
| F Ad5_CPV (n = 6) | Adeno CPV vAD3032 low dose (target dose 7.64 log 10 TCID50/mL*) SC (1 mL) | | | |
| G Ad5_CDV- (n = 6) | Adeno CDV vAD3031 low dose (target dose 7.34 log 10 TCID50/mL*) SC (1 mL) | | Determination of anti-CDV antibodies (Seroneutralization) | |
| H Ad5_CDV+ (n = 6) | Adeno CDV vAD3031 high dose (target dose 8.34 log 10 TCID50/mL*) SC (1 ml) | | | |

Figure 13:
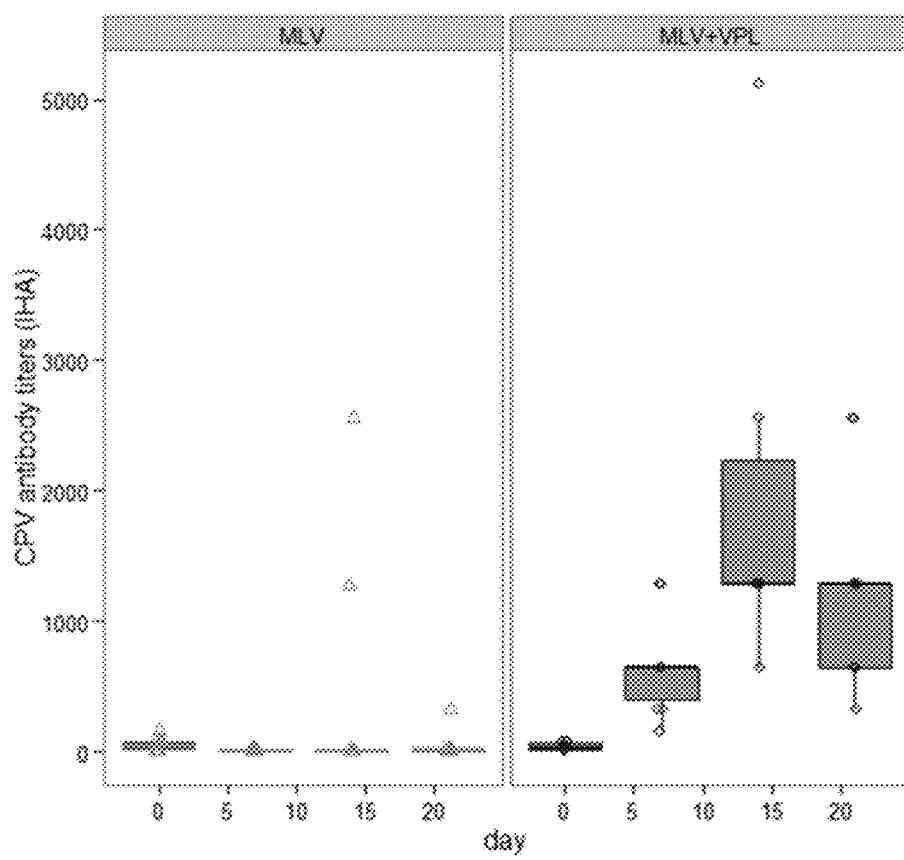
Figure 14:
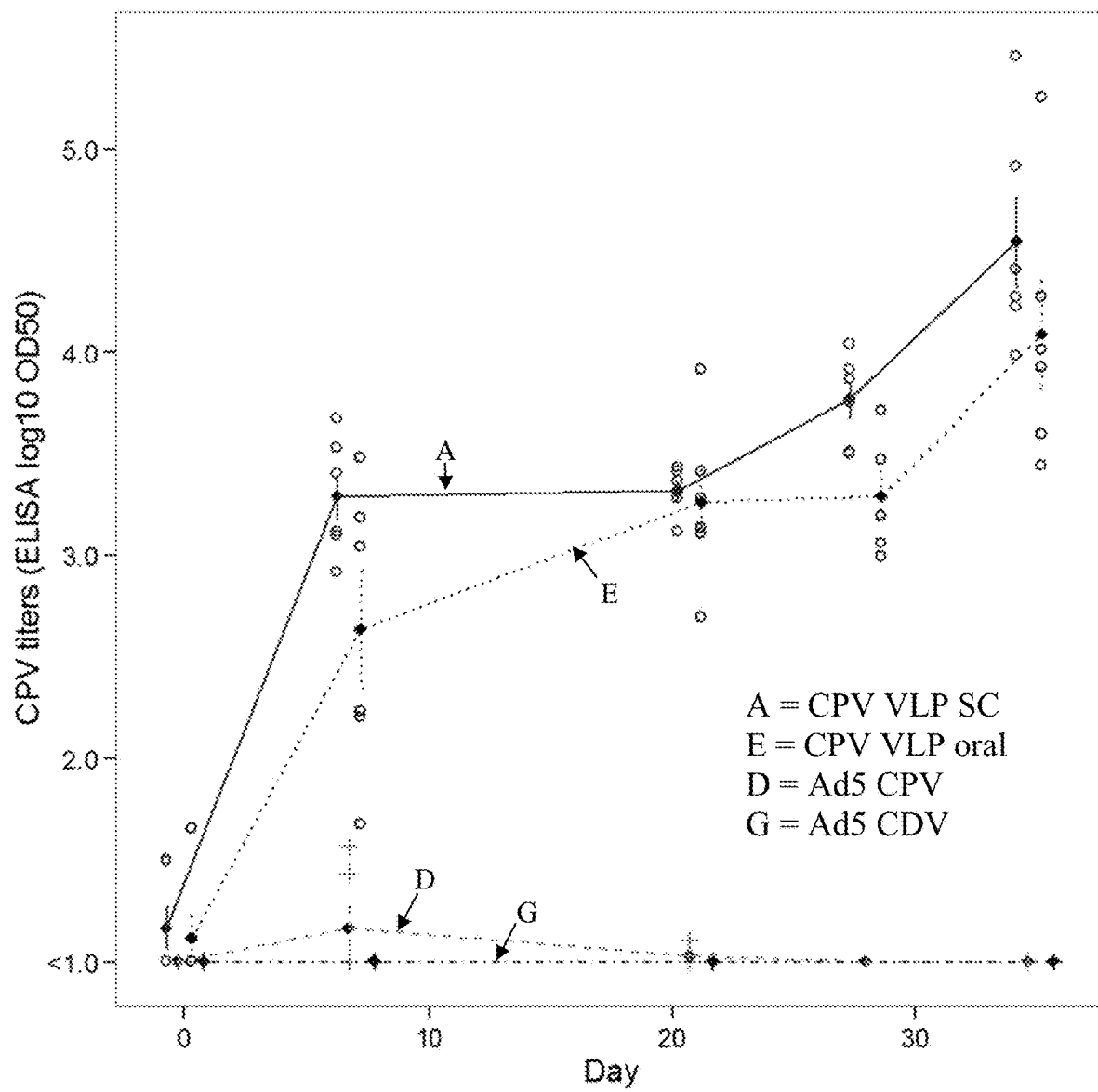

As indicated in FIG. 13, Groups A and E induced in puppies protective levels of CPV antibody titers.

Example 7 Vaccination of Canines with Baculovirus-Expressed CPV Capsid Protein (VLP), VLP+RECOMBITEK® C4, RECOMBITEK® C4 Alone or NOBIVAC® 3

The objective of the study was to assess the antibody response following the administration of various experimental multivalent vaccine formulations containing conventional CPV-2 MLV or baculovirus-expressed, CPV-2c recombinant Virus Like Particle Vaccine (VLP) and one competitor/commercial vaccine in dogs with CPV MDAs.

Forty 6-7 week old maternal derived antibodies (MDAs) positive beagle dogs from bitches previously immunized for CPV during pregnancy, were randomly assigned to four treatment groups (n=10 dogs) using litter and antibody titer. Titrations from blood samples collected on Day −27 were used for the randomization. All dogs were vaccinated twice, 21 days apart with the assigned vaccine according to Table 8 below. Puppies have CPV maternally derived Ab (MDA) at D0.

TABLE 8

Experimental design for CPV VLP v. RECOMBITEK ® C4 and NOBIVAC ® study

| Groups | Vaccination at Day 0 and Day 21 | Titers | No. Dogs |
|---|---|---|---|
| 1 | CPV VLP Test Vaccine #4 (1 ml) *VLPs CPV-2c | 273.5 μg total protein 7.1 Log HA Titer | 10 |
| 2 | CPV VLP #4 (0.5 ml) *VLPs CPV-2c + RECOMBITEK ® C4 #1 (CDV-CAV-CPi, CPV2)*** (1 ml) | 273.5 μg total protein 7.1 Log HA Titer CPV: 6.9 TCID50/ml CDV: 7.1 TCID50/ml CPi: 5.8 TCID50/ml CAV2: 6.0 TCID50/ml | 10 |
| 3 | RECOMBITEK ® C4 #1 (CDV-CAV-CPi, CPV2)*** (1 ml) | CPV: 6.9 TCID50/ml CDV: 7.1 TCID50/ml CPi: 5.8 TCID50/ml CAV2: 6.0 TCID50/ml | 10 |
| 4 | NOBIVAC ® 3 (CDV-CAV2-CPV2) (1 ml) | Unknown | 10 |

*Virus Like Particles of canine Parvovirus VP2: VLPs CPV-2c
**Administered on the same side as the concurrent vaccine approximately 3 cm away
***CDV-CAV-CPi-CPV2 vaccine is referred as C4
HA: Hemagglutination in 0.5 ml Blood was collected from all dogs on Days 0, 7, 15, 21, 28, 35 and 42 and the sera were tested for CPV antibodies by the HAI and Serum Neutralization Antibodies (SNA) assays.

The CPV HAI titers were reported as the inverse of the highest dilution preventing hemagglutination and a value <20 was considered negative.

Figure 15:
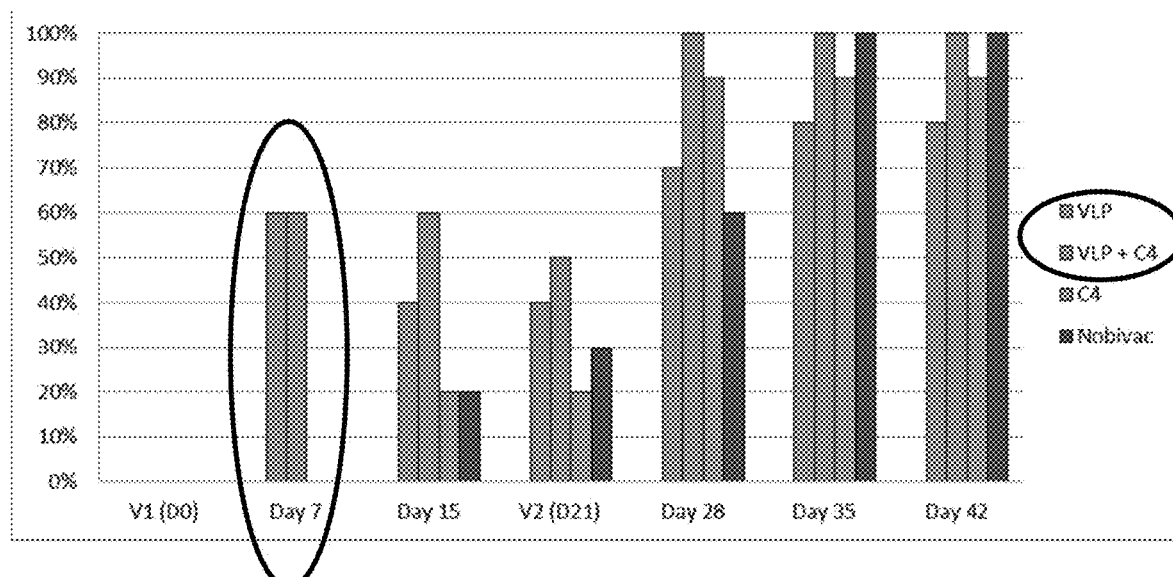
Figure 16:
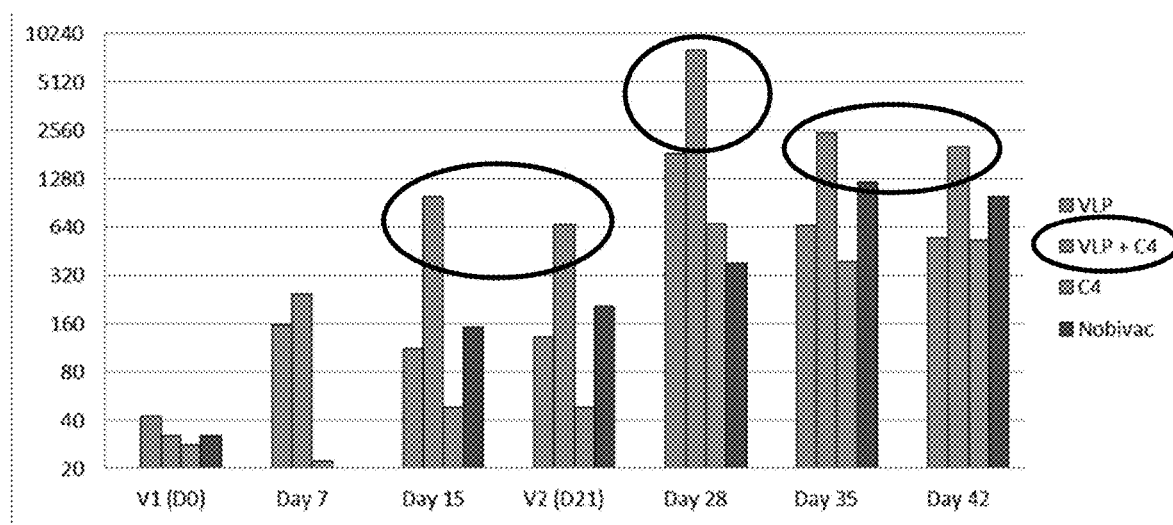

Except for 2 dogs in group 3 (C4) all dogs in each group tested positive to CPV by HAI on Day 0, prior to vaccination. Seroconversion following vaccination was defined as an increase in titer by 4 fold or more from Day 0. Following the first vaccination, 6 out 10 dogs vaccinated with the VLP-CPV2c (Group 1) and 6 out 10 dogs vaccinated with VLP-CPV2c-C4 (Group 2) seroconverted by Day 7. There were no responders in groups 3 and 4 (i.e. groups not containing VLPs) on Day 7. By Day 21, 5 out 10 dogs from Group 2 (VLP-CPV2c-C4), 4 out 10 from Group 1 (VLP-CPV2c), 3 out 10 from Group 4 (NOBIVAC3®) and 2 out 10 from Group 3 (C4) seroconverted (FIG. 15).

Figure 17:
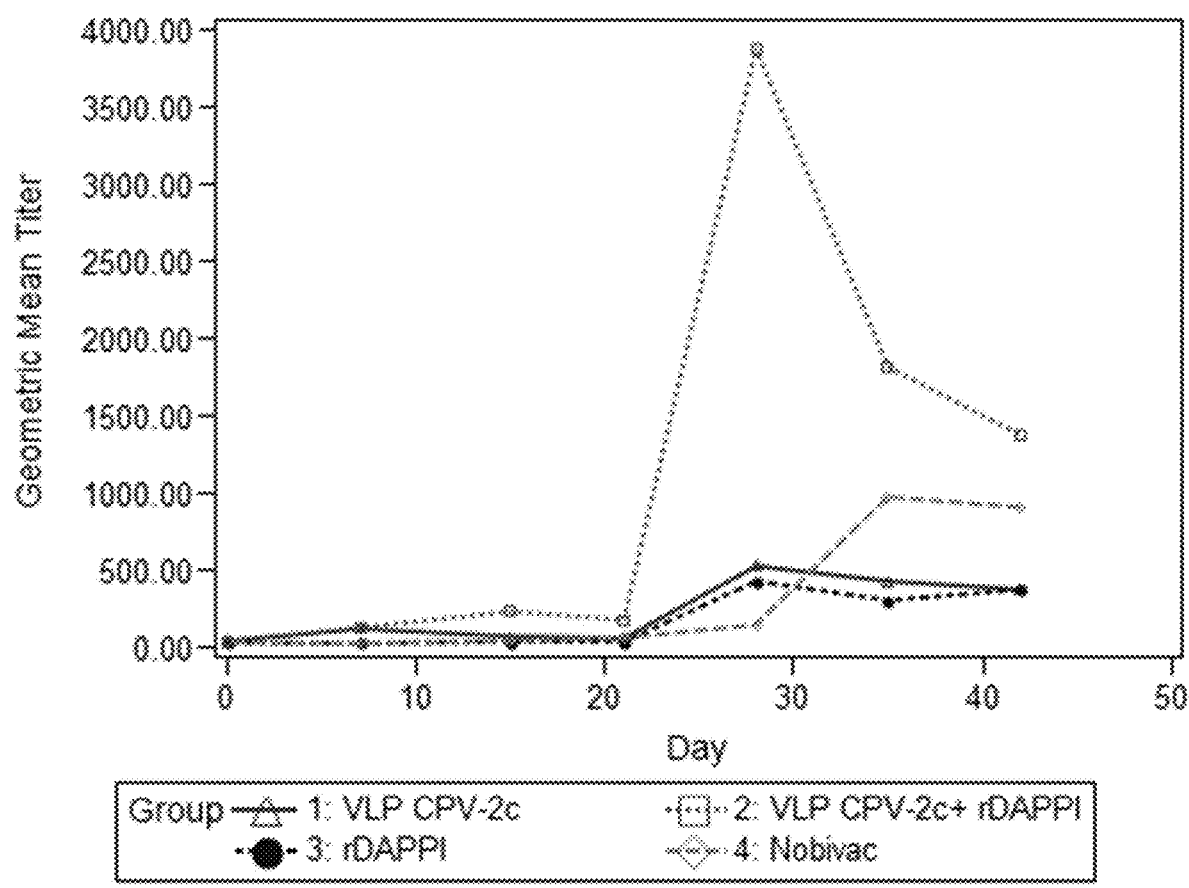

Following the second vaccination, by Day 35 (2 weeks post-vax) seroconversion was observed in all dogs from Groups 2 (VLP-CPV2c-C4) and 4 (NOBIVAC3®) followed by 9 in Group 3 (C4) and 8 in Group 1 (VLP-CPV2c). The VLP+C4 (Group 2) treatment induced the highest geometric mean antibody titer throughout the study. See FIG. 17. Seven days after V2, on Day 28, the GMT of this group was ~7.5 times higher than VLP alone (GMT=520), ~9 times higher than C4 alone (GMT=422) and ~28 times higher than the NOBIVAC3@ group (GMT=139).

TABLE 9

IHA Titers by ID and Day for CPV VLP v. RECOMBITEK ® C4 and NOBIVAC ® study

| Group | Vaccine | Dog ID | Day 0 | Day 7 | Day 15 | Day 21 | Day 28 | Day 35 | Day 42 |
|---|---|---|---|---|---|---|---|---|---|
| 1 | VLP CPV-2c | LCR-5 | 80 | 40 | <20 | <20 | 40 | 40 | 40 |
| | | LGR-5 | 40 | 40 | <20 | <20 | 640 | 1280 | 1280 |
| | | LRR-5 | 20 | 160 | 160 | 160 | 10240 | 1280 | 1280 |
| | | LVQ-5 | 20 | 80 | 80 | 80 | 2560 | 640 | 640 |
| | | QQR-5 | 20 | 320 | 40 | 20 | 160 | 160 | 160 |
| | | RCR-5 | 40 | 320 | 80 | 20 | 640 | 640 | 640 |
| | | RDR-5 | 20 | 160 | 320 | 640 | 2560 | 1280 | 640 |
| | | RGQ-5 | 20 | 320 | 320 | 320 | 1280 | 640 | 320 |
| | | RLQ-5 | 80 | 80 | 40 | <20 | 80 | 160 | 320 |
| | | RRR-5 | 80 | 40 | 20 | <20 | 80 | 320 | 160 |
| 2 | VLP CPV-2c+ rDAPPI | LDR-5 | 20 | 160 | 160 | 40 | 5120 | 1280 | 640 |
| | | LHR-5 | 40 | 40 | <20 | <20 | 1280 | 640 | 640 |
| | | LSQ-5 | 20 | 1280 | 1280 | 640 | 20480 | 5120 | 2560 |
| | | LWQ-5 | 40 | 160 | 5120 | 2560 | 20480 | 5120 | 5120 |
| | | PKR-5 | 40 | 20 | <20 | <20 | 1280 | 1280 | 1280 |
| | | PLQ-5 | 40 | 80 | 1280 | 640 | 20480 | 5120 | 5120 |
| | | QRR-5 | 20 | 160 | 1280 | 1280 | 5120 | 2560 | 2560 |
| | | RHQ-5 | 20 | 320 | 640 | 1280 | 5120 | 2560 | 1280 |
| | | ROQ-5 | 40 | 40 | 20 | <20 | 320 | 640 | 640 |
| | | RSQ-5 | 40 | 160 | 40 | 40 | 1280 | 640 | 320 |

TABLE 9-continued

IHA Titers by ID and Day for CPV VLP v. RECOMBITEK ® C4 and NOBIVAC ® study

| Group | Vaccine | Dog ID | Day 0 | 7 | 15 | 21 | 28 | 35 | 42 |
|---|---|---|---|---|---|---|---|---|---|
| 3 | rDAPPI | LPR-5 | 20 | <20 | 160 | 160 | 1280 | 640 | 640 |
|  |  | LQR-5 | 20 | <20 | 160 | 160 | 640 | 640 | 320 |
|  |  | LTQ-5 | 20 | <20 | <20 | <20 | 640 | 320 | 640 |
|  |  | PIR-5 | 20 | <20 | <20 | <20 | 160 | 320 | 640 |
|  |  | POQ-5 | <20 | <20 | <20 | <20 | 1280 | 640 | 1280 |
|  |  | QSR-5 | 40 | 20 | 20 | <20 | 160 | 320 | 160 |
|  |  | RER-5 | <20 | <20 | <20 | <20 | 640 | 320 | 640 |
|  |  | RIQ-5 | 20 | <20 | <20 | <20 | 1280 | 320 | 640 |
|  |  | RPQ-5 | 80 | 40 | 20 | 20 | <20 | <20 | <20 |
|  |  | RTQ-5 | 20 | 20 | <20 | <20 | 640 | 320 | 320 |
| 4 | Nobivac | LER-5 | 40 | 20 | <20 | <20 | <20 | 640 | 640 |
|  |  | LFR-5 | 20 | <20 | <20 | <20 | 640 | 1280 | 1280 |
|  |  | LUQ-5 | 40 | 20 | <20 | <20 | 40 | 1280 | 1280 |
|  |  | PJR-5 | 20 | <20 | <20 | <20 | <20 | 640 | 640 |
|  |  | QTR-5 | 40 | 20 | <20 | <20 | 160 | 2560 | 1280 |
|  |  | RFR-5 | 20 | <20 | 1280 | 640 | 1280 | 1280 | 1280 |
|  |  | RJQ-5 | 20 | <20 | 80 | 640 | 1280 | 2560 | 1280 |
|  |  | RKR-5 | 40 | 20 | 20 | <20 | 40 | 1280 | 1280 |
|  |  | RQR-5 | 40 | 20 | <20 | <20 | 160 | 320 | 320 |
|  |  | RUQ-5 | 40 | 20 | 20 | 640 | 160 | 320 | 640 |

TABLE 10

Summary Statistics for CPV VLP v. RECOMBITEK ® C4 and NOBIVAC ® study

| Day | Group | Vaccine | N | Geometric Mean | Arithmetic Mean | Median | Min | Max |
|---|---|---|---|---|---|---|---|---|
| 0 | 1 | VLP CPV-2c | 10 | 34.82 | 42.00 | 30 | 20.0 | 80.0 |
|  | 2 | VLP CPV-2c+ rDAPPI | 10 | 30.31 | 32.00 | 40 | 20.0 | 40.0 |
|  | 3 | rDAPPI | 10 | 24.62 | 28.00 | 20 | 20.0 | 80.0 |
|  | 4 | Nobivac | 10 | 30.31 | 32.00 | 40 | 20.0 | 40.0 |
| 7 | 1 | VLP CPV-2c | 10 | 113.14 | 156.00 | 120 | 40.0 | 320.0 |
|  | 2 | VLP CPV-2c+ rDAPPI | 10 | 121.26 | 242.00 | 160 | 20.0 | 1280.0 |
|  | 3 | rDAPPI | 10 | 21.44 | 22.00 | 20 | 20.0 | 40.0 |
|  | 4 | Nobivac | 10 | 20.00 | 20.00 | 20 | 20.0 | 20.0 |
| 15 | 1 | VLP CPV-2c | 10 | 64.98 | 110.00 | 60 | 20.0 | 320.0 |
|  | 2 | VLP CPV-2c+ rDAPPI | 10 | 226.27 | 986.00 | 400 | 20.0 | 5120.0 |
|  | 3 | rDAPPI | 10 | 30.31 | 48.00 | 20 | 20.0 | 160.0 |
|  | 4 | Nobivac | 10 | 34.82 | 152.00 | 20 | 20.0 | 1280.0 |
| 21 | 1 | VLP CPV-2c | 10 | 52.78 | 132.00 | 20 | 20.0 | 640.0 |
|  | 2 | VLP CPV-2c+ rDAPPI | 10 | 171.48 | 654.00 | 340 | 20.0 | 2560.0 |
|  | 3 | rDAPPI | 10 | 30.31 | 48.00 | 20 | 20.0 | 160.0 |
|  | 4 | Nobivac | 10 | 56.57 | 206.00 | 20 | 20.0 | 640.0 |
| 28 | 1 | VLP CPV-2c | 10 | 519.84 | 1828.00 | 640 | 40.0 | 10240.0 |
|  | 2 | VLP CPV-2c+ rDAPPI | 10 | 3880.23 | 8096.00 | 5120 | 320.0 | 20480.0 |
|  | 3 | rDAPPI | 10 | 422.24 | 674.00 | 640 | 20.0 | 1280.0 |
|  | 4 | Nobivac | 10 | 139.29 | 380.00 | 160 | 20.0 | 1280.0 |
| 35 | 1 | VLP CPV-2c | 10 | 422.24 | 644.00 | 640 | 40.0 | 1280.0 |
|  | 2 | VLP CPV-2c+ rDAPPI | 10 | 1810.19 | 2496.00 | 1920 | 640.0 | 5120.0 |
|  | 3 | rDAPPI | 10 | 298.57 | 386.00 | 320 | 20.0 | 640.0 |
|  | 4 | Nobivac | 10 | 970.06 | 1216.00 | 1280 | 320.0 | 2560.0 |
| 42 | 1 | VLP CPV-2c | 10 | 367.58 | 548.00 | 480 | 40.0 | 1280.0 |
|  | 2 | VLP CPV-2c+ rDAPPI | 10 | 1371.87 | 2016.00 | 1280 | 320.0 | 5120.0 |
|  | 3 | rDAPPI | 10 | 367.58 | 530.00 | 640 | 20.0 | 1280.0 |
|  | 4 | Nobivac | 10 | 905.10 | 992.00 | 1280 | 320.0 | 1280.0 |

*The '<' signs were removed from the values in order to calculate the summary statistics.

Example 8 Vaccination of Canines with Baculovirus-Expressed CPV Capsid Protein (VLP), VLP+RECOMBITEK® C4, RECOMBITEK® C4 Alone or NOBIVAC® 3

The objective of this study was to assess the CPV antibody response following the administration of experimental Virus Like Particles made of the VP2 capsid protein of canine Parvovirus type 2 (VLPs CPV-2c) at different titers in combination with a CPV-2 MLV multivalent vaccine formulation and one commercial vaccine in dogs with CPV MDAs.

Fifty 6-7 week old maternal derived antibodies (MDAs) positive beagle dogs from bitches previously immunized for CPV during pregnancy, were randomly assigned to five treatment groups (n=10 dogs per group) using litter and antibody titer. Titrations from blood samples collected on Day −15 were used for the randomization.

Vaccines were prepared by rehydrating a lyophilized component with a diluent component. The Lyophilized serial used for the Test vaccines #1, #2, #3 and #5 was the same experimental 4-way (C4) vaccine. The titers for each component were as follow: CPV:6.1 Log TCID50/ml (~0.2 ml of 1× culture), CDV: 7.3 Log TCID50/ml, CPi: 5.5 Log TCID50/ml and CAV2:6.0 Log TCID50/ml. All dogs were vaccinated twice, 21 days apart with the assigned vaccine according to Table 11 below.

TABLE 11

Experimental design for CPV VLP v. RECOMBITEK ® C4 and NOBIVAC ® study

| GROUP (n = 10) | Vaccine Lyophilized component | Vaccine Diluent component |
|---|---|---|
| 1 C4 + High dose VLP-CPV2c | CDV-CAV2-CPi-CPV | VLPs CPV-2c; lot #: 14Dec15 Undiluted 7.0 Log aHA/ml ~10 ml of 1X culture |
| 2 C4 + Mid dose VLP-CPV2c | CDV-CAV2-CPi-CPV | VLPs CPV-2c; lot #: 14Dec15 Diluted 1:5 in water 6.3 Log aHA/ml ~2 ml of 1X culture |
| 3 C4 + Low dose VLP-CPV2c | CDV-CAV2-CPi-CPV | VLPs CPV-2c; lot #: 14Dec15 Diluted 1:25 in water 5.7 Log aHA/ml ~0.4 ml of 1X culture |
| 4 Nobivac ® 3 DAPv | Nobivac ® Canine 3 (CDV-CAV2-CPV2) (1 ml) | Unknown |
| 5 C4 No VLP-CPV2c | CDV-CAV2-CPi-CPV | Water |

Blood was collected from all dogs on Days 0, 7, 15, 21, 28, 34 and 42 and the sera were tested for CPV antibodies by the HAI assay.

Figure 18:
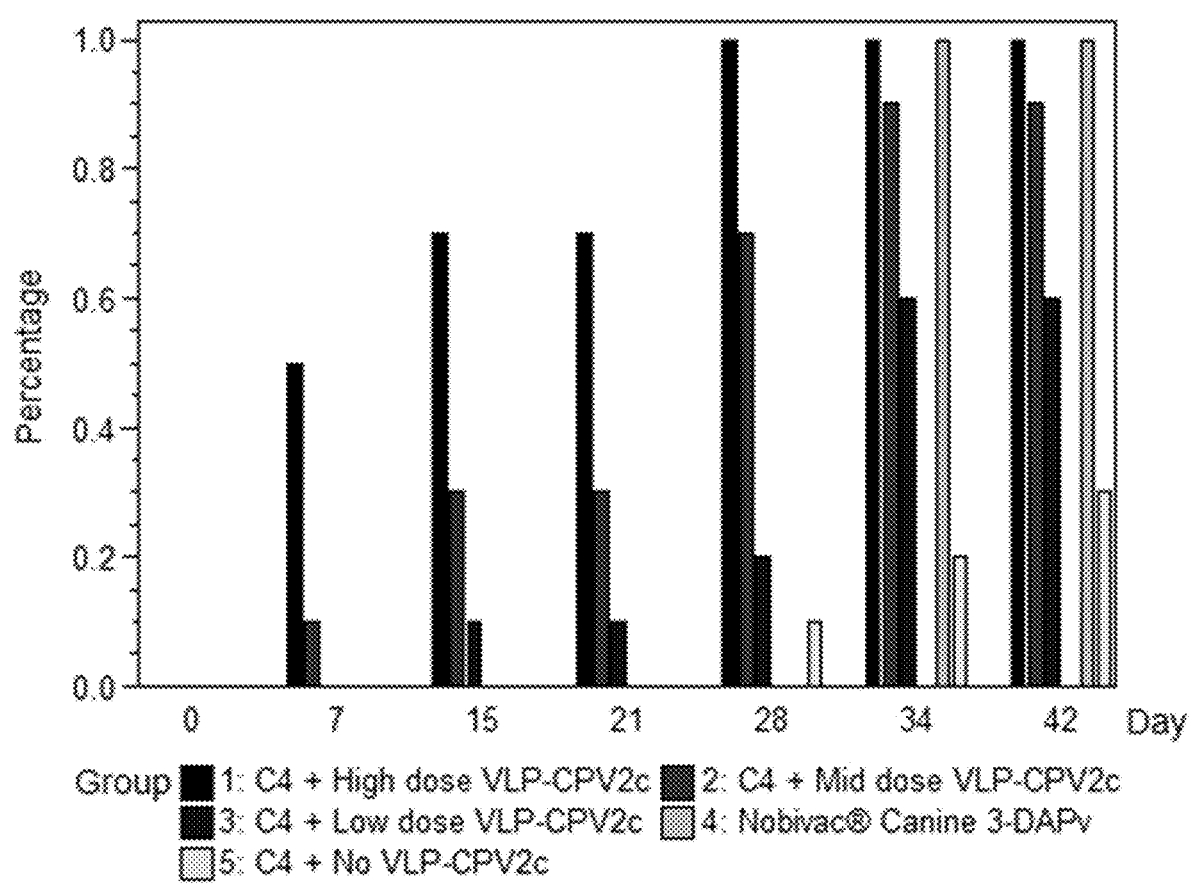

The CPV HAI titers were reported as the inverse of the highest dilution preventing hemagglutination and a value <20 was considered negative. All dogs in each group tested positive to CPV by HAI on Day 0, prior to vaccination (GMT average titers for all groups between 42.87 and 80). Seroconversion following vaccination was defined as an increase in titer by 4 fold or more from Day 0. Dogs seroconverting were categorized as responders (FIG. 18). Seven days after the first vaccination, 5 out 10 dogs vaccinated with the high dose VLP-CPV2c-C4 (Group 1) and 1 out 10 dogs vaccinated with mid dose VLP-CPV2c-C4 (Group 2) seroconverted. There were no responders in groups 3, 4 and 5 (i.e. groups containing low or no VLPs) on Day 7. Twenty-one days after the first vaccination, all dogs from Group 1 (high dose VLP-CPV2c-C4), 3 out 10 from Group 2 (mid dose VLP-CPV2c-C4), 1 out 10 from Group 3 (low dose VLP-CPV2c-C4). There were no responders in groups 4 and 5 (i.e. groups not containing VLPs) (FIG. 18).

On Day 34, 13 days following the second vaccination, seroconversion was observed in all dogs from Groups 1 (high dose VLP-CPV2c-C4) and 4 (NOBIVAC3®) followed by 9 in Group 2 (mid dose VLP-CPV2c-C4) 6 in Group 3 (low dose VLP-CPV2c-C4) and 1 in Group 5 (C4 no VLP).

Figure 19:
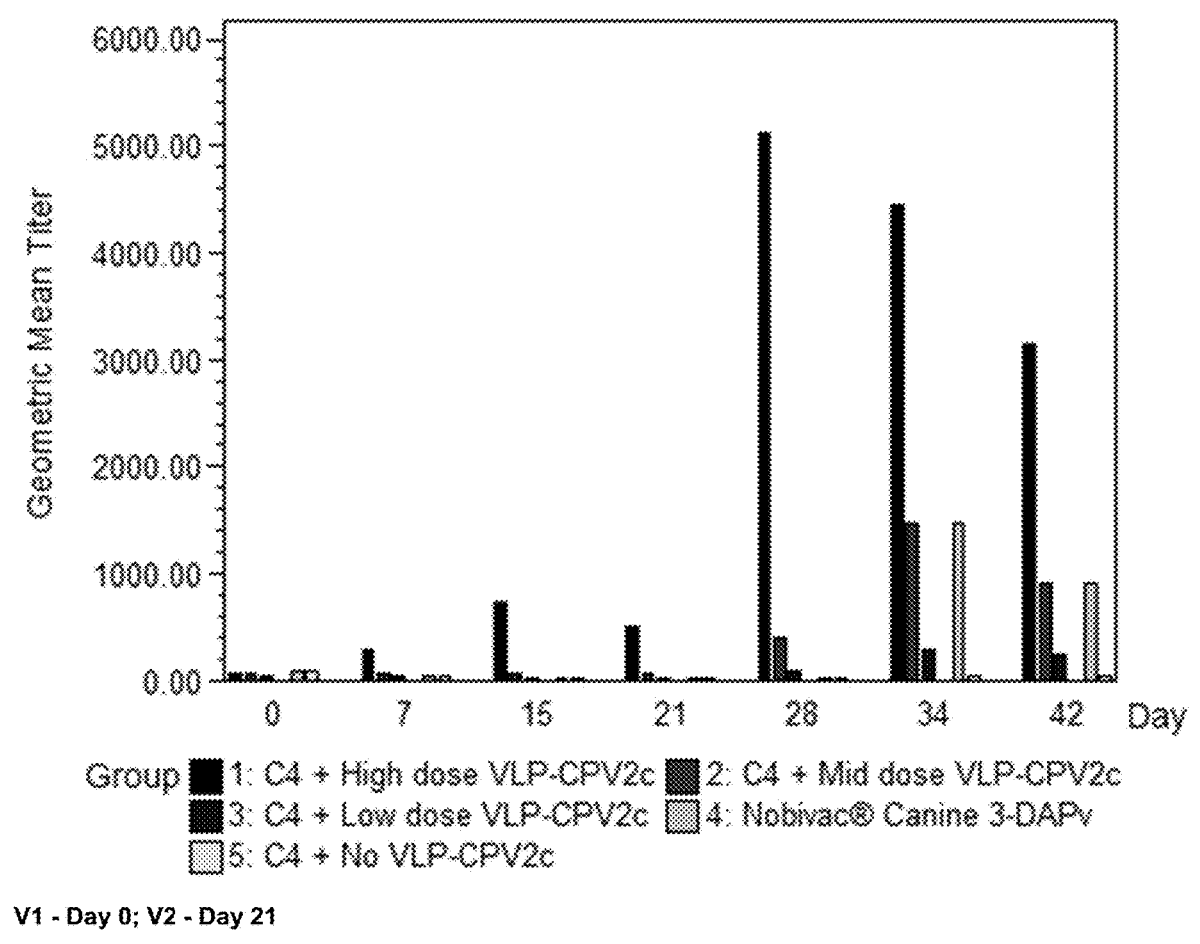

As shown in FIG. 19, the high dose VLP+C4 (Group 1) treatment induced the highest geometric mean antibody titer throughout the study. Thirteen days after V2, on Day 34, the GMT of this group was 4457.22, followed by the mid dose VLP-CPV2c-C4 and the NOBIVAC3® groups; (GMT=14700.33), the low dose VLP-CPV2c-C4 (GMT=298.57) and C4 alone (GMT=45.95).

TABLE 12

HI Results by Group, ID and Day for second CPV VLP v. RECOMBITEK ® $C_4$ and NOBIVAC ® study

| Group | *Vaccine | ID | Day 0 | 7 | 15 | 21 | 28 | 34 | 42 |
|---|---|---|---|---|---|---|---|---|---|
| 1 | Test Vaccine #1 (rDAPP; C4) + VLPs CPV-2c 7.1 Log HA | PFE6 | 40 | 320 | 640 | 1280 | 5120 | 5120 | 2560 |
| | | PRD6 | 40 | 5120 | 5120 | 2560 | 5120 | 5120 | 2560 |
| | | QFC6 | 40 | 5120 | 5120 | 5120 | 10240 | 10240 | 5120 |
| | | QOE6 | 20 | 160 | 2560 | 2560 | 10240 | 5120 | 5120 |
| | | RIE6 | 80 | 80 | 40 | 20 | 1280 | 2560 | 2560 |
| | | RKD6 | 80 | 320 | 1280 | 640 | 10240 | 5120 | 2560 |
| | | SPF6 | 160 | 80 | 2560 | 1280 | 10240 | 10240 | 5120 |
| | | TAF6 | 80 | 160 | 1280 | 640 | 10240 | 5120 | 5120 |
| | | VAF6 | 80 | 160 | 80 | 80 | 640 | 1280 | 1280 |
| | | VCE6 | 40 | 80 | 80 | 40 | 5120 | 2560 | 2560 |
| | | GMT | 56.57 | 298.57 | 735.17 | 519.84 | 5120.00 | 4457.22 | 3151.73 |
| 2 | Test Vaccine #2 (rDAPP; C4) + VLPs CPV-2c 6.4 Log HA | PWF6 | 40 | 160 | 320 | 160 | 2560 | 2560 | 1280 |
| | | QBF6 | 160 | 160 | 80 | 40 | 640 | 640 | 320 |
| | | QLE6 | 40 | 80 | 1280 | 2560 | 10240 | 10240 | 5120 |
| | | RJD6 | 80 | 80 | 320 | 160 | 2560 | 1280 | 1280 |
| | | RWE6 | 80 | 80 | 20 | <20 | 80 | 2560 | 1280 |
| | | RXE6 | 40 | 80 | 20 | 20 | 320 | 640 | 640 |
| | | STE6 | 80 | 40 | 20 | 20 | 40 | 640 | 320 |
| | | SUF6 | 40 | 40 | 40 | 20 | 160 | 5120 | 2560 |
| | | TBF6 | 80 | 40 | 40 | 40 | 320 | 2560 | 1280 |
| | | VDE6 | 80 | 40 | 40 | 20 | 40 | 160 | 160 |
| | | GMT | 64.98 | 69.64 | 74.64 | 56.57 | 393.97 | 1470.33 | 905.10 |
| 3 | Test Vaccine #3 (rDAPP; C4) + VLPs CPV-2c 5.7 Log HA | QDE6 | 80 | 40 | 20 | 20 | 40 | 80 | 80 |
| | | QED6 | 40 | 40 | 320 | 320 | 2560 | 2560 | 1280 |
| | | QKE6 | 40 | 20 | <20 | <20 | 40 | 160 | 160 |
| | | RGF6 | 40 | 80 | 40 | 20 | 40 | 1280 | 640 |
| | | RPD6 | 40 | 40 | 20 | 20 | 40 | 1280 | 640 |

TABLE 12-continued

HI Results by Group, ID and Day for second CPV VLP v. RECOMBITEK ® C₄ and NOBIVAC ® study

| Group | *Vaccine | ID | Day 0 | 7 | 15 | 21 | 28 | 34 | 42 |
|---|---|---|---|---|---|---|---|---|---|
| | | RTF6 | 40 | 40 | 20 | <20 | 80 | 1280 | 1280 |
| | | SCE6 | 20 | 20 | <20 | <20 | 1280 | 1280 | 1280 |
| | | SQF6 | 80 | 40 | 40 | 20 | 40 | 160 | 160 |
| | | UOE6 | 40 | 20 | 20 | <20 | 40 | 20 | <20 |
| | | UXF6 | 40 | 40 | 20 | 20 | 20 | <20 | <20 |
| | | GMT | 42.87 | 34.82 | 30.31 | 26.39 | 85.74 | 298.57 | 242.51 |
| 4 | Nobivac ® Canine 3-DAPv | PCE6 | 20 | <20 | <20 | <20 | 40 | 640 | 640 |
| | | QCF6 | 80 | 40 | 20 | <20 | <20 | 2560 | 640 |
| | | RFF6 | 160 | 40 | 20 | 20 | 20 | 1280 | 640 |
| | | RLD6 | 160 | 160 | 20 | <20 | <20 | 2560 | 1280 |
| | | ROD6 | 160 | 40 | 20 | <20 | <20 | 1280 | 1280 |
| | | SDE6 | 40 | 40 | 20 | <20 | 40 | 1280 | 1280 |
| | | SWE6 | 40 | 20 | <20 | <20 | <20 | 640 | 320 |
| | | SXE6 | 40 | 20 | <20 | <20 | <20 | 1280 | 1280 |
| | | TCE6 | 160 | 40 | <20 | 20 | <20 | 2560 | 1280 |
| | | UYF6 | 160 | 160 | 40 | 40 | <20 | 2560 | 1280 |
| | | GMT | 80.00 | 42.87 | 21.44 | 21.44 | 22.97 | 1470.33 | 905.10 |
| 5 | Test Vaccine #5 (rDAPP; C4) | PBE6 | 20 | <20 | <20 | <20 | 80 | 1280 | 640 |
| | | REF6 | 80 | 40 | 20 | <20 | <20 | <20 | <20 |
| | | RHE6 | 160 | 20 | <20 | <20 | <20 | <20 | <20 |
| | | RUE6 | 80 | 80 | 40 | 20 | <20 | <20 | <20 |
| | | SVF6 | 160 | <20 | <20 | <20 | <20 | <20 | <20 |
| | | TDE6 | 160 | 160 | 40 | <20 | <20 | <20 | <20 |
| | | ULF6 | 20 | 20 | <20 | <20 | <20 | 320 | 320 |
| | | UPE6 | 80 | 20 | <20 | <20 | <20 | 80 | 320 |
| | | UZF6 | 160 | 160 | 40 | 20 | 20 | <20 | <20 |
| | | VBF6 | 80 | 20 | 20 | 20 | <20 | <20 | <20 |
| | | GMT | 80.00 | 37.32 | 24.62 | 20.00 | 22.97 | 45.95 | 49.25 |

*For the purpose of Example 8, the below names will be used in the following tables and charts.
*C4 + High dose VLP-CPV2c = Test Vaccine #1
*C4 + Mid dose VLP-CPV2c = Test Vaccine #2
*C4 + Low dose VLP-CPV2c = Test Vaccine #3
*C4 + No VLP-CPV2c = Test Vaccine #5

TABLE 13

Summary Statistics* by group for second CPV VLP v. RECOMBITEK ® $C_4$ and NOBIVAC ® study

| Day | Group | Vaccine | N | Geometric Mean | Arithmetic Mean | Median | Min | Max |
|---|---|---|---|---|---|---|---|---|
| 0 | 1 | C4 + High dose VLP-CPV2c | 10 | 56.57 | 66.00 | 60 | 20.0 | 160.0 |
| | 2 | C4 + Mid dose VLP-CPV2c | 10 | 64.98 | 72.00 | 80 | 40.0 | 160.0 |
| | 3 | C4 + low dose VLP-CPV2c | 10 | 42.87 | 46.00 | 40 | 20.0 | 80.0 |
| | 4 | Nobivac ® Canine 3-DAPv | 10 | 80.00 | 102.00 | 120 | 20.0 | 160.0 |
| | 5 | C4 + No VLP-CPV2c | 10 | 80.00 | 100.00 | 80 | 20.0 | 160.0 |
| 7 | 1 | C4 + High dose VLP-CPV2c | 10 | 298.57 | 1160.00 | 160 | 80.0 | 5120.0 |
| | 2 | C4 + Mid dose VLP-CPV2c | 10 | 69.64 | 80.00 | 80 | 40.0 | 160.0 |
| | 3 | C4 + low dose VLP-CPV2c | 10 | 34.82 | 38.00 | 40 | 20.0 | 80.0 |
| | 4 | Nobivac ® Canine 3-DAPv | 10 | 42.87 | 58.00 | 40 | 20.0 | 160.0 |
| | 5 | C4 + No VLP-CPV2c | 10 | 37.32 | 56.00 | 20 | 20.0 | 160.0 |
| 15 | 1 | C4 + High dose VLP-CPV2c | 10 | 735.17 | 1876.00 | 1280 | 40.0 | 5120.0 |
| | 2 | C4 + Mid dose VLP-CPV2c | 10 | 74.64 | 218.00 | 40 | 20.0 | 1280.0 |
| | 3 | C4 + low dose VLP-CPV2c | 10 | 30.31 | 54.00 | 20 | 20.0 | 320.0 |
| | 4 | Nobivac ® Canine 3-DAPv | 10 | 21.44 | 22.00 | 20 | 20.0 | 40.0 |
| | 5 | C4 + No VLP-CPV2c | 10 | 24.62 | 26.00 | 20 | 20.0 | 40.0 |
| 21 | 1 | C4 + High dose VLP-CPV2c | 10 | 519.84 | 1422.00 | 960 | 20.0 | 5120.0 |
| | 2 | C4 + Mid dose VLP-CPV2c | 10 | 56.57 | 306.00 | 30 | 20.0 | 2560.0 |
| | 3 | C4 + low dose VLP-CPV2c | 10 | 26.39 | 50.00 | 20 | 20.0 | 320.0 |
| | 4 | Nobivac ® Canine 3-DAPv | 10 | 21.44 | 22.00 | 20 | 20.0 | 40.0 |
| | 5 | C4 + No VLP-CPV2c | 10 | 20.00 | 20.00 | 20 | 20.0 | 20.0 |
| 28 | 1 | C4 + High dose VLP-CPV2c | 10 | 5120.00 | 6848.00 | 7680 | 640.0 | 10240.0 |
| | 2 | C4 + Mid dose VLP-CPV2c | 10 | 393.97 | 1696.00 | 320 | 40.0 | 10240.0 |
| | 3 | C4 + low dose VLP-CPV2c | 10 | 85.74 | 418.00 | 40 | 20.0 | 2560.0 |
| | 4 | Nobivac ® Canine 3-DAPv | 10 | 22.97 | 24.00 | 20 | 20.0 | 40.0 |
| | 5 | C4 + No VLP-CPV2c | 10 | 22.97 | 26.00 | 20 | 20.0 | 80.0 |
| 34 | 1 | C4 + High dose VLP-CPV2c | 10 | 4457.22 | 5248.00 | 5120 | 1280.0 | 10240.0 |
| | 2 | C4 + Mid dose VLP-CPV2c | 10 | 1470.33 | 2640.00 | 1920 | 160.0 | 10240.0 |

TABLE 13-continued Summary Statistics* by group for second CPV VLP v. RECOMBITEK ® C$_4$ and NOBIVAC ® study

| Day | Group | Vaccine | N | Geometric Mean | Arithmetic Mean | Median | Min | Max |
|---|---|---|---|---|---|---|---|---|
|  | 3 | C4 + low dose VLP-CPV2c | 10 | 298.57 | 812.00 | 720 | 20.0 | 2560.0 |
|  | 4 | Nobivac ® Canine 3-DAPv | 10 | 1470.33 | 1664.00 | 1280 | 640.0 | 2560.0 |
|  | 5 | C4 + No VLP-CPV2c | 10 | 45.95 | 182.00 | 20 | 20.0 | 1280.0 |
| 42 | 1 | C4 + High dose VLP-CPV2c | 10 | 3151.73 | 3456.00 | 2560 | 1280.0 | 5120.0 |
|  | 2 | C4 + Mid dose VLP-CPV2c | 10 | 905.10 | 1424.00 | 1280 | 160.0 | 5120.0 |
|  | 3 | C4 + low dose VLP-CPV2c | 10 | 242.51 | 556.00 | 400 | 20.0 | 1280.0 |
|  | 4 | Nobivac ® Canine 3-DAPv | 10 | 905.10 | 992.00 | 1280 | 320.0 | 1280.0 |
|  | 5 | C4 + No VLP-CPV2c | 10 | 49.25 | 142.00 | 20 | 20.0 | 640.0 |

TABLE 14

Number of Responders (Serocoversion) by Group and Day; 1 = Yes, 0 = No; Serocoversion is defined as a 4 fold or greater increase in titer from baseline.

| Group | Vaccine | ID | 0 | 7 | 15 | 21 | 28 | 34 | 42 |
|---|---|---|---|---|---|---|---|---|---|
| 1 | C4 + High dose VLP-CPV2c | PFE6 | 0 | 1 | 1 | 1 | 1 | 1 | 1 |
|  |  | PRD6 | 0 | 1 | 1 | 1 | 1 | 1 | 1 |
|  |  | QFC6 | 0 | 1 | 1 | 1 | 1 | 1 | 1 |
|  |  | QOE6 | 0 | 1 | 1 | 1 | 1 | 1 | 1 |
|  |  | RIE6 | 0 | 0 | 0 | 0 | 1 | 1 | 1 |
|  |  | RKD6 | 0 | 1 | 1 | 1 | 1 | 1 | 1 |
|  |  | SPF6 | 0 | 0 | 1 | 1 | 1 | 1 | 1 |
|  |  | TAF6 | 0 | 1 | 1 | 1 | 1 | 1 | 1 |
|  |  | VAF6 | 0 | 0 | 0 | 0 | 1 | 1 | 1 |
|  |  | VCE6 | 0 | 0 | 0 | 0 | 1 | 1 | 1 |
|  |  | Total | 0 | 5 | 7 | 7 | 10 | 10 | 10 |
| 2 | C4 + Mid dose VLP-CPV2c | ID |  |  |  |  |  |  |  |
|  |  | PWF6 | 0 | 1 | 1 | 1 | 1 | 1 | 1 |
|  |  | QBF6 | 0 | 0 | 0 | 0 | 1 | 1 | 1 |
|  |  | QLE6 | 0 | 0 | 1 | 1 | 1 | 1 | 1 |
|  |  | RJD6 | 0 | 0 | 1 | 1 | 1 | 1 | 1 |
|  |  | RWE6 | 0 | 0 | 0 | 0 | 0 | 1 | 1 |
|  |  | RXE6 | 0 | 0 | 0 | 0 | 1 | 1 | 1 |
|  |  | STE6 | 0 | 0 | 0 | 0 | 1 | 1 | 1 |
|  |  | SUF6 | 0 | 0 | 0 | 0 | 1 | 1 | 1 |
|  |  | TBF6 | 0 | 0 | 0 | 0 | 1 | 1 | 1 |
|  |  | VDE6 | 0 | 0 | 0 | 0 | 0 | 0 | 0 |
|  |  | Total | 0 | 1 | 3 | 3 | 7 | 9 | 9 |
| 3 | C4 + low dose VLP-CPV2c | ID |  |  |  |  |  |  |  |
|  |  | QDE6 | 0 | 0 | 0 | 0 | 0 | 0 | 0 |
|  |  | QED6 | 0 | 0 | 1 | 1 | 1 | 1 | 1 |
|  |  | QKE6 | 0 | 0 | 0 | 0 | 0 | 1 | 1 |
|  |  | RGF6 | 0 | 0 | 0 | 0 | 0 | 1 | 1 |
|  |  | RPD6 | 0 | 0 | 0 | 0 | 0 | 1 | 1 |
|  |  | RTF6 | 0 | 0 | 0 | 0 | 0 | 1 | 1 |
|  |  | SCE6 | 0 | 0 | 0 | 0 | 1 | 1 | 1 |
|  |  | SQF6 | 0 | 0 | 0 | 0 | 0 | 0 | 0 |
|  |  | UOE6 | 0 | 0 | 0 | 0 | 0 | 0 | 0 |
|  |  | UXF6 | 0 | 0 | 0 | 0 | 0 | 0 | 0 |
|  |  | Total | 0 | 0 | 1 | 1 | 2 | 6 | 6 |
| 4 | Nobivac ® Canine 3-DAPv | ID |  |  |  |  |  |  |  |
|  |  | PCE6 | 0 | 0 | 0 | 0 | 0 | 1 | 1 |
|  |  | QCF6 | 0 | 0 | 0 | 0 | 0 | 1 | 1 |
|  |  | RFF6 | 0 | 0 | 0 | 0 | 0 | 1 | 1 |
|  |  | RLD6 | 0 | 0 | 0 | 0 | 0 | 1 | 1 |
|  |  | ROD6 | 0 | 0 | 0 | 0 | 0 | 1 | 1 |
|  |  | SDE6 | 0 | 0 | 0 | 0 | 0 | 1 | 1 |
|  |  | SWE6 | 0 | 0 | 0 | 0 | 0 | 1 | 1 |
|  |  | SXE6 | 0 | 0 | 0 | 0 | 0 | 1 | 1 |
|  |  | TCE6 | 0 | 0 | 0 | 0 | 0 | 1 | 1 |
|  |  | UYF6 | 0 | 0 | 0 | 0 | 0 | 1 | 1 |
|  |  | Total | 0 | 0 | 0 | 0 | 0 | 10 | 10 |
| 5 | C4 + No VLP-CPV2c | ID |  |  |  |  |  |  |  |
|  |  | PBE6 | 0 | 0 | 0 | 0 | 1 | 1 | 1 |
|  |  | REF6 | 0 | 0 | 0 | 0 | 0 | 0 | 0 |
|  |  | RHE6 | 0 | 0 | 0 | 0 | 0 | 0 | 0 |
|  |  | RUE6 | 0 | 0 | 0 | 0 | 0 | 0 | 0 |
|  |  | SVF6 | 0 | 0 | 0 | 0 | 0 | 0 | 0 |
|  |  | TDE6 | 0 | 0 | 0 | 0 | 0 | 0 | 0 |
|  |  | ULF6 | 0 | 0 | 0 | 0 | 0 | 1 | 1 |
|  |  | UPE6 | 0 | 0 | 0 | 0 | 0 | 0 | 1 |
|  |  | UZF6 | 0 | 0 | 0 | 0 | 0 | 0 | 0 |
|  |  | VBF6 | 0 | 0 | 0 | 0 | 0 | 0 | 0 |
|  |  | Total | 0 | 0 | 0 | 0 | 1 | 2 | 3 |

Accordingly, CPV VLPs promoted an earlier onset of immunity (001) than MLV alone in MDA+ puppies, and CPV VLPs synergize with MLV C4 in MDA+ puppies. Applicant submits that these results were unexpected and extremely favorable. Overcoming maternally-derived antibodies has long challenged vaccine biologists, and these data indicate that the VLP+MLV approach disclosed herein may be applied broadly to the problem of providing MDA+ offspring with protective immunity.

The invention claimed is:

1. A vaccine capable of inducing a protective immune response against canine parvovirus (CPV) in canines with maternally derived antibodies (MDAs) to CPV, comprising:
   a canine parvovirus modified-live virus (CPV MLV); and
   canine parvovirus virus-like particles (CPV VLPs) in an amount effective to overcome a neutralizing effect of MDAs against CPV in canines with MDAs to CPV.

2. The vaccine of claim 1, wherein the CPV VLPs were produced by expressing a baculovirus vector in insect cells.

3. The vaccine of claim 1, wherein the CPV VLPs comprise a polypeptide having 90% or greater sequence identity to at least one of SEQ ID NOs: 1, 3, 4, 6, 8, 9, and 10.

4. The vaccine of claim 1, wherein the CPV VLPs comprise a polypeptide having SEQ ID NO: 1, 3, 4, 6, 8, 9, or 10.

5. The vaccine of claim 1, further comprising a veterinarily acceptable excipient.

6. The vaccine of claim 5, wherein the vaccine is not adjuvanted.

7. A plasmid configured to produce, when expressed, a canine parvovirus virus-like particle (CPV VLP) comprising a canine parvovirus (CPV) antigenic polypeptide having 90% or greater sequence identity to at least one of SEQ ID NOs: 1, 3, 4, 6, 8, 9, and 10.

8. The plasmid of claim 7, wherein the CPV antigenic polypeptide has SEQ ID NO: 1, 3, 4, 6, 8, 9, or 10.

9. The plasmid of claim 7, wherein the plasmid comprises SEQ ID NO: 2, 5, 7, 11, or 12.

10. The plasmid of claim 9, wherein the plasmid consists of SEQ ID NO:11 or 12.

11. An insect cell stably transformed with the plasmid according to claim 7.

12. A composition comprising substantially purified CPV VLPs produced by expressing the plasmid according to claim 7 in an insect cell.

13. The composition of claim 12, wherein the CPV VLPs comprise a polypeptide having SEQ ID NO: 1, 3, 4, 6, 8, 9, or 10.

14. A method for eliciting a protective immune response against canine parvovirus (CPV) in a canine comprising administering to the canine a canine parvovirus modified-live virus (CPV MLV) and canine parvovirus virus-like particles (CPV VLPs) in an amount effective to overcome a neutralizing effect of maternally derived antibodies (MDAs) against CPV in canines with MDAs to CPV.

15. The method of claim 14, wherein the canine has circulating MDAs effective against CPV.

16. The method of claim 15, wherein the CPV VLPs comprise a polypeptide having 90% or greater sequence identity to at least one of SEQ ID NOs: 1, 3, 4, 6, 8, 9, and 10.

17. The method of claim 15, wherein the CPV VLPs comprise a polypeptide having SEQ ID NO: 1, 3, 4, 6, 8, 9, or 10.

* * * * *

SEQUENCE LISTING

<160> NUMBER OF SEQ ID NOS: 12

<210> SEQ ID NO 1
<211> LENGTH: 584
<212> TYPE: PRT
<213> ORGANISM: Artificial Sequence
<220> FEATURE:
<223> OTHER INFORMATION: VP2 of Canine parvovirus - GenBank BAD34656.1

-continued

```
<400> SEQUENCE: 1

Met Ser Asp Gly Ala Val Gln Pro Asp Gly Gln Pro Ala Val Arg
1               5                   10                  15

Asn Glu Arg Ala Thr Gly Ser Gly Asn Gly Ser Gly Gly Gly Gly
                20                  25                  30

Gly Gly Ser Gly Gly Val Gly Ile Ser Thr Gly Thr Phe Asn Asn Gln
            35                  40                  45

Thr Glu Phe Lys Phe Leu Glu Asn Gly Trp Val Glu Ile Thr Ala Asn
    50                  55                      60

Ser Ser Arg Leu Val His Leu Asn Met Pro Glu Ser Glu Asn Tyr Arg
65              70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
                100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Gln Glu
130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
                180                 185                 190

Glu Thr Leu Gly Phe Tyr Pro Trp Lys Pro Thr Ile Pro Thr Pro Trp
            195                 200                 205

Arg Tyr Tyr Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
                260                 265                 270

Cys Arg Leu Thr His Thr Trp Gln Thr Asn Arg Ala Leu Gly Leu Pro
            275                 280                 285

Pro Phe Leu Asn Ser Leu Pro Gln Ala Glu Gly Gly Thr Asn Phe Gly
            290                 295                 300

Tyr Ile Gly Val Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
            355                 360                 365

Asn Gln Ala Ala Asp Gly Asp Pro Arg Tyr Ala Phe Gly Arg Gln His
            370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
```

```
                    405                 410                 415
Asn Ile Asn Phe Asn Leu Pro Val Thr Glu Asp Asn Val Leu Leu Pro
            420                 425                 430

Thr Asp Pro Ile Gly Gly Lys Thr Gly Ile Asn Tyr Thr Asn Ile Phe
            435                 440                 445

Asn Thr Tyr Gly Pro Leu Thr Ala Leu Asn Asn Val Pro Pro Val Tyr
            450                 455                 460

Pro Asn Gly Gln Ile Trp Asp Lys Glu Phe Thr Asp Leu Lys Pro
465                 470                 475                 480

Arg Leu His Val Asn Ala Pro Phe Val Cys Gln Asn Asn Cys Pro Gly
                    485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
            515                 520                 525

Trp Lys Gly Lys Leu Val Phe Lys Ala Lys Leu Arg Ala Ser His Thr
            530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                    565                 570                 575

Gln Leu Ala Pro Arg Lys Leu Tyr
            580

<210> SEQ ID NO 2
<211> LENGTH: 9632
<212> TYPE: DNA
<213> ORGANISM: Artificial Sequence
<220> FEATURE:
<223> OTHER INFORMATION: pVL1393 - 9632 bp baculovirus transfer vector
      from Invitrogen

<400> SEQUENCE: 2
aagctttact cgtaaagcga gttgaaggat catatttagt tgcgtttatg agataagatt      60
gaaagcacgt gtaaaatgtt tcccgcgcgt tggcacaact atttacaatg cggccaagtt     120
ataaaagatt ctaatctgat atgttttaaa acacctttgc ggcccgagtt gtttgcgtac     180
gtgactagcg aagaagatgt gtggaccgca gaacagatag taaaacaaaa ccctagtatt     240
ggagcaataa tcgatttaac caacacgtct aaatattatg atggtgtgca tttttttgcgg     300 gcgggcctgt tatacaaaaa aattcaagta cctggccaga cttttgccgcc tgaaagcata     360 gttcaagaat ttattgacac ggtaaaagaa tttacagaaa agtgtcccgg catgttggtg     420
ggcgtgcact gcacacacgg tattaatcgc accggttaca tggtgtgcag atatttaatg     480
cacaccctgg gtattgcgcc gcaggaagcc atagatagat cgaaaaagc cagaggtcac     540 aaaattgaaa gacaaaatta cgttcaagat ttattaattt aattaatatt atttgcattc     600
tttaacaaat actttatcct attttcaaat tgttgcgctt cttccagcga accaaaacta     660
tgcttcgctt gctccgttta gcttgtagcc gatcagtggc gttgttccaa tcgacggtag     720
gattaggccg gatattctcc accacaatgt tggcaacgtt gatgttacgt ttatgctttt     780
ggttttccac gtacgtcttt tggccggtaa tagccgtaaa cgtagtgccg tcgcgcgtca     840
cgcacaacac cggatgtttg cgcttgtccg cggggtattg aaccgcgcga tccgacaaat     900
ccaccacttt ggcaactaaa tcggtgacct gcgcgtctt ttttctgcatt atttcgtctt    960 tcttttgcat ggtttcctgg aagccggtgt acatgcggtt tagatcagtc atgacgcgcg   1020
```

```
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat ttttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttttacga agcgatgaca   2520 tgaccccccgt agtgacaacg atcacgccca aagaactgc cgactacaaa attaccgagt   2580
atgtcggtga cgttaaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga agaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaccacca aactgccaaa aatgaaaac tgtcgacaag   3240 ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
```

```
catttgtagt attatctata attgaaaacg cgtagttata atcgctgagg taatatttaa    3420
aatcattttc aaatgattca cagttaatttt gcgacaatat aattttattt tcacataaac   3480
```

```
catttgtagt attatctata attgaaaacg cgtagttata atcgctgagg taatatttaa    3420
aatcattttc aaatgattca cagttaattt gcgacaatat aattttattt tcacataaac    3480
tagacgcctt gtcgtcttct tcttcgtatt ccttctcttt ttcattttc  tcctcataaa    3540
aattaacata gttattatcg tatccatata tgtatctatc gtatagagta aattttttgt    3600
tgtcataaat atatatgtct tttttaatgg ggtgtatagt accgctgcgc atagttttc    3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tcccttttct atactattgt   3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcccgggta   4140
ccttctagaa ttccggagcg gccgctgcag atctgatcct ttcctgggac ccggcaagaa   4200
ccaaaaactc actctcttca aggaaatccg taatgttaaa cccgacacga tgaagcttgt   4260
cgttggatgg aaaggaaaag agttctacag ggaaacttgg acccgcttca tggaagacag   4320
cttccccatt gttaacgacc aagaagtgat ggatgttttc cttgttgtca acatgcgtcc   4380
cactagaccc aaccgttgtt acaaattcct ggcccaacac gctctgcgtt gcgaccccga   4440
ctatgtacct catgacgtga ttaggatcgt cgagccttca tgggtgggca gcaacaacga   4500
gtaccgcatc agcctggcta agaagggcgg cggctgccca ataatgaacc ttcactctga   4560
gtacaccaac tcgttcgaac agttcatcga tcgtgtcatc tgggagaact tctacaagcc   4620
catcgtttac atcggtaccg actctgctga agaggaggaa attctccttg aagtttccct   4680
ggtgttcaaa gtaaaggagt ttgcaccaga cgcacctctg ttcactggtc cggcgtatta   4740
aaacacgata cattgttatt agtacattta ttaagcgcta gattctgtgc gttgttgatt   4800
tacagacaat tgttgtacgt attttaataa ttcattaaat ttataatctt tagggtggta   4860
tgttagagcg aaaatcaaat gattttcagc gtctttatat ctgaatttaa atattaaatc   4920
ctcaatagat ttgtaaaata ggtttcgatt agtttcaaac aagggttgtt tttccgaacc   4980
gatggctgga ctatctaatg gattttcgct caacgccaca aaacttgcca aatcttgtag   5040
cagcaatcta gctttgtcga tattcgtttg ttttgttt   tgtaataaag gttcgacgtc   5100
gttcaaaata ttatgcgctt ttgtatttct ttcatcactg tcgttagtgt acaattgact   5160
cgacgtaaac acgttaaata aagcttggac atatttaaca tcgggcgtgt tagctttatt   5220
aggccgatta tcgtcgtcgt cccaacccct gtcgttagaa gttgcttccg aagacgattt   5280
tgccatagcc acacgacgcc tattaattgt gtcggctaac acgtccgcga tcaaatttgt   5340
agttgagctt tttggaatta tttctgattg cgggcgtttt tgggcgggtt tcaatctaac   5400
tgtgcccgat tttaattcag acaacacgtt agaaagcgat ggtgcaggcg gtggtaacat   5460
ttcagacggc aaatctacta atggcggcgg tggtggagct gatgataaat ctaccatcgg   5520
tggaggcgca ggcggggctg gcggcggagg cggaggcgga ggtggtggcg gtgatgcaga   5580
cggcggttta ggctcaaatg tctctttagg caacacagtc ggcacctcaa ctattgtact   5640
ggtttcgggc gccgttttg gtttgaccgg tctgagacga gtgcgatttt tttcgtttct   5700
aatagcttcc aacaattgtt gtctgtcgtc taaaggtgca gcgggttgag gttccgtcgg   5760
```

```
cattggtgga gcgggcggca attcagacat cgatggtggt ggtggtggtg gaggcgctgg    5820
aatgttaggc acgggagaag gtggtggcgg cggtgccgcc ggtataattt gttctggttt    5880
agtttgttcg cgcacgattg tgggcaccgg cgcaggcgcc gctggctgca acggaagg     5940 tcgtctgctt cgaggcagcg cttggggtgg tggcaattca atattataat tggaatacaa    6000
atcgtaaaaa tctgctataa gcattgtaat ttcgctatcg tttaccgtgc cgatatttaa    6060
caaccgctca atgtaagcaa ttgtattgta aagagattgt ctcaagctcg ccgcacgccg    6120
ataacaagcc ttttcatttt tactacagca ttgtagtggc gagacacttc gctgtcgtcg    6180
acgtacatgt atgctttgtt gtcaaaaacg tcgttggcaa gctttaaaat atttaaaaga    6240
acatctctgt tcagcaccac tgtgttgtcg taaatgttgt ttttgataat ttgcgcttcc    6300
gcagtatcga cacgttcaaa aaattgatgc gcatcaattt tgttgttcct attattgaat    6360
aaataagatt gtacagattc atatctacga ttcgtcatgg ccaccacaaa tgctacgctg    6420
caaacgctgg tacaatttta cgaaaactgc aaaaacgtca aaactcggta taaaataatc    6480
aacgggcgct ttggcaaaat atctatttta tcgcacaagc ccactagcaa attgtatttg    6540
cagaaaacaa tttcggcgca caattttaac gctgacgaaa taaaagttca ccagttaatg    6600
agcgaccacc caaattttat aaaaatctat tttaatcacg gttccatcaa caaccaagtg    6660
atcgtgatgg actacattga ctgtcccgat ttatttgaaa cactacaaat taaaggcgag    6720
ctttcgtacc aacttgttag caatattatt agacagctgt gtgaagcgct caacgatttg    6780
cacaagcaca atttcataca caacgacata aaactcgaaa atgtcttata tttcgaagca    6840
cttgatcgcg tgtatgtttg cgattacgga ttgtgcaaac acgaaaactc acttagcgtg    6900
cacgacggca cgttggagta ttttagtccg gaaaaaattc gacacacaac tatgcacgtt    6960
tcgtttgact ggtacgcggc gtgttaacat acaagttgct aacgtaatca tggtcatagc    7020
tgtttcctgt gtgaaattgt tatccgctca caattccaca caacatacga ccggaagca    7080 taaagtgtaa agcctggggt gcctaatgag tgagctaact cacattaatt gcgttgcgct    7140
cactgcccgc tttccagtcg ggaaacctgt cgtgccagct gcattaatga atcggccaac    7200
gcgcggggag aggcggtttg cgtattgggc gctcttccgc ttcctcgctc actgactcgc    7260
tgcgctcggt cgttcggctg cggcgagcgg tatcagctca ctcaaaggcg gtaatacggt    7320
tatccacaga atcaggggat aacgcaggaa agaacatgtg agcaaaaggc cagcaaaagg    7380
ccaggaaccg taaaaaggcc gcgttgctgg cgttttcca taggctccgc cccctgacg     7440 agcatcacaa aaatcgacgc tcaagtcaga ggtggcgaaa cccgacagga ctataaagat    7500
accaggcgtt ccccctgga agctccctcg tgcgctctcc tgttccgacc ctgccgctta     7560
ccggatacct gtccgccttt ctcccttcgg aagcgtggc gctttctcat agctcacgct    7620
gtaggtatct cagttcggtg taggtcgttc gctccaagct gggctgtgtg cacgaacccc    7680
ccgttcagcc cgaccgctgc gccttatccg gtaactatcg tcttgagtcc aacccggtaa    7740
gacacgactt atcgccactg gcagcagcca ctggtaacag gattagcaga gcgaggtatg    7800
taggcggtgc tacagagttc ttgaagtggt ggcctaacta cggctacact agaaggacag    7860
tatttggtat ctgcgctctg ctgaagccag ttaccttcgg aaaaagagtt ggtagctctt    7920
gatccggcaa acaaaccacc gctggtagcg gtggtttttt tgtttgcaag cagcagatta    7980
cgcgcagaaa aaaaggatct caagaagatc ctttgatctt ttctacgggg tctgacgctc    8040
agtggaacga aaactcacgt taagggattt tggtcatgag attatcaaaa aggatcttca    8100
```

```
cctagatcct tttaaattaa aaatgaagtt ttaaatcaat ctaaagtata tatgagtaaa    8160
cttggtctga cagttaccaa tgcttaatca gtgaggcacc tatctcagcg atctgtctat    8220
ttcgttcatc catagttgcc tgactccccg tcgtgtagat aactacgata cgggagggct    8280
taccatctgg ccccagtgct gcaatgatac cgcgagaccc acgctcaccg gctccagatt    8340
tatcagcaat aaaccagcca gccggaaggg ccgagcgcag aagtggtcct gcaactttat    8400
ccgcctccat ccagtctatt aattgttgcc gggaagctag agtaagtagt tcgccagtta    8460
atagtttgcg caacgttgtt gccattgcta caggcatcgt ggtgtcacgc tcgtcgtttg    8520
gtatggcttc attcagctcc ggttcccaac gatcaaggcg agttacatga tcccccatgt    8580
tgtgcaaaaa agcggttagc tccttcggtc ctccgatcgt tgtcagaagt aagttggccg    8640
cagtgttatc actcatggtt atggcagcac tgcataattc tcttactgtc atgccatccg    8700
taagatgctt ttctgtgact ggtgagtact caaccaagtc attctgagaa tagtgtatgc    8760
ggcgaccgag ttgctcttgc ccggcgtcaa tacgggataa taccgcgcca catagcagaa    8820
ctttaaaagt gctcatcatt ggaaaacgtt cttcggggcg aaaactctca aggatcttac    8880
cgctgttgag atccagttcg atgtaaccca ctcgtgcacc caactgatct tcagcatctt    8940
ttactttcac cagcgtttct gggtgagcaa aaacaggaag gcaaaatgcc gcaaaaaagg    9000
gaataagggc gacacggaaa tgttgaatac tcatactctt ccttttcaa tattattgaa    9060 gcatttatca gggttattgt ctcatgagcg gatacatatt tgaatgtatt tagaaaaata    9120
aacaaatagg ggttccgcgc acatttcccc gaaaagtgcc acctgacgtc taagaaacca    9180
ttattatcat gacattaacc tataaaaata ggcgtatcac gaggcccttt cgtctcgcgc    9240
gtttcggtga tgacggtgaa aacctctgac acatgcagct cccggagacg gtcacagctt    9300
gtctgtaagc ggatgccggg agcagacaag cccgtcaggg cgcgtcagcg ggtgttggcg    9360
ggtgtcgggg ctggcttaac tatgcggcat cagagcagat tgtactgaga gtgcaccata    9420
tgcggtgtga ataccgcac agatgcgtaa ggagaaaata ccgcatcagg cgccattcgc    9480
cattcaggct gcgcaactgt tgggaagggc gatcggtgcg ggcctcttcg ctattacgcc    9540
agctggcgaa aggggggatgt gctgcaaggc gattaagttg ggtaacgcca gggttttccc    9600
agtcacgacg ttgtaaaacg acggccagtg cc                                  9632
```

<210> SEQ ID NO 3
<211> LENGTH: 584
<212> TYPE: PRT
<213> ORGANISM: Artificial Sequence
<220> FEATURE:
<223> OTHER INFORMATION: CPV Souriou (serotype 2c)

<400> SEQUENCE: 3

```
Met Ser Asp Gly Ala Val Gln Pro Asp Gly Gln Pro Ala Val Arg
1               5                   10                  15

Asn Glu Arg Ala Thr Gly Ser Gly Asn Gly Ser Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95
```

```
Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Gln Glu
            130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
            195                 200                 205

Arg Tyr Tyr Phe Gln Trp Asp Arg Thr Leu Ile Pro Ser His Thr Gly
            210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Asp Cys Lys Pro
            260                 265                 270

Cys Arg Leu Thr His Thr Trp Gln Thr Asn Arg Ala Leu Gly Leu Pro
            275                 280                 285

Pro Phe Leu Asn Ser Leu Pro Gln Ala Glu Gly Gly Thr Asn Phe Gly
            290                 295                 300

Tyr Ile Gly Val Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
            355                 360                 365

Asn Gln Ala Ala Asp Gly Asp Pro Arg Tyr Ala Phe Gly Arg Gln His
            370                 375                 380

Gly Gln Lys Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Glu Asp Asn Val Leu Leu Pro
            420                 425                 430

Thr Asp Pro Ile Gly Gly Lys Thr Gly Ile Asn Tyr Thr Asn Ile Phe
            435                 440                 445

Asn Thr Tyr Gly Pro Leu Thr Ala Leu Asn Asn Val Pro Pro Val Tyr
            450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Cys Pro Gly
                485                 490                 495

Gln Leu Phe Val Lys Val Ala Pro Asn Leu Thr Asn Glu Tyr Asp Pro
            500                 505                 510
```

```
Asp Ala Ser Ala Asn Met Ser Arg Ile Val Thr Tyr Ser Asp Phe Trp
            515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                565                 570                 575

Gln Leu Ala Pro Arg Lys Leu Tyr
            580

<210> SEQ ID NO 4
<211> LENGTH: 584
<212> TYPE: PRT
<213> ORGANISM: Artificial Sequence
<220> FEATURE:
<223> OTHER INFORMATION: Non-Truncated CPV VP2 in pMEB072

<400> SEQUENCE: 4

Met Ser Asp Gly Ala Val Gln Pro Asp Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285
```

-continued

```
Pro Phe Leu Asn Ser Leu Pro Gln Ala Glu Gly Gly Thr Asn Phe Gly
        290                 295                 300
Tyr Ile Gly Val Gln Gln Asp Lys Arg Arg Gly Val Thr Gln Met Gly
305                 310                 315                 320
Asn Thr Asn Tyr Ile Thr Glu Ala Thr Ile Met Arg Pro Ala Glu Val
                325                 330                 335
Gly Tyr Ser Ala Pro Tyr Tyr Ser Phe Glu Ala Ser Thr Gln Gly Pro
            340                 345                 350
Phe Lys Thr Pro Ile Ala Ala Gly Arg Gly Gly Ala Gln Thr Asp Glu
        355                 360                 365
Asn Gln Ala Ala Asp Gly Asp Pro Arg Tyr Ala Phe Gly Arg Gln His
    370                 375                 380
Gly Gln Lys Thr Thr Thr Thr Gly Glu Thr Pro Glu Arg Phe Thr Tyr
385                 390                 395                 400
Ile Ala His Gln Asp Thr Gly Arg Tyr Pro Glu Gly Asp Trp Ile Gln
                405                 410                 415
Asn Ile Asn Phe Asn Leu Pro Val Thr Glu Asp Asn Val Leu Leu Pro
            420                 425                 430
Thr Asp Pro Ile Gly Gly Lys Thr Gly Ile Asn Tyr Thr Asn Ile Phe
        435                 440                 445
Asn Thr Tyr Gly Pro Leu Thr Ala Leu Asn Asn Val Pro Pro Val Tyr
    450                 455                 460
Pro Asn Gly Gln Ile Trp Asp Lys Glu Phe Asp Thr Asp Leu Lys Pro
465                 470                 475                 480
Arg Leu His Val Asn Ala Pro Phe Val Cys Gln Asn Asn Cys Pro Gly
                485                 490                 495
Gln Leu Phe Val Lys Val Ala Pro Asn Leu Thr Asn Glu Tyr Asp Pro
            500                 505                 510
Asp Ala Ser Ala Asn Met Ser Arg Ile Val Thr Tyr Ser Asp Phe Trp
        515                 520                 525
Trp Lys Gly Lys Leu Val Phe Lys Ala Lys Leu Arg Ala Ser His Thr
    530                 535                 540
Trp Asn Pro Ile Gln Gln Met Ser Ile Asn Val Asp Asn Gln Phe Asn
545                 550                 555                 560
Tyr Val Pro Ser Asn Ile Gly Gly Met Lys Ile Val Tyr Glu Lys Ser
                565                 570                 575
Gln Leu Ala Pro Arg Lys Leu Tyr
            580
```

<210> SEQ ID NO 5
<211> LENGTH: 1752
<212> TYPE: DNA
<213> ORGANISM: Artificial Sequence
<220> FEATURE:
<223> OTHER INFORMATION: pMEB072 Codon-optimized nucleic acid encoding
   CPV VP2 (SEQ ID NO:4)

<400> SEQUENCE: 5

```
atgtccgacg gtgctgtgca gcccgacggt ggccagcccg ctgtgcgtaa cgagcgtgct      60
accggttccg gtaacggttc aggcggaggt ggaggtggtg gttccggcgg tgtgggcatc     120
tccaccggca ccttcaacaa ccagaccgag ttcaagttcc tcgagaacgg ttgggtggag     180
atcaccgcta actcctcccg tctggtgcac ctgaacatgc ccgagtccga gaactaccgt     240
cgtgtggtgg tgaacaacct ggacaagacc gctgtgaacg gtaacatggc tctggacgac     300
acccacgctc agatcgtgac ccctggtcc ctggtggacg ctaacgcttg gggcgtgtgg     360
```

```
ttcaaccccg gtgactggca gctgatcgtg aacaccatgt ccgagctgca cctggtgtcc    420
ttcgagcaag agatcttcaa cgtcgtcctc aagaccgtgt ccgagtccgc tacccagccc    480
cccaccaagg tgtacaacaa cgacctgacc gcttccctga tggtcgctct ggactccaac    540
aacaccatgc ccttcacccc cgctgctatg cgttccgaga ccctgggctt ctaccccctgg   600
aagcccacca tccccacccc ctggcgttac tacttccagt gggaccgtac cctgatcccc    660
tcccacaccg gtacttccgg caccccccacc aacatctacc acggcaccga ccccgacgac   720
gtgcagttct acaccatcga gaactccgtg cccgtgcacc tgctgcgtac cggtgacgag    780
ttcgctaccg gaaccttctt cttcgactgc aagcccgcc  gtctgaccca cctggcag     840
accaaccgtg ctctgggtct gcctcccttc ctgaactccc tgccccaggc tgagggtggc    900
accaacttcg gttacatcgg tgtgcagcag gacaagcgtc gtggtgtgac ccagatgggt    960
aacaccaact acatcaccga ggctaccatc atgcgtcccg ctgaggtcgg ctactccgct   1020
ccctactact cctttcgaggc ttccacccag ggccccttca agaccccccat cgctgctggt  1080
cgtggtggtg ctcagaccga cgagaaccag gctgctgacg tgaccccccg ttacgctttc   1140
ggtcgtcagc acggccaaaa gaccaccacc accggcgaga cccccgagcg tttcacctac   1200
atcgctcacc aggacaccgg tcgttacccc gagggcgact ggattcagaa catcaacttc   1260
aacctgcccg tgaccgagga caacgtgctg ctgcccaccg accccatcgg tggcaagacc   1320
ggtatcaact acactaacat cttcaacacc tacggtcctc tgaccgctct gaacaacgtg   1380
ccccccgtgt accccaacgg ccagatctgg gacaaggagt cgacaccga  cctgaagccc   1440
cgtctgcacg tgaacgctcc cttcgtgtgc cagaacaact gccctggcca gctgttcgtc   1500
aaggtggccc ccaacctgac caacgagtac gaccctgacg cttccgctaa catgtcccgt   1560
atcgtgacct actccgactt ctggtggaag ggcaagctgg tgttcaaggc caagctgcgt   1620
gcttctcaca cctggaaccc catccagcag atgtccatca cgtggacaa ccagttcaac    1680
tacgtgccct ccaacatcgg tggaatgaag atcgtgtacg agaagtccca gctggctccc   1740
cgtaagctgt ac                                                       1752
```

<210> SEQ ID NO 6
<211> LENGTH: 578
<212> TYPE: PRT
<213> ORGANISM: Artificial Sequence
<220> FEATURE:
<223> OTHER INFORMATION: Truncated CPV VP2 in pMEB073

<400> SEQUENCE: 6

```
Met Leu Lys Gly Gly Gln Pro Ala Val Arg Asn Glu Arg Ala Thr Gly
1               5                   10                  15

Ser Gly Asn Gly Ser Gly Gly Gly Gly Gly Ser Gly Gly Val
            20                  25                  30

Gly Ile Ser Thr Gly Thr Phe Asn Asn Gln Thr Glu Phe Lys Phe Leu
        35                  40                  45

Glu Asn Gly Trp Val Glu Ile Thr Ala Asn Ser Ser Arg Leu Val His
    50                  55                  60

Leu Asn Met Pro Glu Ser Glu Asn Tyr Arg Arg Val Val Asn Asn
65                  70                  75                  80

Leu Asp Lys Thr Ala Val Asn Gly Asn Met Ala Leu Asp Asp Thr His
                85                  90                  95

Ala Gln Ile Val Thr Pro Trp Ser Leu Val Asp Ala Asn Ala Trp Gly
            100                 105                 110
```

-continued

```
Val Trp Phe Asn Pro Gly Asp Trp Gln Leu Ile Val Asn Thr Met Ser
        115                 120                 125

Glu Leu His Leu Val Ser Phe Glu Gln Gly Ile Phe Asn Val Val Leu
    130                 135                 140

Lys Thr Val Ser Glu Ser Ala Thr Gln Pro Pro Thr Lys Val Tyr Asn
145                 150                 155                 160

Asn Asp Leu Thr Ala Ser Leu Met Val Ala Leu Asp Ser Asn Asn Thr
                    165                 170                 175

Met Pro Phe Thr Pro Ala Ala Met Arg Ser Glu Thr Leu Gly Phe Tyr
            180                 185                 190

Pro Trp Lys Pro Thr Ile Pro Thr Pro Trp Arg Tyr Tyr Phe Gln Trp
        195                 200                 205

Asp Arg Thr Leu Ile Pro Ser His Thr Gly Thr Ser Gly Thr Pro Thr
    210                 215                 220

Asn Ile Tyr His Gly Thr Asp Pro Asp Asp Val Gln Phe Tyr Thr Ile
225                 230                 235                 240

Glu Asn Ser Val Pro Val His Leu Leu Arg Thr Gly Asp Glu Phe Ala
                    245                 250                 255

Thr Gly Thr Phe Phe Phe Asp Cys Lys Pro Cys Arg Leu Thr His Thr
            260                 265                 270

Trp Gln Thr Asn Arg Ala Leu Gly Leu Pro Pro Phe Leu Asn Ser Leu
        275                 280                 285

Pro Gln Ala Glu Gly Gly Thr Asn Phe Gly Tyr Ile Gly Val Gln Gln
    290                 295                 300

Asp Lys Arg Arg Gly Val Thr Gln Met Gly Asn Thr Asn Tyr Ile Thr
305                 310                 315                 320

Glu Ala Thr Ile Met Arg Pro Ala Glu Val Gly Tyr Ser Ala Pro Tyr
                    325                 330                 335

Tyr Ser Phe Glu Ala Ser Thr Gln Gly Pro Phe Lys Thr Pro Ile Ala
            340                 345                 350

Ala Gly Arg Gly Gly Ala Gln Thr Asp Glu Asn Gln Ala Ala Asp Gly
        355                 360                 365

Asp Pro Arg Tyr Ala Phe Gly Arg Gln His Gly Gln Lys Thr Thr Thr
    370                 375                 380

Thr Gly Glu Thr Pro Glu Arg Phe Thr Tyr Ile Ala His Gln Asp Thr
385                 390                 395                 400

Gly Arg Tyr Pro Glu Gly Asp Trp Ile Gln Asn Ile Asn Phe Asn Leu
                    405                 410                 415

Pro Val Thr Glu Asp Asn Val Leu Leu Pro Thr Asp Pro Ile Gly Gly
            420                 425                 430

Lys Thr Gly Ile Asn Tyr Thr Asn Ile Phe Asn Thr Tyr Gly Pro Leu
        435                 440                 445

Thr Ala Leu Asn Asn Val Pro Pro Val Tyr Pro Asn Gly Gln Ile Trp
    450                 455                 460

Asp Lys Glu Phe Asp Thr Asp Leu Lys Pro Arg Leu His Val Asn Ala
465                 470                 475                 480

Pro Phe Val Cys Gln Asn Asn Cys Pro Gly Gln Leu Phe Val Lys Val
                    485                 490                 495

Ala Pro Asn Leu Thr Asn Glu Tyr Asp Pro Asp Ala Ser Ala Asn Met
            500                 505                 510

Ser Arg Ile Val Thr Tyr Ser Asp Phe Trp Trp Lys Gly Lys Leu Val
        515                 520                 525
```

```
Phe Lys Ala Lys Leu Arg Ala Ser His Thr Trp Asn Pro Ile Gln Gln
        530                 535                 540
Met Ser Ile Asn Val Asp Asn Gln Phe Asn Tyr Val Pro Ser Asn Ile
545                 550                 555                 560
Gly Gly Met Lys Ile Val Tyr Glu Lys Ser Gln Leu Ala Pro Arg Lys
                565                 570                 575
Leu Tyr
```

<210> SEQ ID NO 7
<211> LENGTH: 1536
<212> TYPE: DNA
<213> ORGANISM: Artificial Sequence
<220> FEATURE:
<223> OTHER INFORMATION: pMEB073 codon-optimized nucleic acid sequence
     encoding CPV VP2 (SEQ ID NO:6)

<400> SEQUENCE: 7

```
atgcccgaga gcgagaacta ccggagagtg gtggtgaaca acctggacaa gaccgccgtg      60
aacggcaata tggccctgga tgacacccac gcccagatcg tgacccctg gagcctggtg     120
gacgccaacg cctggggagt gtggttcaac cctggcgact ggcagctgat cgtgaacacc     180
atgagcgagc tgcacctggt gtccttcgag caggagattt tcaacgtggt gctgaaaacc     240
gtgtccgaga gcgccaccca gccccccacc aaagtgtaca acaacgacct gaccgcctcc     300
ctgatggtgg ccctggacag caacaacacc atgcccttca cccctgccgc catgagaagc     360
gagaccctgg gcttctaccc ttggaagccc accatcccca cccttggcg gtactacttc     420
cagtgggaca ggaccctgat ccccagccac accggcacca gcggcacccc taccaatatc     480
taccacggca ccgaccctga tgacgtgcag ttctacacca tcgagaacag cgtgcctgtg     540
cacctgctga gaaccggcga cgagttcgcc accggacat tcttcttcga ctgcaagccc     600
tgcagactga cccacacctg gcagaccaac agagccctgg gcctgcctcc tttcctgaac     660
agcctgcccc aggccgaggg cggcaccaac ttcggctaca tcggcgtgca gcaggacaag     720
agaagaggcg tgacccagat gggcaacacc aactacatca ccgaggccac catcatgaga     780
cccgccgaag tgggctacag cgccccctac tacagcttcg aggccagcac ccagggcccc     840
ttcaagaccc ccatcgccgc tggcagaggc ggagcccaga ccgacgagaa ccaggccgcc     900
gacgccgacc ccagatacgc cttcggcaga cagcacggcc agaaaaccac caccaccggc     960
gagacccccg agagattcac ctacatcgcc caccaggaca ccggcagata ccccgagggc    1020
gactggattc agaacatcaa cttcaacctg cccgtgaccg aggataatgt gctgctgccc    1080
accgacccca tcggcggcaa gaccggcatc aactacacca catcttcaa cacctacggc    1140
cccctgaccg ccctgaataa cgtgcccccc gtgtaccccca acggccagat ttgggacaag    1200
gagttcgaca ccgacctgaa gcctaggctg cacgtgaatg ccccctttcgt gtgtcagaac    1260
aactgccctg gccagctgtt tgtgaaagtg gccccaacc tgaccaacga gtacgatcct    1320
gacgccagcg ccaacatgag ccggatcgtg acctacagcg acttctggtg gaagggcaag    1380
ctggtgttca aggccaagct gagagccagc cacacatgga cccccatcca gcagatgagc    1440
atcaacgtgg acaaccagtt caactacgtg cccagcaata tcggcggcat gaagatcgtg    1500
tacgagaaga gccagctggc ccccagaaag ctgtac                             1536
```

<210> SEQ ID NO 8
<211> LENGTH: 584
<212> TYPE: PRT
<213> ORGANISM: Artificial Sequence
<220> FEATURE:
<223> OTHER INFORMATION: GenBank: AHW47988.1

<400> SEQUENCE: 8

```
Met Ser Asp Gly Ala Val Gln Pro Asp Gly Gln Pro Ala Val Arg
 1               5                  10                  15

Asn Glu Arg Ala Thr Gly Ser Gly Asn Gly Ser Gly Gly Gly Gly
                20                  25                  30

Gly Gly Ser Gly Gly Val Gly Ile Ser Thr Gly Thr Phe Asn Asn Gln
            35                  40                  45

Thr Glu Phe Lys Phe Leu Glu Asn Gly Trp Val Glu Ile Thr Ala Asn
 50                  55                  60

Ser Ser Arg Leu Val His Leu Asn Met Pro Glu Ser Glu Asn Tyr Lys
 65                  70                  75                  80

Arg Val Val Val Asn Asn Met Asp Lys Thr Ala Val Lys Gly Asn Met
                    85                  90                  95

Ala Leu Asp Asp Thr His Val Gln Ile Val Thr Pro Trp Ser Leu Val
                100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Arg Glu
130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
210                 215                 220

Thr Ser Gly Thr Pro Thr Asn Val Tyr His Gly Ser Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Ile Thr Asn Phe Gly
290                 295                 300

Asp Ile Gly Val Gln Gln Asp Lys Arg Arg Gly Val Thr Gln Met Gly
305                 310                 315                 320

Asn Thr Asp Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Lys Tyr Ala Phe Gly Arg Gln His
370                 375                 380

Gly Gln Lys Thr Thr Thr Thr Gly Glu Thr Pro Glu Arg Phe Thr Tyr
385                 390                 395                 400
```

-continued

```
Ile Ala His Gln Asp Thr Gly Arg Tyr Pro Glu Gly Asp Trp Ile Gln
            405                 410                 415

Asn Ile Asn Phe Asn Leu Pro Val Thr Lys Asp Asn Val Leu Leu Pro
        420                 425                 430

Thr Asp Pro Ile Gly Gly Lys Thr Gly Ile Asn Tyr Thr Asn Ile Phe
    435                 440                 445

Asn Thr Tyr Gly Pro Leu Thr Ala Leu Asn Asn Val Pro Pro Val Tyr
450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
            485                 490                 495

Gln Leu Phe Val Lys Val Ala Pro Asn Leu Thr Asn Glu Tyr Asp Pro
        500                 505                 510

Asp Ala Ser Ala Asn Met Ser Arg Ile Val Thr Tyr Ser Asp Phe Trp
    515                 520                 525

Trp Lys Gly Lys Leu Val Phe Lys Ala Lys Leu Arg Ala Ser His Thr
530                 535                 540

Trp Asn Pro Ile Gln Gln Met Ser Ile Asn Val Asp Asn Gln Phe Asn
545                 550                 555                 560

Tyr Val Pro Asn Asn Ile Gly Ala Met Lys Ile Val Tyr Glu Lys Ser
            565                 570                 575

Gln Leu Ala Pro Arg Lys Leu Tyr
            580
```

<210> SEQ ID NO 9
<211> LENGTH: 584
<212> TYPE: PRT
<213> ORGANISM: Artificial Sequence
<220> FEATURE:
<223> OTHER INFORMATION: GenBank: AHW47989.1

<400> SEQUENCE: 9

```
Met Ser Asp Gly Ala Val Gln Pro Asp Gly Gln Pro Ala Val Arg
1               5                   10                  15

Asn Glu Arg Ala Thr Gly Ser Gly Asn Gly Ser Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Lys
65                  70                  75                  80

Arg Val Val Val Asn Asn Met Asp Lys Thr Ala Val Lys Gly Asn Met
            85                  90                  95

Ala Leu Asp Asp Thr His Val Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
            165                 170                 175
```

```
Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Val Tyr His Gly Ser Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Ile Thr Asn Phe Gly
    290                 295                 300

Asp Ile Gly Val Gln Gln Asp Lys Arg Arg Gly Val Thr Gln Met Gly
305                 310                 315                 320

Asn Thr Asp Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Lys Tyr Ala Phe Gly Arg Gln His
    370                 375                 380

Gly Gln Lys Thr Thr Thr Gly Glu Thr Pro Glu Arg Phe Thr Tyr
385                 390                 395                 400

Ile Ser His Gln Asp Thr Gly Arg Tyr Pro Glu Gly Asp Trp Ile Gln
                405                 410                 415

Asn Ile Asn Phe Asn Leu Pro Val Thr Lys Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Asn Asn Ile Gly Ala Met Lys Ile Val Tyr Glu Lys Ser
                565                 570                 575

Gln Leu Ala Pro Arg Lys Leu Tyr
            580
```

<210> SEQ ID NO 10
<211> LENGTH: 584
<212> TYPE: PRT
<213> ORGANISM: Artificial Sequence
<220> FEATURE:
<223> OTHER INFORMATION: GenBank: ADA61118.1

<400> SEQUENCE: 10

Met Ser Asp Gly Ala Val Gln Pro Asp Gly Gln Pro Ala Val Arg
1               5                   10                  15

Asn Glu Arg Ala Thr Gly Ser Gly Asn Gly Ser Gly Gly Gly Gly
                20                  25                  30

Gly Gly Ser Gly Gly Gly Ile Ser Thr Gly Ala Phe Asn Asn Gln
            35                  40                  45

Thr Glu Phe Lys Phe Leu Glu Asn Gly Trp Val Glu Ile Thr Ala Asn
        50                  55                  60

Ser Ser Arg Leu Val His Leu Asn Met Pro Glu Ser Glu Asn Tyr Arg
65                  70                  75                  80

Arg Val Val Val Asn Asn Met Asp Lys Thr Ala Val Asn Gly Asn Met
                    85                  90                  95

Ala Leu Asp Asp Ile His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr His Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Asp Cys Thr Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ser Glu Gly Ala Thr Asn Phe Gly
    290                 295                 300

Asp Ile Gly Val Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

```
Asn Gln Ala Ala Asp Gly Glu Pro Arg Tyr Ala Phe Gly Arg Gln His
    370                 375                 380
Gly Gln Lys Thr Thr Thr Thr Gly Glu Thr Pro Glu Arg Phe Thr Tyr
385                 390                 395                 400
Ile Ala His Gln Asp Thr Gly Arg Tyr Pro Glu Gly Asp Trp Ile Gln
                405                 410                 415
Asn Ile Asn Phe Asn Leu Pro Val Thr Asn Asp Asn Val Leu Leu Pro
            420                 425                 430
Thr Asp Pro Ile Gly Gly Lys Thr Gly Ile Asn Tyr Thr Asn Ile Phe
        435                 440                 445
Asn Thr Tyr Gly Pro Leu Thr Ala Leu Asn Asn Val Pro Pro Val Tyr
    450                 455                 460
Pro Asn Gly Gln Ile Trp Asp Lys Glu Phe Asp Thr Asp Leu Lys Pro
465                 470                 475                 480
Arg Leu His Val Asn Ala Pro Phe Val Cys Gln Asn Asn Cys Pro Gly
                485                 490                 495
Gln Leu Phe Val Lys Val Ala Pro Asn Leu Thr Asn Glu Tyr Asp Pro
            500                 505                 510
Asp Ala Ser Ala Asn Met Ser Arg Ile Val Thr Tyr Ser Asp Phe Trp
        515                 520                 525
Trp Lys Gly Lys Leu Val Phe Lys Ala Lys Leu Arg Ala Ser His Thr
    530                 535                 540
Trp Asn Pro Ile Gln Gln Met Ser Ile Asn Val Asp Asn Gln Phe Asn
545                 550                 555                 560
Tyr Val Pro Ser Asn Ile Gly Gly Met Lys Ile Val Phe Glu Lys Ser
                565                 570                 575
Gln Leu Ala Pro Arg Lys Leu Tyr
            580

<210> SEQ ID NO 11
<211> LENGTH: 11387
<212> TYPE: DNA
<213> ORGANISM: Artificial Sequence
<220> FEATURE:
<223> OTHER INFORMATION: pMEB072

<400> SEQUENCE: 11
aagctttact cgtaaagcga gttgaaggat catatttagt tgcgtttatg agataagatt    60
gaaagcacgt gtaaaatgtt tcccgcgcgt tggcacaact atttacaatg cggccaagtt   120 ataaagatt ctaatctgat atgttttaaa acacctttgc ggcccgagtt gtttgcgtac    180
gtgactagcg aagaagatgt gtggaccgca gaacagatag taaaacaaaa ccctagtatt   240
ggagcaataa tcgatttaac caacacgtct aaatattatg atggtgtgca ttttttgcgg   300
gcgggcctgt tatacaaaaa aattcaagta cctggccaga cttgccgcc  tgaaagcata   360 gttcaagaat ttattgacac ggtaaaagaa tttacagaaa agtgtcccgg catgttggtg   420
ggcgtgcact gcacacacgg tattaatcgc accggttaca tggtgtgcag atatttaatg   480
cacaccctgg gtattgcgcc gcaggaagcc atagatagat cgaaaaagc cagaggtcac    540 aaaattgaaa gacaaaatta cgttcaagat ttattaattt aattaatatt atttgcattc   600
tttaacaaat actttatcct attttcaaat tgttgcgctt cttccagcga accaaaacta   660
tgcttcgctt gctccgttta gcttgtagcc gatcagtggc gttgttccaa tcgacggtag   720
gattaggccg atattctcc accacaatgt tggcaacgtt gatgttacgt ttatgctttt   780
ggttttccac gtacgtcttt tggccggtaa tagccgtaaa cgtagtgccg tcgcgcgtca   840
```

```
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactcccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgaccccgt agtgacaacg atcacgccca aagaactgc cgactacaaa attaccgagt   2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga agaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
```

```
atcaaatccc aagatgtgta taaaccacca aactgccaaa aaatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aattttattt tcacataaac    3480
tagacgcctt gtcgtcttct tcttcgtatt ccttctcttt ttcattttc tcctcataaa     3540
aattaacata gttattatcg tatccatata tgtatctatc gtatagagta aatttttgt     3600
tgtcataaat atatatgtct tttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta ataactttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atccgccacc    4140
atgtccgacg gtgctgtgca gcccgacggt ggccagcccg ctgtgcgtaa cgagcgtgct    4200
accggttccg gtaacggttc aggcggaggt ggaggtggtg gttccggcgg tgtgggcatc    4260
tccaccggca ccttcaacaa ccagaccgag ttcaagttcc tcgagaacgg ttgggtggag    4320
atcaccgcta actcctcccg tctggtgcac ctgaacatgc ccgagtccga gaactaccgt    4380
cgtgtggtgg tgaacaacct ggacaagacc gctgtgaacg gtaacatggc tctggacgac    4440
acccacgctc agatcgtgac ccctggtcc ctggtggacg ctaacgcttg ggcgtgtgg     4500
ttcaaccccg gtgactggca gctgatcgtg aacaccatgt ccgagctgca cctggtgtcc    4560
ttcgagcaag agatcttcaa cgtcgtcctc aagaccgtgt ccgagtccgc tacccagccc    4620
cccaccaagg tgtacaacaa cgacctgacc gcttccctga tggtcgctct ggactccaac    4680
aacaccatgc ccttcacccc cgctgctatg cgttccgaga ccctgggctt ctaccctgg    4740
aagccccca tccccacccc ctggcgttac tacttccagt gggaccgtac cctgatcccc    4800
tcccacaccg gtacttccgg caccccccacc aacatctacc acggcaccga ccccgacgac   4860
gtgcagttct acaccatcga gaactccgtg cccgtgcacc tgctgcgtac cggtgacgag    4920
ttcgctaccg gaaccttctt cttcgactgc aagccctgcc gtctgaccca cctggcag     4980
accaaccgtg ctctgggtct gcctcccttc ctgaactccc tgcccaggc tgagggtggc    5040
accaacttcg gttacatcgg tgtgcagcag gacaagcgtc gtggtgtgac ccagatgggt    5100
aacaccaact acatcaccga ggctaccatc atgcgtcccg ctgaggtcgg ctactccgct    5160
ccctactact ccttcgaggc ttccacccag ggccccttca agaccccat cgctgctggt    5220
cgtggtggtg ctcagaccga cgagaaccag gctgctgacg tgaccccccg ttacgctttc    5280
ggtcgtcagc acggccaaaa gaccaccacc accggcgaga cccccgagcg tttcaccta    5340
atcgctcacc aggacaccgg tcgttacccc gagggcgact ggattcagaa catcaactc    5400
aacctgcccg tgaccgagga caacgtgctg ctgcccaccg acccccatcg tggcaagacc    5460
ggtatcaact acactaacat cttcaacacc tacggtcctc tgaccgctct gaacaacgtg    5520
cccccccgtgt accccaacgg ccagatctgg gacaaggagt tcgacaccga cctgaagccc    5580
```

```
cgtctgcacg tgaacgctcc cttcgtgtgc cagaacaact gccctggcca gctgttcgtc   5640
aaggtggccc ccaacctgac caacgagtac gaccctgacg cttccgctaa catgtcccgt   5700
atcgtgacct actccgactt ctggtggaag ggcaagctgg tgttcaaggc caagctgcgt   5760
gcttctcaca cctggaaccc catccagcag atgtccatca acgtggacaa ccagttcaac   5820
tacgtgccct ccaacatcgg tggaatgaag atcgtgtacg agaagtccca gctggctccc   5880
cgtaagctgt actaataatc tagaattccg gagcggccgc tgcagatctg atcctttcct   5940
gggacccggc aagaaccaaa aactcactct cttcaaggaa atccgtaatg ttaaacccga   6000
cacgatgaag cttgtcgttg gatggaaagg aaaagagttc tacagggaaa cttggacccg   6060
cttcatggaa gacagcttcc ccattgttaa cgaccaagaa gtgatggatg ttttccttgt   6120
tgtcaacatg cgtcccacta gacccaaccg ttgttacaaa ttcctggccc aacacgctct   6180
gcgttgcgac cccgactatg tacctcatga cgtgattagg atcgtcgagc cttcatgggt   6240
gggcagcaac aacgagtacc gcatcagcct ggctaagaag ggcggcggct gcccaataat   6300
gaaccttcac tctgagtaca ccaactcgtt cgaacagttc atcgatcgtg tcatctggga   6360
gaacttctac aagcccatcg tttacatcgg taccgactct gctgaagagg aggaaattct   6420
ccttgaagtt tccctggtgt tcaaagtaaa ggagtttgca ccagacgcac ctctgttcac   6480
tggtccggcg tattaaaaca cgatacattg ttattagtac atttattaag cgctagattc   6540
tgtgcgttgt tgatttacag acaattgttg tacgtatttt aataattcat taaatttata   6600
atctttaggg tggtatgtta gagcgaaaat caaatgattt tcagcgtctt tatatctgaa   6660
tttaaatatt aaatcctcaa tagatttgta aaataggttt cgattagttt caaacaaggg   6720 ttgttttttcc gaaccgatgg ctggactatc taatggattt tcgctcaacg ccacaaaact   6780
tgccaaatct tgtagcagca atctagcttt gtcgatattc gtttgtgttt tgttttgtaa   6840
taaaggttcg acgtcgttca aaatatatg cgcttttgta tttctttcat cactgtcgtt   6900
agtgtacaat tgactcgacg taaacacgtt aaataaagct tggacatatt taacatcggg   6960
cgtgttagct ttattaggcc gattatcgtc gtcgtcccaa ccctcgtcgt tagaagttgc   7020
ttccgaagac gattttgcca tagccacacg acgcctatta attgtgtcgg ctaacacgtc   7080
cgcgatcaaa tttgtagttg agcttttttgg aattatttct gattgcgggc gttttttgggc   7140 gggtttcaat ctaactgtgc ccgatttttaa ttcagacaac acgttagaaa gcgatggtgc   7200
aggcggtggt aacatttcag acggcaaatc tactaatggc ggcggtggtg gagctgatga   7260
taaatctacc atcggtggag gcgcaggcgg ggctggcggc ggaggcggag gcggaggtgg   7320
tggcggtgat gcagacggcg gtttaggctc aaatgtctct ttaggcaaca cagtcggcac   7380
ctcaactatt gtactggttt cgggcgccgt ttttggtttg accggtctga gacgagtgcg   7440
atttttttcg tttctaatag cttccaacaa ttgttgtctg tcgtctaaag gtgcagcggg   7500
ttgaggttcc gtcggcattg gtggagcggg cggcaattca gacatcgatg gtggtggtgg   7560
tggtggaggc gctggaatgt taggcacggg agaaggtggt ggcggcggtg ccgccggtat   7620
aatttgttct ggtttagttt gttcgcgcac gattgtgggc accggcgcag gcgccgctgg   7680
ctgcacaacg gaaggtcgtc tgcttcgagg cagcgcttgg ggtggtggca attcaatatt   7740
ataattggaa tacaaatcgt aaaaatctgc tataagcatt gtaatttcgc tatcgtttac   7800
cgtgccgata tttaacaacc gctcaatgta agcaattgta ttgtaaagag attgtctcaa   7860
gctcgccgca cgccgataac aagccttttc attttttacta cagcattgta gtggcgagac   7920
```

```
acttcgctgt cgtcgacgta catgtatgct ttgttgtcaa aaacgtcgtt ggcaagcttt    7980
aaaatattta aaagaacatc tctgttcagc accactgtgt tgtcgtaaat gttgtttttg    8040
ataatttgcg cttccgcagt atcgacacgt tcaaaaaatt gatgcgcatc aattttgttg    8100
ttcctattat tgaataaata agattgtaca gattcatatc tacgattcgt catggccacc    8160
acaaatgcta cgctgcaaac gctggtacaa ttttacgaaa actgcaaaaa cgtcaaaact    8220
cggtataaaa taatcaacgg gcgctttggc aaaatatcta ttttatcgca caagcccact    8280
agcaaattgt atttgcagaa aacaatttcg gcgcacaatt ttaacgctga cgaaataaaa    8340
gttcaccagt taatgagcga ccacccaaat tttataaaaa tctatttaaa tcacggttcc    8400
atcaacaacc aagtgatcgt gatggactac attgactgtc ccgatttatt tgaaacacta    8460
caaattaaag gcgagctttc gtaccaactt gttagcaata ttattagaca gctgtgtgaa    8520
gcgctcaacg atttgcacaa gcacaatttc atacacaacg ataaaaact cgaaaatgtc     8580
ttatatttcg aagcacttga tcgcgtgtat gtttgcgatt acggattgtg caaacacgaa    8640
aactcactta gcgtgcacga cggcacgttg gagtatttta gtccggaaaa aattcgacac    8700
acaactatgc acgtttcgtt tgactggtac gcggcgtgtt aacatacaag ttgctaacgt    8760
aatcatggtc atagctgttt cctgtgtgaa attgttatcc gctcacaatt ccacacaaca    8820
tacgagccgg aagcataaag tgtaaagcct ggggtgccta atgagtgagc taactcacat    8880
taattgcgtt gcgctcactg cccgctttcc agtcgggaaa cctgtcgtgc cagctgcatt    8940
aatgaatcgg ccaacgcgcg gggagaggcg gtttgcgtat tgggcgctct tccgcttcct    9000
cgctcactga ctcgctgcgc tcggtcgttc ggctgcggcg agcggtatca gctcactcaa    9060
aggcggtaat acggttatcc acagaatcag gggataacgc aggaaagaac atgtgagcaa    9120
aaggccagca aaaggccagg aaccgtaaaa aggccgcgtt gctggcgttt ttccataggc    9180
tccgcccccc tgacgagcat cacaaaaatc gacgctcaag tcagaggtgg cgaaacccga    9240
caggactata aagataccag gcgtttcccc ctggaagctc cctcgtgcgc tctcctgttc    9300
cgaccctgcc gcttaccgga tacctgtccg cctttctccc ttcgggaagc gtggcgcttt    9360
ctcatagctc acgctgtagg tatctcagtt cggtgtaggt cgttcgctcc aagctgggct    9420
gtgtgcacga accccccgtt cagcccgacc gctgcgcctt atccggtaac tatcgtcttg    9480
agtccaaccc ggtaagacac gacttatcgc cactggcagc agccactggt aacaggatta    9540
gcagagcgag gtatgtaggc ggtgctacag agttcttgaa gtggtggcct aactacggct    9600
acactagaag gacagtattt ggtatctgcg ctctgctgaa gccagttacc ttcggaaaaa    9660
gagttggtag ctcttgatcc ggcaaacaaa ccaccgctgg tagcggtggt ttttttgttt    9720
gcaagcagca gattacgcgc agaaaaaaag gatctcaaga agatcctttg atcttttcta    9780
cggggtctga cgctcagtgg aacgaaaact cacgttaagg gattttggtc atgagattat    9840
caaaaaggat cttcacctag atccttttaa attaaaaatg aagttttaaa tcaatctaaa    9900
gtatatatga gtaaacttgg tctgacagtt accaatgctt aatcagtgag gcacctatct    9960
cagcgatctg tctatttcgt tcatccatag ttgcctgact ccccgtcgtg tagataacta   10020
cgatacggga gggcttacca tctggcccca gtgctgcaat gataccgcga gacccacgct   10080
caccggctcc agatttatca gcaataaacc agccagccgg aagggccgag cgcagaagtg   10140
gtcctgcaac tttatccgcc tccatccagt ctattaattg ttgccgggaa gctagagtaa   10200
gtagttcgcc agttaatagt ttgcgcaacg ttgttgccat tgctacaggc atcgtggtgt   10260
cacgctcgtc gtttggtatg gcttcattca gctccggttc ccaacgatca aggcgagtta   10320
```

```
catgatcccc catgttgtgc aaaaaagcgg ttagctcctt cggtcctccg atcgttgtca    10380
gaagtaagtt ggccgcagtg ttatcactca tggttatggc agcactgcat aattctctta    10440
ctgtcatgcc atccgtaaga tgcttttctg tgactggtga gtactcaacc aagtcattct    10500
gagaatagtg tatgcggcga ccgagttgct cttgcccggc gtcaatacgg gataataccg    10560
cgccacatag cagaacttta aaagtgctca tcattggaaa acgttcttcg gggcgaaaac    10620
tctcaaggat cttaccgctg ttgagatcca gttcgatgta acccactcgt gcacccaact    10680
gatcttcagc atcttttact ttcaccagcg tttctgggtg agcaaaaaca ggaaggcaaa    10740
atgccgcaaa aaagggaata agggcgacac ggaaatgttg aatactcata ctcttccttt    10800
ttcaatatta ttgaagcatt tatcagggtt attgtctcat gagcggatac atatttgaat    10860
gtatttagaa aaataaacaa ataggggttc cgcgcacatt tccccgaaaa gtgccacctg    10920
acgtctaaga aaccattatt atcatgacat taacctataa aaataggcgt atcacgaggc    10980
cctttcgtct cgcgcgtttc ggtgatgacg gtgaaaacct ctgacacatg cagctcccgg    11040
agacggtcac agcttgtctg taagcggatg ccggagcag acaagcccgt cagggcgcgt    11100
cagcgggtgt tggcgggtgt cggggctggc ttaactatgc ggcatcagag cagattgtac    11160
tgagagtgca ccatatgcgg tgtgaaatac cgcacagatg cgtaaggaga aaataccgca    11220
tcaggcgcca ttcgccattc aggctgcgca actgttggga agggcgatcg gtgcgggcct    11280
cttcgctatt acgccagctg gcgaaagggg gatgtgctgc aaggcgatta agttgggtaa    11340
cgccagggtt ttcccagtca cgacgttgta aaacgacggc cagtgcc                 11387
```

<210> SEQ ID NO 12
<211> LENGTH: 11385
<212> TYPE: DNA
<213> ORGANISM: Artificial Sequence
<220> FEATURE:
<223> OTHER INFORMATION: pMEB073

<400> SEQUENCE: 12

```
ctagaattcc ggagcggccg ctgcagatct gatcctttcc tgggacccgg caagaaccaa      60
aaactcactc tcttcaagga aatccgtaat gttaaacccg acacgatgaa gcttgtcgtt     120
ggatggaaag gaaagagagtt ctacagggaa acttggaccc gcttcatgga agacagcttc    180
cccattgtta acgaccaaga agtgatggat gttttccttg ttgtcaacat gcgtcccact     240
agacccaacc gttgttacaa attcctggcc caacacgctc tgcgttgcga ccccgactat     300
gtacctcatg acgtgattag gatcgtcgag ccttcatggg tgggcagcaa caacgagtac     360
cgcatcagcc tggctaagaa gggcggcggc tgcccaataa tgaaccttca ctctgagtac     420
accaactcgt tcgaacagtt catcgatcgt gtcatctggg agaacttcta caagcccatc     480
gtttacatcg gtaccgactc tgctgaagag gaggaaattc tccttgaagt ttccctggtg     540
ttcaaagtaa aggagtttgc accagacgca cctctgttca ctggtccggc gtattaaaac     600
acgatacatt gttattagta catttattaa gcgctagatt ctgtgcgttg ttgatttaca     660
gacaattgtt gtacgtattt taataattca ttaaatttat aatctttagg gtggtatgtt     720
agagcgaaaa tcaaatgatt ttcagcgtct ttatatctga atttaaatat taaatcctca     780
atagatttgt aaaataggtt tcgattagtt tcaaacaagg gttgtttttc cgaaccgatg     840
gctggactat ctaatggatt ttcgctcaac gccacaaaac ttgccaaatc ttgtagcagc     900
aatctagctt tgtcgatatt cgtttgtgtt ttgttttgta ataaaggttc gacgtcgttc     960
```

```
aaaatattat gcgcttttgt atttctttca tcactgtcgt tagtgtacaa ttgactcgac   1020
gtaaacacgt taaataaagc ttggacatat ttaacatcgg gcgtgttagc tttattaggc   1080
cgattatcgt cgtcgtccca accctcgtcg ttagaagttg cttccgaaga cgattttgcc   1140
atagccacac gacgcctatt aattgtgtcg gctaacacgt ccgcgatcaa atttgtagtt   1200 gagcttttg gaattatttc tgattgcggg cgttttggg cgggtttcaa tctaactgtg    1260
cccgatttta attcagacaa cacgttagaa agcgatggtg caggcggtgg taacatttca   1320
gacggcaaat ctactaatgg cggcggtggt ggagctgatg ataaatctac catcggtgga   1380
ggcgcaggcg gggctggcgg cggaggcgga ggcggaggtg gtggcggtga tgcagacggc   1440
ggtttaggct caaatgtctc tttaggcaac acagtcggca cctcaactat tgtactggtt   1500
tcgggcgccg ttttttggtt t gaccggtctg agacgagtgc gattttttc gtttctaata   1560 gcttccaaca attgttgtct gtcgtctaaa ggtgcagcgg gttgaggttc cgtcggcatt   1620 ggtgagcgg gcggcaattc agacatcgat ggtggtggtg gtggtggagg cgctggaatg   1680
ttaggcacgg gagaaggtgg tggcggcggt gccgccggta taatttgttc tggtttagtt   1740
tgttcgcgca cgattgtggg caccggcgca ggcgccgctg gctgcacaac ggaaggtcgt   1800
ctgcttcgag gcagcgcttg gggtggtggc aattcaatat tataattgga atacaaatcg   1860
taaaaatctg ctataagcat tgtaatttcg ctatcgttta ccgtgccgat atttaacaac   1920
cgctcaatgt aagcaattgt attgtaaaga gattgtctca agctccgcac gccgataaca   1980
agccttttca tttttactac agcattgtag tggcgagaca cttcgctgtc gtcgacgtac   2040
atgtatgctt tgttgtcaaa aacgtcgttg gcaagcttta aaatatttaa aagaacatct   2100
ctgttcagca ccactgtgtt gtcgtaaatg ttgtttttga aatttgcgc ttccgcagta    2160 tcgacacgtt caaaaaattg atgcgcatca attttgttgt tcctattatt gaataaataa   2220
gattgtacag attcatatct acgattcgtc atggccacca caaatgctac gctgcaaacg   2280
ctggtacaat tttacgaaaa ctgcaaaaac gtcaaaactc ggtataaaat aatcaacggg   2340
cgctttggca aaatatctat tttatcgcac aagcccacta gcaaattgta tttgcagaaa   2400
acaatttcgg cgcacaattt taacgctgac gaaataaaag ttcaccagtt aatgagcgac   2460
cacccaaatt ttataaaaat ctattttaat cacggttcca tcaacaacca agtgatcgtg   2520
atggactaca ttgactgtcc cgatttattt gaaacactac aaattaaagg cgagctttcg   2580
taccaacttg ttagcaatat tattagacag ctgtgtgaag cgctcaacga tttgcacaag   2640
cacaatttca tacacaacga cataaaactc gaaaatgtct tatatttcga agcacttgat   2700
cgcgtgtatg tttgcgatta cggattgtgc aaacacgaaa actcacttag cgtgcacgac   2760
ggcacgttgg agtattttag tccggaaaaa attcgacaca caactatgca cgtttcgttt   2820
gactggtacg cggcgtgtta acatacaagt tgctaaccgg cggttcgtaa tcatggtcat   2880 agctgttttcc tgtgtgaaat tgttatccgc tcacaattcc acacaacata cgagccggaa   2940
gcataaagtg taaagcctgg ggtgcctaat gagtgagcta actcacatta attgcgttgc   3000
gctcactgcc cgctttccag tcgggaaacc tgtcgtgcca gctgcattaa tgaatcggcc   3060
aacgcgcggg gagaggcggt ttgcgtattg gcgctcttc cgcttcctcg ctcactgact   3120
cgctgcgctc ggtcgttcgg ctgcggcgag cggtatcagc tcactcaaag gcggtaatac   3180
ggttatccac agaatcaggg gataacgcag gaaagaacat gtgagcaaaa ggccagcaaa   3240
aggccaggaa ccgtaaaaag gccgcgttgc tggcgttttt ccataggctc cgcccccctg   3300
acgagcatca caaaaatcga cgctcaagtc agaggtggcg aaacccgaca ggactataaa   3360
```

```
gataccaggc gtttccccct ggaagctccc tcgtgcgctc tcctgttccg accctgccgc    3420
ttaccggata cctgtccgcc tttctccctt cgggaagcgt ggcgctttct catagctcac    3480
gctgtaggta tctcagttcg gtgtaggtcg ttcgctccaa gctgggctgt gtgcacgaac    3540
cccccgttca gcccgaccgc tgcgccttat ccggtaacta tcgtcttgag tccaacccgg    3600
taagacacga cttatcgcca ctggcagcag ccactggtaa caggattagc agagcgaggt    3660
atgtaggcgg tgctacagag ttcttgaagt ggtggcctaa ctacggctac actagaagga    3720
cagtatttgg tatctgcgct ctgctgaagc cagttacctt cggaaaaaga gttggtagct    3780
cttgatccgg caaacaaacc accgctggta gcggtggttt ttttgtttgc aagcagcaga    3840
ttacgcgcag aaaaaaagga tctcaagaag atcctttgat cttttctacg ggtctgacg    3900 ctcagtggaa cgaaaactca cgttaaggga ttttggtcat gagattatca aaaggatct    3960 tcacctagat ccttttaaat taaaaatgaa gttttaaatc aatctaaagt atatatgagt    4020
aaacttggtc tgacagttac caatgcttaa tcagtgaggc acctatctca gcgatctgtc    4080
tatttcgttc atccatagtt gcctgactcc ccgtcgtgta gataactacg atacgggagg    4140
gcttaccatc tggccccagt gctgcaatga taccgcgaga cccacgctca ccggctccag    4200
atttatcagc aataaaccag ccagccggaa gggccgagcg cagaagtggt cctgcaactt    4260
tatccgcctc catccagtct attaattgtt gccgggaagc tagagtaagt agttcgccag    4320
ttaatagttt gcgcaacgtt gttgccattg ctacaggcat cgtggtgtca cgctcgtcgt    4380
ttggtatggc ttcattcagc tccggttccc aacgatcaag gcgagttaca tgatccccca    4440
tgttgtgcaa aaaagcggtt agctccttcg gtcctccgat cgttgtcaga agtaagttgg    4500
ccgcagtgtt atcactcatg gttatggcag cactgcataa ttctcttact gtcatgccat    4560
ccgtaagatg cttttctgtg actggtgagt actcaaccaa gtcattctga atagtgta     4620 tgcggcgacc gagttgctct tgcccggcgt caatacggga taataccgcg ccacatagca    4680
gaactttaaa agtgctcatc attggaaaac gttcttcggg gcgaaaactc tcaaggatct    4740
taccgctgtt gagatccagt tcgatgtaac ccactcgtgc acccaactga tcttcagcat    4800
cttttacttt caccagcgtt tctgggtgag caaaaacagg aaggcaaaat gccgcaaaaa    4860
agggaataag ggcgacacgg aaatgttgaa tactcatact cttcctttt caatattatt    4920 gaagcattta tcagggttat tgtctcatga gcggatacat atttgaatgt atttagaaaa    4980
ataaacaaat aggggttccg cgcacatttc cccgaaaagt gccacctgac gtctaagaaa    5040
ccattattat catgacatta acctataaaa ataggcgtat cacgaggccc tttcgtctcg    5100
cgcgtttcgg tgatgacggt gaaaacctct gacacatgca gctcccggag acggtcacag    5160
cttgtctgta agcggatgcc gggagcagac aagcccgtca gggcgcgtca gcgggtgttg    5220
gcgggtgtcg ggctggctt aactatgcgg catcagagca gattgtactg agagtgcacc    5280
atatgcggtg tgaaataccg cacagatgcg taaggagaaa ataccgcatc aggcgccatt    5340
cgccattcag gctgcgcaac tgttgggaag ggcgatcggt gcgggcctct tcgctattac    5400
gccagctggc gaaagggga tgtgctgcaa ggcgattaag ttgggtaacg ccagggtttt    5460
cccagtcacg acgttgtaaa acgacggcca gtgccaagct ttactcgtaa agcgagttga    5520
aggatcatat ttagttgcgt ttatgagata agattgaaag cacgtgtaaa atgtttcccg    5580
cgcgttggca caactattta caatgcgccc aagttataaa agattctaat ctgatatgtt    5640
ttaaaacacc tttgcggccc gagttgtttg cgtacgtgac tagcgaagaa gatgtgtgga    5700
```

```
ccgcagaaca gatagtaaaa caaaacccta gtattggagc aataatcgat ttaaccaaca    5760
cgtctaaata ttatgatggt gtgcatttt tgcgggcggg cctgttatac aaaaaaattc    5820
aagtacctgg ccagactttg ccgcctgaaa gcatagttca agaatttatt gacacggtaa    5880
aagaatttac agaaaagtgt cccggcatgt tggtgggcgt gcactgcaca cacggtatta    5940
atcgcaccgg ttacatggtg tgcagatatt taatgcacac cctgggtatt gcgccgcagg    6000
aagccataga tagattcgaa aaagccagag gtcacaaaat tgaaagacaa aattacgttc    6060
aagatttatt aatttaatta atattatttg cattctttaa caaatacttt atcctatttt    6120
caaattgttg cgcttcttcc agcgaaccaa aactatgctt cgcttgctcc gtttagcttg    6180
tagccgatca gtggcgttgt tccaatcgac ggtaggatta ggccggatat tctccaccac    6240
aatgttggca acgttgatgt tacgtttatg cttttggttt tccacgtacg tcttttggcc    6300
ggtaatagcc gtaaacgtag tgccgtcgcg cgtcacgcac aacaccggat gtttgcgctt    6360
gtccgcgggg tattgaaccg cgcgatccga caaatccacc actttggcaa ctaaatcggt    6420
gacctgcgcg tcttttttct gcattattc gtctttcttt tgcatggttt cctgaaagcc    6480
ggtgtacatg cggtttagat cagtcatgac gcgcgtgacc tgcaaatctt tggcctcgat    6540
ctgcttgtcc ttgatggcaa cgatgcgttc aataaactct tgttttttaa caagttcctc    6600
ggttttttgc gccaccaccg cttgcagcgc gtttgtgtgc tcggtgaatg tcgcaatcag    6660
cttagtcacc aactgtttgc tctcctcctc ccgttgtttg atcgcgggat cgtacttgcc    6720
ggtgcagagc acttgaggaa ttacttcttc taaaagccat tcttgtaatt ctatggcgta    6780
aggcaatttg gacttcataa tcagctgaat cacgccggat ttagtaatga gcactgtatg    6840
cggctgcaaa tacagcgggt cgcccctttt cacgacgctg ttagaggtag ggccccatt    6900 ttggatggtc tgctcaaata acgatttgta tttattgtct acatgaacac gtatagcttt    6960
atcacaaact gtatatttta aactgttagc gacgtccttg ccacgaacc ggacctgttg    7020 gtcgcgctct agcacgtacc gcaggttgaa cgtatcttct ccaaatttaa attctccaat    7080
tttaacgcga gccattttga tacacgtgtg tcgattttgc aacaactatt gttttttaac    7140
gcaaactaaa cttattgtgg taagcaataa ttaaatatgg gggaacatgc gccgctacaa    7200
cactcgtcgt tatgaacgca gacggcgccg gtctcggcgc aagcggctaa acgtgttgc    7260 gcgttcaacg cggcaaacat cgcaaaagcc aatagtacag ttttgatttg catattaacg    7320 gcgattttt aaattatctt atttaataaa tagttatgac gcctacaact ccccgcccgc    7380
gttgactcgc tgcacctcga gcagttcgtt gacgccttcc tccgtgtggc cgaacacgtc    7440
gagcgggtgg tcgatgacca gcggcgtgcc gcacgcgacg cacaagtatc tgtacaccga    7500
atgatcgtcg ggcgaaggca cgtcggcctc caagtggcaa tattggcaaa ttcgaaaata    7560
tatacagttg ggttgtttgc gcatatctat cgtggcgttg ggcatgtacg tccgaacgtt    7620
gatttgcatg caagccgaaa ttaaatcatt gcgattagtg cgattaaaac gttgtacatc    7680
ctcgctttta atcatgccgt cgattaaatc gcgcaatcga gtcaagtgat caaagtgtgg    7740
aataatgttt tctttgtatt cccgagtcaa gcgcagcgcg tattttaaca aactagccat    7800
cttgtaagtt agtttcattt aatgcaactt tatccaataa tatattatgt atcgcacgtc    7860
aagaattaac aatgcgcccg ttgtcgcatc tcaacacgac tatgatagag atcaaataaa    7920
gcgcgaatta aatagcttgc gacgcaacgt gcacgatctg tgcacgcgtt ccggcacgag    7980 cttttgattgt aataagttt tacgaagcga tgacatgacc cccgtagtga caacgatcac    8040
gcccaaaaga actgccgact acaaaattac cgagtatgtc ggtgacgtta aaactattaa    8100
```

```
gccatccaat cgaccgttag tcgaatcagg accgctggtg cgagaagccg cgaagtatgg    8160
cgaatgcatc gtataacgtg tggagtccgc tcattagagc gtcatgttta gacaagaaag    8220
ctacatattt aattgatccc gatgatttta ttgataaatt gaccctaact ccatacacgg    8280
tattctacaa tggcggggtt ttggtcaaaa tttccggact gcgattgtac atgctgttaa    8340
cggctccgcc cactattaat gaaattaaaa attccaattt taaaaaacgc agcaagagaa    8400
acatttgtat gaaagaatgc gtagaaggaa agaaaaatgt cgtcgacatg ctgaacaaca    8460
agattaatat gcctccgtgt ataaaaaaaa tattgaacga tttgaaagaa aacaatgtac    8520
cgcgcggcgg tatgtacagg aagaggttta tactaaactg ttacattgca aacgtggttt    8580
cgtgtgccaa gtgtgaaaac cgatgtttaa tcaaggctct gacgcatttc tacaaccacg    8640
actccaagtg tgtgggtgaa gtcatgcatc ttttaatcaa atcccaagat gtgtataaac    8700
caccaaactg ccaaaaaatg aaaactgtcg acaagctctg tccgtttgct ggcaactgca    8760
agggtctcaa tcctatttgt aattattgaa taataaaaca attataaatg ctaaatttgt    8820
tttttattaa cgatacaaac caaacgcaac aagaacattt gtagtattat ctataattga    8880
aaacgcgtag ttataatcgc tgaggtaata tttaaaatca ttttcaaatg attcacagtt    8940
aatttgcgac aatataattt tattttcaca taaactagac gccttgtcgt cttcttcttc    9000
gtattccttc tcttttcat ttttctcctc ataaaaatta acatagttat tatcgtatcc    9060
atatatgtat ctatcgtata gagtaaattt tttgttgtca taaatatata tgtcttttt    9120 aatggggtgt atagtaccgc tgcgcatagt ttttctgtaa tttacaacag tgctatttc    9180 tggtagttct tcggagtgtg ttgctttaat tattaaattt atataatcaa tgaatttggg    9240
atcgtcggtt ttgtacaata tgttgccggc atagtacgca gcttcttcta gttcaattac    9300 accattttt agcagcaccg gattaacata actttccaaa atgttgtacg aaccgttaaa    9360
caaaaacagt tcacctccct tttctatact attgtctgcg agcagttgtt tgttgttaaa    9420
aataacagcc attgtaatga gacgcacaaa ctaatatcac aaaactggaaa tgtctatcaa    9480 tatatagttg ctgatatcat ggagataatt aaaatgataa ccatctcgca aataaataag    9540
tattttactg ttttcgtaac agttttgtaa taaaaaaacc tataaatatt ccggattatt    9600
cataccgtcc caccatcggg cgcggatccc gggtcgacgc caccatgctg aagggcggcc    9660
agcctgctgt gagaaacgag agagccaccg gcagcggcaa tggcagcggc ggaggggcg    9720 gaggaggatc tggcggagtg ggcatcagca ccggcacctt caacaaccag accgagttca    9780
agttcctgga gaacgctgg gtggagatca ccgccaacag cagcagactg gtgcacctga    9840
acatgcccga gagcgagaac taccggagag tggtggtgaa caacctggac aagaccgccg    9900
tgaacggcaa tatggccctg gatgacaccc acgcccagat cgtgaccccc tggagcctgg    9960
tggacgccaa cgcctgggga gtgtggttca accctggcga ctggcagctg atcgtgaaca    10020
ccatgagcga gctgcacctg gtgtccttcg agcaggagat tttcaacgtg gtgctgaaaa    10080
ccgtgtccga gagcgccacc cagcccccca ccaaagtgta caacaacgac ctgaccgcct    10140
ccctgatggt ggccctggac agcaacaaca ccatgccctt cacccctgcc gccatgagaa    10200
gcgagaccct gggcttctac ccttggaagc ccaccatccc cacccttgg cggtactact    10260 tccagtggga caggaccctg atccccagcc acaccggcac cagcggcacc cctaccaata    10320
tctaccacgg caccgaccct gatgacgtgc agttctacac catcgagaac agcgtgcctg    10380
tgcacctgct gagaaccggc gacgagttcg ccaccggcac attcttcttc gactgcaagc    10440
```

```
cctgcagact gacccacacc tggcagacca acagagccct gggcctgcct cctttcctga    10500
acagcctgcc ccaggccgag ggcggcacca acttcggcta catcggcgtg cagcaggaca    10560
agagaagagg cgtgacccag atgggcaaca ccaactacat caccgaggcc accatcatga    10620
gacccgccga agtgggctac agcgccccct actacagctt cgaggccagc acccagggcc    10680
ccttcaagac ccccatcgcc gctggcagag gcggagccca gaccgacgag aaccaggccg    10740
ccgacggcga ccccagatac gccttcggca gacagcacgg ccagaaaacc accaccaccg    10800
gcgagacccc cgagagattc acctacatcg cccaccagga caccggcaga taccccgagg    10860
gcgactggat tcagaacatc aacttcaacc tgcccgtgac cgaggataat gtgctgctgc    10920
ccaccgaccc catcggcggc aagaccggca tcaactacac caacatcttc aacacctacg    10980 gcccctgac cgccctgaat aacgtgcccc ccgtgtaccc caacggccag atttgggaca    11040
aggagttcga caccgacctg aagcctaggc tgcacgtgaa tgcccccttc gtgtgtcaga    11100
acaactgccc tggccagctg tttgtgaaag tggcccccaa cctgaccaac gagtacgatc    11160
ctgacgccag cgccaacatg agccggatcg tgacctacga cgacttctgg tggaagggca    11220
agctggtgtt caaggccaag ctgagagcca gccacacatg gaacccatc cagcagatga    11280 gcatcaacgt ggacaaccag ttcaactacg tgcccagcaa tatcggcggc atgaagatcg    11340
tgtacgagaa gagccagctg gcccccagaa agctgtactg ataat                   11385
```